United States Patent [19]

Clive et al.

[11] Patent Number: 5,072,002
[45] Date of Patent: Dec. 10, 1991

[54] SYNTHESIS OF CHOLESTEROL-LOWERING AGENTS

[75] Inventors: Derrick L. J. Clive, Edmonton; Andrew G. H. Wee, Regina; Kammaralli S. K. Murthy, Edmonton, all of Canada

[73] Assignee: The Governors of the University of Alberta, Edmonton, Canada

[21] Appl. No.: 381,485

[22] Filed: Jul. 18, 1989

[51] Int. Cl.$^5$ .............................................. C07F 7/08
[52] U.S. Cl. .................................. 549/214; 549/292; 549/374; 549/375
[58] Field of Search ............... 549/292, 214, 324, 375

[56] References Cited

PUBLICATIONS

T. Rosen, et al., *Tetrahedron*, "Synthesis of Meuinic Acido," 42 (No. 18), pp. 4909–4951 (1986).
D. Clive et al., *J. Am. Chem. Soc.*, "Total Synthesis of Both (+) Compactin and (+)-Meuinolin," 110 (No. 20), pp. 6914–6917 (1988).
J. McMarrg et al., (I), *J. Org. Chem.*, "Improved procedures for the reductive coupling . . . " 41 (No. 5), pp. 896–897 (1976).
J. McMurray et al. (II), *J. Org. Chem.*, "Titanium-induced reductive coupling of carbonyls to olefins," 43(17), pp. 3255–3266 (1978).
P. C. Anderson, et al. *Tet. Lett.*, "Synthetic studies related to compactin and mevinolin . . . , " 24 (No. 13), pp. 1373–1376 (1983).
M. Hirama, et al. *Tet. Lett.*, "Total synthesis of (+) Monacolin K (Mevinolin)," 24 (no. 17), pp. 1811–1812, (1983).
J. McMurry et al. (III), *J. Am. Chem. Soc.*, "A new method of reductive coupling of carbonyls to olefins 96(14), pp. 4708–4709 (1974).
J. McMurry, *Accounts Chemical Research*, "Titanium—induced dicarbonyl coupling reactions," 16, pp. 405–411 (1983).

*Primary Examiner*—Richard L. Raymond
*Assistant Examiner*—Mark W. Rossell
*Attorney, Agent, or Firm*—Bell, Seltzer, Park & Gibson

[57] ABSTRACT

Processes of synthesizing compounds of the formula:

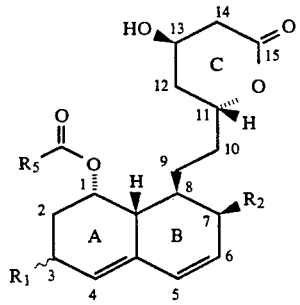

wherein
$R_1$ is H, lower alkyl (1 to 6 C), lower dialkyl (1 to 6 C), lower cycloalkyl (3 to 7 C), or lower dicycloalkyl (3 to 7 C);
$R_2$ is H, lower alkyl (1 to 6 C), or lower cycloalkyl (3 to 7 C);
$R_5C(O)$ is an acyl group which $R_5$ being alkyl (1 to 18 C), cycloalkyl, bicycloalkyl, tricycloalkyl, alkenyl (1 to 18 C), alkadienyl (1 to 18 C), aryloxy-, alkoxy-, substituted alkyl, wherein the substituents are acetoxy-, acyl-, alkoxy-, alkoxycarbonyl-, alkylamido-, alkylsulfonyl-, alkylsulfoxido-, alkylthio-, alkylthiocarbonyl-, amino-, aroyl-, aryl-, aryloxy-, arylthio-, azido-, carboxy-, dialkylamido-, dialkylamino-, dihalogeno-, hydroxy-, monohalogeno-, trihalogeno-, or arylalkylthio-.

Compounds of the above formula are capable of appreciable lowering blood levels of cholesterol in human beings. Some of the above compounds are known fungal metabolites; however, the process of this invention provides a total synthetic approach to making any of the above compounds.

14 Claims, No Drawings

SYNTHESIS OF CHOLESTEROL-LOWERING AGENTS

FIELD OF THE INVENTION

This invention relates to compounds capable of lowering blood levels of cholesterol in animals, including man, and processes for preparing such compounds.

BACKGROUND OF THE INVENTION

Elevated levels of blood cholesterol have been associated with coronary artery disease which is one of the major causes of death in Western industrialized societies. The relationship between blood cholesterol and heart disease, although complicated, is now better understood. Cholesterol is an essential ingredient of mammalian cells, because it is needed for the cell membrane and some cells also require cholesterol to make certain hormones. Cholesterol is transported in body fluids by lipoproteins. The main lipoprotein implicated in heart disease is the low density lipoprotein (LDL). When LDL cholesterol levels in the blood are high, then the person is likely to suffer from atherosclerosis.

Two known compounds useful in reducing LDL cholesterol levels are Compactin and Mevinolin of the following formula:

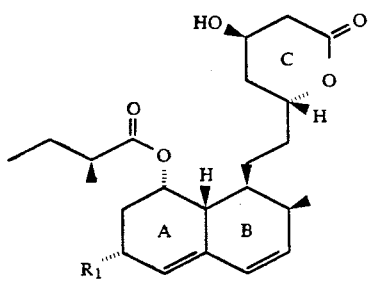

wherein $R_1$ is H or methyl, respectively.

It has been found that these compounds possess the unusual property of lowering blood levels of cholesterol in animals, including man. It is thought that these compounds are reversible, competitive inhibitors of an important enzyme that is involved in cholesterol biosynthesis, which occurs mainly in the liver. When this enzyme in the synthesis is inhibited, cells manufacture more LDL receptors which thereby remove LDL cholesterol from the blood stream. The net result of administering either Compactin or Mevinolin to human beings is that the concentration in the blood of LDL cholesterol is reduced.

Difference in activity has been observed between Compactin wherein R is H, and Mevinolin, wherein R is methyl. Based on existing biological data, it appears that Mevinolin is several times more active in lowering LDL cholesterol levels as compared to Compactin. Although the fungal metabolites are useful in the treatment of elevated cholesterol blood levels, it is apparent that a synthetic route to these compounds would enable modifications in the structure of the compounds to be made so as to arrive at more active derivatives. Considerable thought has been given to the synthesis of these compounds and this work has been reviewed by T. Rosen and C. H. Heathcock, Tetrahedron 1986, 42:4909. The syntheses reviewed in this reference, however, lack stereocontrol and/or regiocontrol and/or are not sufficiently flexible to afford analogues without extensive redesign of the synthetic route. Hence it is difficult to produce by these known synthetic routes a range of optically pure analogues.

SUMMARY OF THE INVENTION

According to this invention, the synthetic pathway to the compounds which cause a lowering of cholesterol levels in the blood stream, some of which are novel compounds, involves a number of intermediate steps which lead to the efficient production in optically pure form of the desired compounds.

According to one aspect of the invention, a process is provided for dicarbonyl coupling in forming the basic ring structure of the desired compounds. The process involves a method for preparing the intermediate compound of the formula:

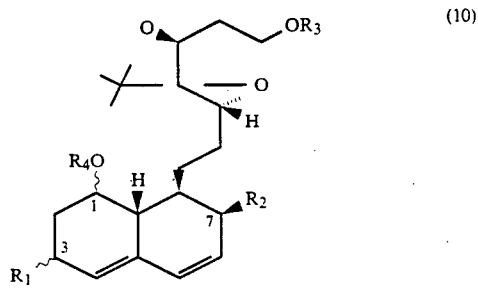

wherein:

$R_1$ is H, lower alkyl (1 to 6 C), lower dialkyl (1 to 6 C), lower cycloalkyl (3 to 7 C), lower dicycloalkyl (3 to 7 C);

$R_2$ is H, lower alkyl (1 to 6 C), lower cycloalkyl (3 to 7 C);

$OR_3$ and $OR_4$ are differentially protected hydroxyl groups where $R_4$ is other than H and, preferably, but not essentially, $R_3$ is $SiPh_2Bu$-t and $R_4$ is H or $SiEt_3$ or $SiMe_3$.

The stereochemistry at C-3 can be of R or S configuration, as desired when C-3 is monosubstituted.

The process comprises the step of cyclizing a compound of the formula

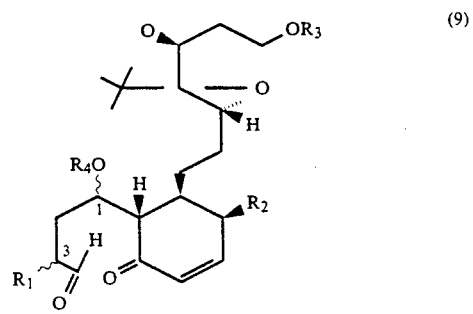

wherein $R_1$, $R_2$, $R_3$ and $R_4$ are as defined above.

According to another aspect of the invention, a process is described for preparing a subsequent intermediate compound of the formula:

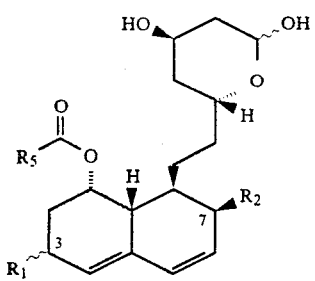

(17)

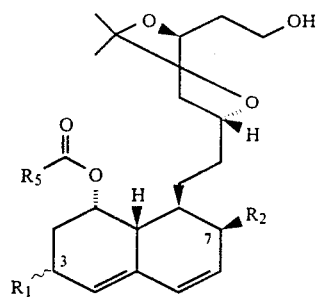

(15)

wherein:

$R_1$ is H, lower alkyl (1 to 6 C), lower dialkyl (1 to 6 C), lower cycloalkyl (3 to 7 C), lower dicycloalkyl (3 to 7 C);

$R_2$ is H, lower alkyl (1 to 6 C), lower cycloalkyl (3 to 7 C);

$R_5C(O)$ is an acyl group with $R_5$ being alkyl (1 to 18 C), cycloalkyl, bicycloalkyl, tricycloalkyl, alkenyl (1 to 18 C), alkadienyl (1 to 18 C), aryloxy-, alkoxy-, substituted alkyl, wherein the substituents are acetoxy-, acyl-, alkoxy-, alkoxycarbonyl-, alkylamido-, alkylsulfonyl-, alkylsulfoxido-, alkylthio-, alkylthiocarbonyl-, amino-, aroyl-, aryl-, aryloxy-, arylthio-, azido-, carboxy-, dialkylamido-, dialkylamino-, dihalogeno-, hydroxy-, monohalogeno-, trihalogeno-, arylalkylthio-.

As will be obvious to one skilled in the art, the $R_5C(O)$ unit can be changed later in the synthesis because numerous $R_5C(O)$ groups have been used to replace the methylbutyroyl group of natural Compactin and Mevinolin.

The stereochemistry at C-3 can be of R or S configuration, as desired, when C-3 is monosubstituted.

The process comprises the step of hydrolyzing the ketal group of the compound represented by the formula

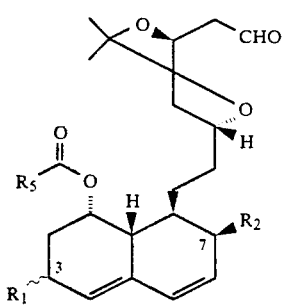

(16)

wherein $R_1$, $R_2$ and $R_5$ are as above and the stereochemistry at C-3 can be of R or S configuration as desired, if C-3 is monosubstituted According to another aspect of the invention, a process is provided for preparing a precursor of the compound of formula 16, namely a compound of the following formula:

wherein:

$R_1$ is H, lower alkyl (1 to 6 C), lower dialkyl (1 to 6 C), lower cycloalkyl (3 to 7 C), lower dicycloalkyl (3 to 7 C);

$R_2$ is H, lower alkyl (1 to 6 C), lower cycloalkyl (3 to 7 C);

$R_5C(O)$ is an acyl group with $R_5$ being alkyl (1 to 18 C), cycloalkyl, bicycloalkyl, tricycloalkyl, alkenyl (1 to 18 C), alkadienyl (1 to 18 C), aryloxy-, alkoxy-, substituted alkyl, wherein the substituents are acetoxy-, acyl-, alkoxy-, alkoxycarbonyl-, alkylamido-, alkylsulfonyl-, alkylsulfoxido-, alkylthio-, alkylthiocarbonyl-, amino-, aroyl-, aryl-, aryloxy-, arylthio-, azido-, carboxy-, dialkylamido-, dialkylamino-, dihalogeno-, hydroxy-, monohalogeno-, trihalogeno-, arylalkylthio-.

As will be apparent to one skilled in the art, the $R_5C(O)$ unit can be changed later in the synthesis because numerous $R_5C(O)$ groups have been used to replace the methylbutyroyl group of natural Compactin and Mevinolin.

The stereochemistry at C-3 can be of R or S configuration, as desired if C-3 is monosubstituted.

The process comprises the step of oxidizing the alcohol group of the compound represented by the above formula (15):

According to another aspect of the invention, a process is provided for preparing a compound of the formula:

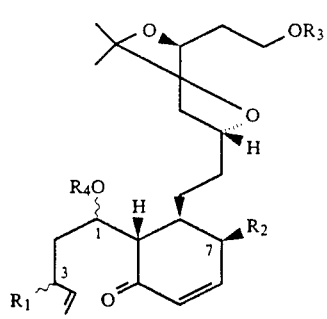

(7)

wherein:

$R_1$ is H, lower alkyl (1 to 6 C), lower dialkyl (1 to 6 C), lower cycloalkyl (3 to 7 C), lower dicycloalkyl (3 to 7 C);

$R_2$ is H, lower alkyl (1 to 6 C), lower cycloalkyl (3 to 7 C);

$OR_3$ and $OR_4$ are differentially protected hydroxyl groups, preferably, but not essentially, $R_3$ is $SiPh_2Bu$-t and $R_4$ is H or $SiEt_3$ or $SiMe_3$.

The stereochemistry at C-3 can be of R or S configuration, as desired, if C-3 is monosubstituted.

The process comprises reacting a compound of the formula:

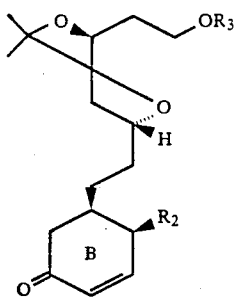

wherein $R_2$ and $R_3$ are as defined above, with a compound of the formula:

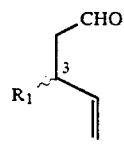

wherein $R_1$ is as defined above (and the stereochemistry at C-3 can be R or S, as desired) by deprotonating the compound of formula 6 and reacting with the compound of formula 6A.

According to another aspect of the invention, novel compounds are provided of the formula:

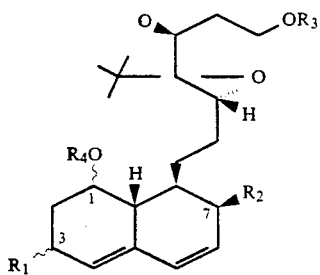

wherein:

$R_1$ is H, lower alkyl (1 to 6 C), lower dialkyl (1 to 6 C), lower cycloalkyl (3 to 7 C), lower dicycloalkyl (3 to 7 C);

$R_2$ is H, lower alkyl (1 to 6 C), lower cycloalkyl (3 to 7 C);

$OR_3$ and $OR_4$ are differentially protected hydroxyl groups, preferably, but not essentially, $R_3$ is $SiPh_2Bu$-t and $R_4$ is H or $SiEt_3$ or $SiMe_3$.

The stereochemistry at C-3 can be of R or S configuration, as desired, if C-3 is monosubstituted.

According to another aspect of the invention, novel compounds are provided of the formula:

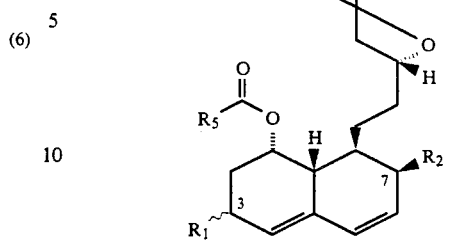

wherein:

$R_1$ is H, lower alkyl (1 to 6 C), lower dialkyl (1 to 6 C), lower cycloalkyl (3 to 7 C), lower dicycloalkyl (3 to 7 C);

$R_2$ is H, lower alkyl (1 to 6 C), lower cycloalkyl (3 to 7 C);

$R_5C(O)$ is an acyl group with $R_5$ being alkyl (1 to 18 C), cycloalkyl, bicycloalkyl, tricycloalkyl, alkenyl (1 to 18 C), alkadienyl (1 to 18 C), aryloxy-, alkoxy-, substituted alkyl, wherein the substituents are acetoxy-, acyl-, alkoxy-, alkoxycarbonyl-, alkylamido-, alkylsulfonyl-, alkylsulfoxido-, alkylthio-, alkylthiocarbonyl-, amino-, aroyl-, aryl-, aryloxy-, arylthio-, azido-, carboxy-, dialkylamido-, dialkylamino-, dihalogeno-, hydroxy-, monohalogeno-, trihalogeno-, arylalkylthio-.

The stereochemistry at C-3 can be of R or S configuration, as desired, if C-3 is monosubstituted.

According to another aspect of the invention, novel compounds are provided of the formula:

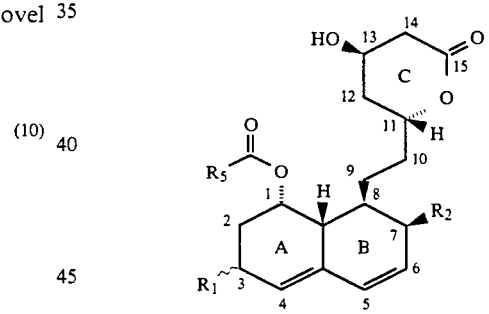

wherein:

$R_1$ is H, lower alkyl (1 to 6 C), lower dialkyl (1 to 6 C), lower cycloalkyl (3 to 7 C), lower dicycloalkyl (3 to 7 C);

$R_2$ is H, lower alkyl (1 to 6 C), lower cycloalkyl (3 to 7 C);

$R_5C(O)$ is an acyl group with $R_5$ being alkyl (1 to 18 C), cycloalkyl, bicycloalkyl, tricycloalkyl, alkenyl (1 to 18 C), alkadienyl (1 to 18 C), aryloxy-, alkoxy-, substituted alkyl, wherein the substituents are acetoxy-, acyl-, alkoxy-, alkoxycarbonyl-, alkylamido-, alkylsulfonyl-, alkylsulfoxido-, alkylthio-, alkylthiocarbonyl-, amino-, aroyl-, aryl-, aryloxy-, arylthio-, azido-, carboxy-, dialkylamido-, dialkylamino-, dihalogeno-, hydroxy-, monohalogeno-, trihalogeno-, arylalkylthio-.

DETAILED DESCRIPTION OF THE PREFERRED EMBODIMENTS

The synthesis, according to this invention, exercises sufficient stereo control to provide a high yield of the desired optically pure isomers. To achieve the desired stereo control in synthesizing compounds of this invention in principle, compounds of the following formulas would be combined by an aldol reaction.

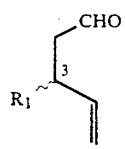
(6A)

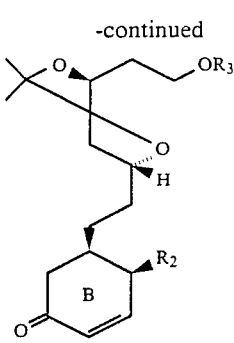
(6)

wherein $R_1$, $R_2$, $R_3$ are defined as above and the stereochemistry at C-3 in 6A, when monosubstituted, can be of R or S configuration, as desired. The aldol product is transformed by standard processes into the enone-aldehyde 9, wherein $R_1$, $R_2$ and $R_3$ are as defined above, and $R_4$ is preferably, but not essentially, $SiEt_3$ or $SiMe_3$. The stereochemistry at C-3 can be R or S configuration, as desired, if C-3 is monosubstituted. The two carbonyl units of compound 9 are joined by a modified reaction involving the use of titanium Although the above strategy constitutes a preferred aspect of the process of the invention in producing desired optically pure compounds, it is appreciated that various synthesis routes may be available in arriving at the above compounds. However, the following outlines the preferred synthesis route to the final compound To facilitate an understanding of the preferred synthesis route, the following scheme is provided:

CHART 1
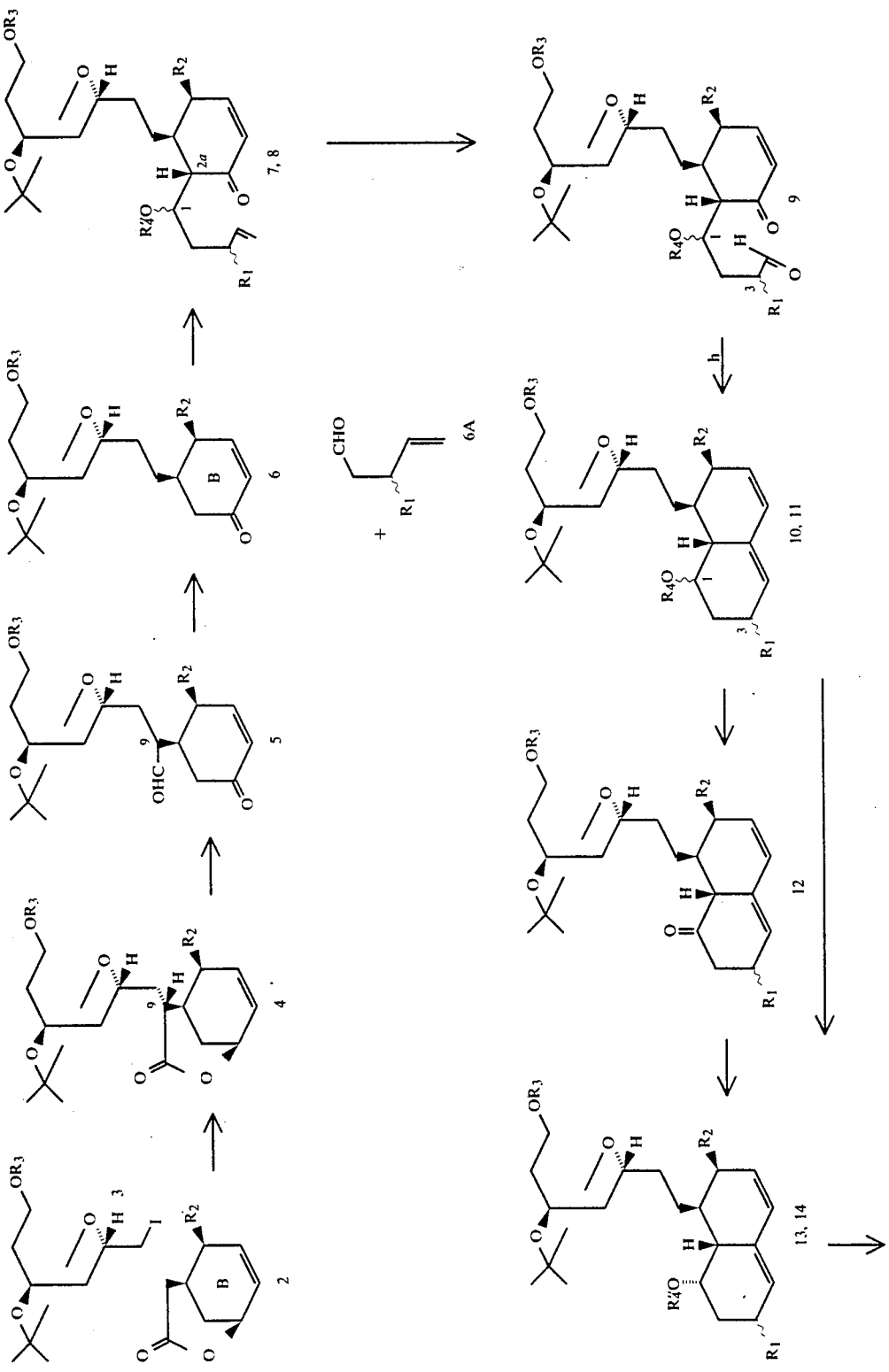

CHART 1 -continued
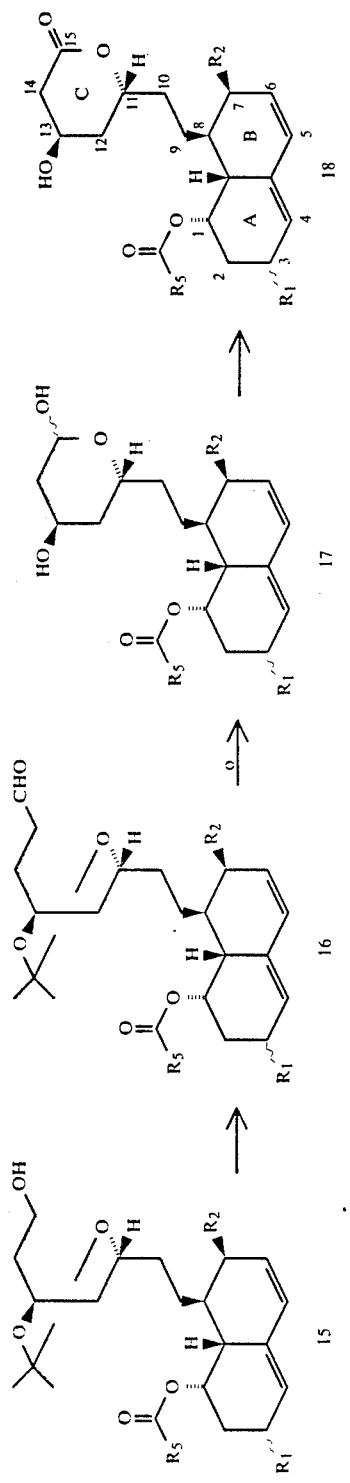

In the above formulas, the substituents have the following designations:

$R_1$ is H, lower alkyl (1 to 6 C), lower dialkyl (1 to 6 C), lower cycloalkyl (3 to 7 C), lower dicycloalkyl (3 to 7 C);

$R_2$ is H, lower alkyl (1 to 6 C), lower cycloalkyl (3 to 7 C);

$OR_3$ and $OR_4$ are differentially protected hydroxyl groups, preferably, but not essentially, $R_3$ is $SiPh_2Bu$-t and $R_4$ is H, $SiEt_3$, or $SiMe_3$, with the provisos that: (a) in the initial aldol product (7) $R_4$ is H, and the C-1 hydroxyl must be protected before ozonolysis, by converting 7 into 8, wherein $R_4$ is not H; (b) in the ozonolysis product (9) and in the immediate product of titanium coupling (10), $R_4$ is not H; (c) in compound 11, which is used to prepare ketone 12, $R_4$ is H; (d) in compound 13, $R_4$ is H; (e) in compound 14, $R_4$ is $R_5C(O)$, wherein $R_5$ is defined as follows:

$R_5C(O)$ is an acyl group with $R_5$ being alkyl (1 to 18 C), cycloalkyl, bicycloalkyl, tricycloalkyl, alkenyl (1 to 18 C), alkadienyl (1 to 18 C), aryloxy-, alkoxy-, substituted alkyl, wherein the substituents are acetoxy-, acyl-, alkoxy-, alkoxycarbonyl-, alkylamido-, alkylsulfonyl-, alkylsulfoxido-, alkylthio-, alkylthiocarbonyl-, amino-, aroyl-, aryl-, aryloxy-, arylthio-, azido-, carboxy-, dialkylamido-, dialkylamino-, dihalogeno-, hydroxy-, monohalogeno-, trihalogeno-, or arylalkylthio-.

The starting compounds of formulas 2 and 3 are optically pure. Processes are later described with respect to preferred synthesis techniques in providing the optically pure forms. Compounds 2 and 3 are joined by deprotonating the bicyclic lactone with an excess of LDA (lithium diisopropylamide) to prepare a compound of formula 4. The resulting enolate is treated with iodide 3 and the resultant compound of formula 4 is reduced with diisobutylaluminum hydride to give an intermediate hydroxy-aldehyde-lactol equilibrium mixture. The allylic alcohol group is oxidized with manganese dioxide to give the compound of formula 5. The formyl group is then removed by use of Wilkinson's catalyst $(Ph_3P)_3RhCl$ to yield a compound of formula 6. The compound of formula 6 constitutes what one might consider the right hand side of the desired compounds of formula 18.

The next step in producing a compound of formula 7 is an aldol reaction. The enone of formula 6 is deprotonated with LDA and condensed with the unsaturated aldehyde of formula 6A to yield a compound of formula 7. The stereochemistry in the compound of formula 7 is correct at C-8a since the aldehyde approaches from the under face of the enone. Both epimers at C-1 of formula 7 are sometimes produced, depending on the nature of $R_1$; however, the stereochemistry can be adjusted at the carbon Cl as will be later demonstrated in the reaction scheme. The hydroxyl group at carbon Cl is protected to yield a compound of formula 8, where $R_4$ becomes a suitable protecting group, such as, but not limited to, $SiEt_3$. The compound of formula 8 is subjected to ozonolysis to yield the keto aldehyde of formula 9 which has the carbonyl groups needed for the titanium coupling. The ozonolysis step is preferably stopped before completion of the reaction to optimize the yield of the product of formula 9.

The titanium reaction, according to this invention, is then employed to couple the dicarbonyl groups to form the desired alkene.

Although the standard McMurry reaction, as defined in McMurry, J. E., *Acc. Chem. Res* 1983, 16:405, can normally be used to couple dicarbonyl groups, it was found that a low yield in this reaction was obtained in producing a compound of formula 10. In accordance with this invention, the yield was considerably increased by using less than the stoichiometric amount of the reducing agent, preferably two thirds of the stoichiometric amount of the reducing agent required to reduce the titanium III salt to zero valence. Preferably this is accomplished by mixing potassium in the form of its intercalation compound with graphite, that is, $C_8K$. Two moles of this compound are mixed with one mole of titanium trichloride. Reagent prepared in this matter effects the desired dicarbonyl coupling when used in excess. The degree of excess is controlled: optimally, reagent prepared from 8 moles of $TiCl_3$ should be used per mole of carbonyl groups. It is appreciated that the ratio of $C_8K$ to $TiCl_3$ (about 2 to 1) is maintained for multiples of the reactants, for example compound 10(a), infra, wherein 34 moles of $C_8K$ are reacted with 17 moles of titanium trichloride per 1 mole of the compound of formula 9.

In an experimentally more convenient version of the titanium coupling, one mole of a (IV) salt titanium, such as titanium tetrachloride is reduced with 2.8 moles, and preferably not less than 2.7 or more than 3.0 moles, of sodium naphthalene in tetrahydrofuran. Reagent prepared in this way is used in similar excess to the potassium-graphite-derived reagent, i.e., optimally 8 moles of titanium tetrachloride per mole of carbonyl groups. As above, it is appreciated that the ratio of sodium naphthalene to $TiCl_4$ (about 2.8 to 1) is maintained for multiples of the reactants, for example compound 10(b), infra, wherein 44.8 moles of sodium naphthalene were reacted with 16 moles of titanium tetrachloride per 1 mole of the compound of formula 9. In this version of the titanium coupling reaction, the reagents are easier to handle. [Titanium tetrachloride is a liquid and can be manipulated by syringe, whereas titanium trichloride is a moisture-sensitive solid that is most conveniently weighed out in an inert atmosphere. Sodium naphthalene can be prepared without need of a dry box, but one is strongly preferred for $C_8K$.]

The compound of formula 10 is treated with dilute hydrofluoric acid to remove the C-1 protecting group. At the same time, the ketal unit may suffer partial hydrolysis. To compensate for this, the total reaction mixture is treated with the appropriate reagents for reketalization.

At this point, the reaction scheme branches depending on whether $R_1$ is hydrogen or a lower alkyl group. When $R_1$ is lower alkyl, only one stereoisomer at C-1 is produced in formula 10 where $R_1$ happens to be in the correct orientation. When $R_1$ is hydrogen, the C-1 hydroxyl is oxidized to a carbonyl of formula 12 and then reduced back to the alcohol of formula 13. The hydroxyl is thereby regenerated with the correct stereochemistry. The compound of formula 13 is then acylated to attach an acyl group, $R_5C(O)$, which can be, but is not limited to the methylbutyroyl unit of the natural compounds, Compactin and Mevinolin. The product of acylation is compound 14 wherein $R_4 = R_5C(O)$ and $R_5$ is as defined earlier.

When $R_1$ is lower alkyl, the correct stereoisomer is provided at C-1 of compounds 7, 8, 9, 10 and 11, so that the compound of formula 10 is treated to remove the silicon group with tetrabutylammonium fluoride to produce a compound of formula 11, which is then acylated directly to give a compound of formula 14, wherein $R_4=R_5C(O)$ with $R_5$ being as defined above. The compound of formula 14 is then deprotected with tetrabutylammonium fluoride to yield the compound of formula 15.

The compound of formula 15 is oxidized to give the aldehyde of formula 16 which is hydrolyzed in dilute acid, such as, but not limited to, hydrochloric acid to give the compound of formula 17. The compound of formula 17 is treated with Fetizon's reagent for the selective oxidation of the anomeric hydroxyls to yield the desired compound of formula 18.

This reaction scheme yields optically pure compounds of the formula 18 with overall relatively high yields as will be amplified in the following Examples. This synthetic route now enables the production of novel compounds similar to compactin and mevinolin. Such novel compounds, where $R_1$ is other than H or methyl, demonstrates significant cholesterol blood level lowering properties, as verified in the Examples section for the novel compound ethylcompactin and predicable for other related novel compounds.

The preferred synthetic approach in developing the compound of Formula 2 of Chart 1 is outlined in the following reaction scheme for the case wherein $R_2=Me$.

The compound of formula 19 is acylated with crotonyl chloride to yield a compound of formula 20. A standard Diels-Alder reaction catalyzed by a Lewis acid produces the compound of formula 21. The chiral auxiliary controls the stereochemical course of the reaction so that the product has the absolute configuration of formula 21.

By use of the lithium salt of benzyl alcohol, the chiral auxiliary is displaced. Then the benzyloxy unit of formula 22 is displaced with the lithium salt of methanol to provide the methyl ester of formula 23. The compound of formula 23 is deprotonated and reprotonated to give an isomeric mixture of formula 24. The isomers are suitably separated such as by spinning band distillation to give the cis ester of formula 25.

The ester of formula 25 is reduced and the hydroxyl of formula 26 converted into a leaving group which is then displaced with cyanide. The nitrile of the intermediate compound is hydrolyzed to an acid and at that stage iodolactonization is conducted. The resultant compound containing iodine is treated with a base to eliminate hydrogen iodide and generate the compound of formula 2.

The compound of formula 3 may be prepared in accordance with the following scheme to provide opti-

CHART 2

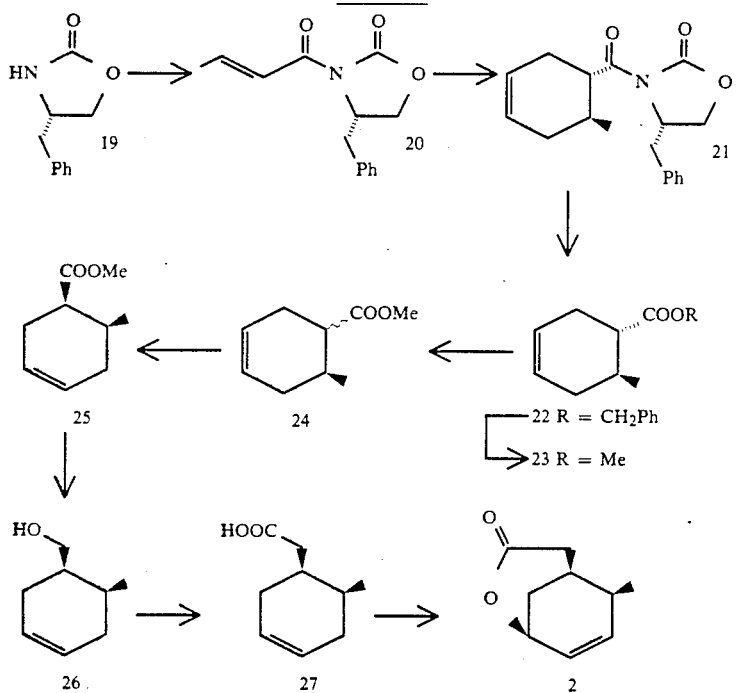

cally pure material.

CHART 3

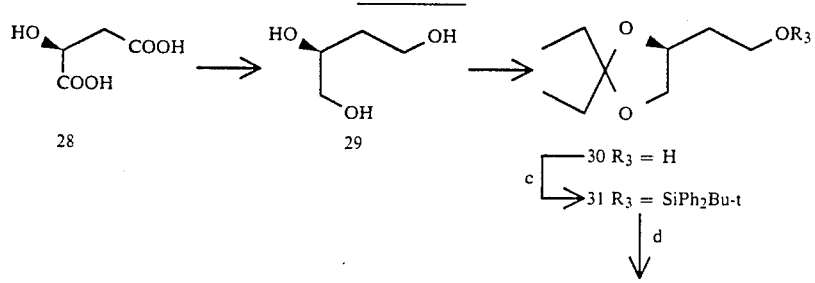

CHART 3

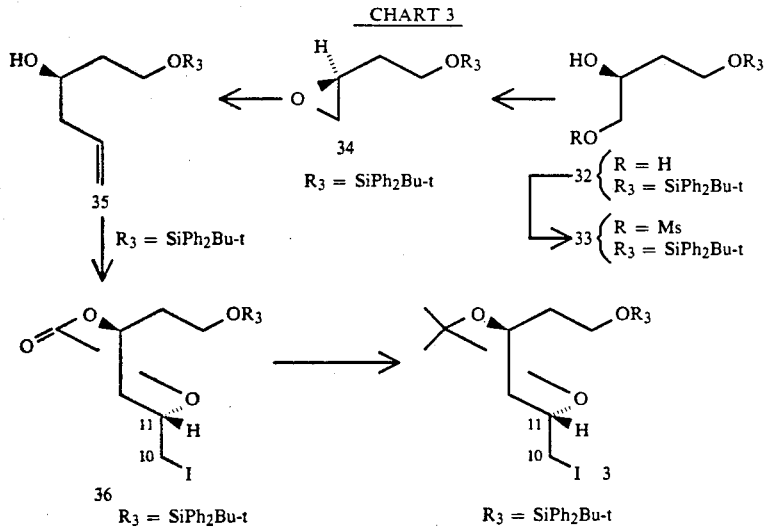

The starting material of formula 28 is commercially available S-maleic acid. The first step is to reduce maleic acid to a triol. This is best accomplished in the presence of borane. The compound of formula 29 is then ketalized to provide the alcohol 30 where $R_3$ is hydrogen. The ketalization was conducted with diethyl ketone. By use of diethyl ketone as the preferred ketalizing agent, the exact arrangement of formula 30 is assured. The next step is to protect the primary alcohol where $R_3$ is hydrogen. A suitable reactant for the protection is t-BuPh$_2$SiCl. The protected compound of formula 31 is subjected to mild acid hydrolysis to give the compound of formula 32.

This compound is then selectively mesylated to provide the compound of formula 33. This compound is then treated with a base to give the optically pure epoxide of formula 34. In order to introduce the remaining two desired carbons of the chain for this compound, a higher order organocuprate is the preferred reagent that is used to yield a compound of formula 35, which is an optically pure homoallylic alcohol.

The compound of formula 35 is then treated with butyllithium followed by carbon dioxide. This leads to a carbonate salt which is then treated with iodine to cause cyclization to produce a compound of formula 36. The carbonate function of the compound of formula 36 is then hydrolyzed and ketalized so that the two hydroxyl groups are now protected as a ketal of formula 3.

The unsaturated aldehyde of formula 6A, which is condensed with the compound of formula 6 in the form when $R_1$ is hydrogen, is a known compound [e.g. C. C. Price and R. Balsley, *J. Org. Chem.* (1966) 31 3406]. However, when $R_1$ is lower alkyl, the following preferred scheme, which illustrated the case wherein the chirality at C-3 is R, is employed to yield the desired compound.

CHART 4

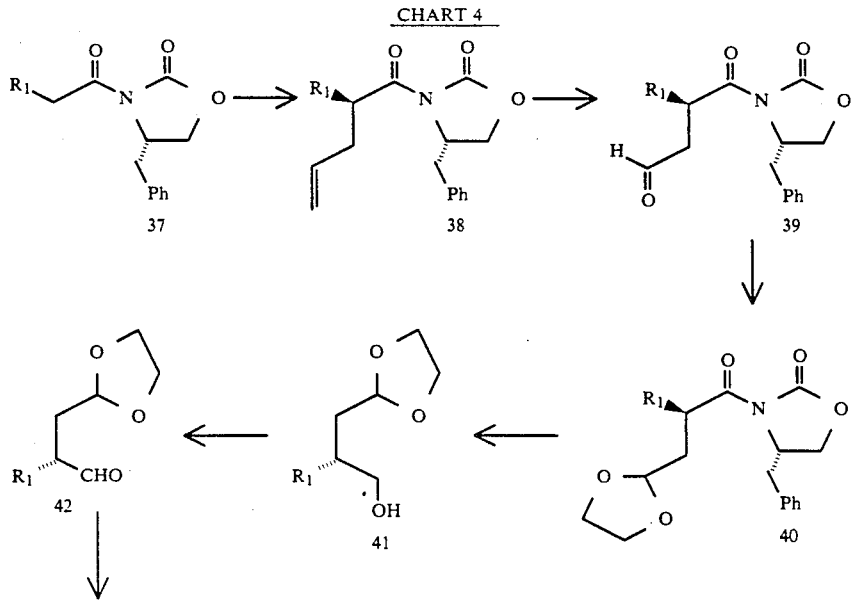

CHART 4
-continued

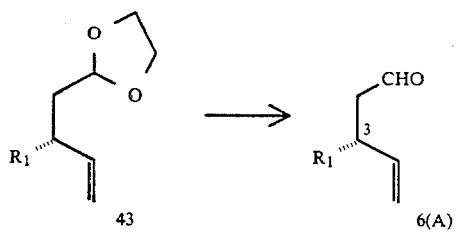

The chiral auxiliary of formula 37 is derived from the same chiral auxiliary 19 that was used in the Diels-Alder reaction of Chart 2. A propenoyl group is attached to prepare the compound of formula 37, wherein $R_1$ is methyl. Allylation of this compound in the normal way yielded the compound of formula 39, wherein $R_1$ is methyl. The double bond of the terminal olefin group of formula 38 was cleaved to an aldehyde (39) which was immediately protected to provide the compound of formula 40, wherein $R_1$ is methyl. The compound of formula 40 is reduced with LAH (lithium aluminum hydride—LiAlH$_4$) to remove the auxiliary and reduce the carbonyl to a hydroxyl of formula 41, wherein $R_1$ is methyl.

Swern oxidation was used on the compound of formula 41 to give the compound of formula 42, wherein $R_1$ is methyl. In accordance with Wittig Chemistry, the olefin of formula 43, wherein $R_1$ is methyl, is provided. In the last step, the aldehyde group is released to give the compound of formula 6A, wherein $R_1$ is methyl. Similarly, for cases wherein $R_1$ is lower alkyl (1 to 6 C) or lower cycloalkyl (3 to 7 C), the corresponding acyl group, RC(O), is attached to the chiral auxiliary 19 in place of a propanoyl group.

The following Examples demonstrate preferred parameters of the above reaction schemes to prepare the optically pure desired compounds of formula 18.

EXPERIMENTAL SECTION

General

Except where stated to the contrary, the following particulars apply: All of the following preparations, exemplary processes and procedures were performed under a slight static pressure of argon that was purified by passage through a column of R-311 catalyst (Chemical Dynamics Corp., South Plainfield, NJ) and then through a column of Drierite. Apparatus was dried at 120° C. for at least 2 h before use and cooled in a desiccator over Drierite. Solvents for reactions were dried by distillation from a suitable drying agent under argon and were transferred by syringe. Petroleum ether had bp 30°–60° C. During product isolation solutions were evaporated under water-pump vacuum at room temperature. Melting points were determined on a Kofler block. Commercial thin layer chromatography (TLC) plates (silica gel, Merck 60F-254) were used. Silica gel for flash chromatography was Merck type 60 (230–400 mesh). Infrared spectra were recorded on a Perkin-Elmer 297 Spectrophotometer or a Nicolet 7000 FT-IR model. $^1$H and $^{13}$C NMR spectra were recorded on a Bruker WH-200, Bruker AM-300, or Bruker AM-400 spectrometer in deuterated solvent using tetramethylsilane as the internal standard. The following abbreviations are used in describing spectral data: s, singlet; d, doublet; t, triplet; q, quartet; m, multiplet, b, broad.

Mass spectra were recorded on an A.E.I. MS50 mass spectrometer.

Abbreviations: DMAP, 4-(dimethylamino)pyridine; THF, tetrahydrofuran; DME, 1,2-dimethoxyethane; DMSO, dimethyl sulfoxide; LDA, lithium diisopropylamide.

EXAMPLES

("S")-1,2,4-Butanetriol Compound 29

This process and preparation was done in a fume hood. A dry 5-L 3- necked flask containing a large magnetic stirring bar and closed by septa was purged with a slow stream of argon. Borane—methyl sulfide complex (Aldrich, 2M in THF, 1.83 L, 3.65 mol) and trimethyl borate (375 mL, 3.30 mol) were transferred by cannula to the flask. The mixture was stirred and cooled in an ice-salt bath (external temperature = $-5°$ C.). One of the septa was quickly replaced by a pressure equalizing dropping funnel containing ("S")-malic acid [Aldrich, $[\alpha]_D^{20} - 28.6$ (c 5.5, pyridine), 2 150 g, 1.12 mol] in dry THF (320 mL). The dropping funnel was capped with a drying tube packed with Drierite and the argon inlet and exit needles to the reaction flask were removed. The malic acid solution was added dropwise over 3 h. Initially, a white precipitate formed, but by the end of the addition it had dissolved. At that stage the cooling-bath was removed and stirring at room temperature was continued for 48 h. Methanol (900 mL) was then added dropwise over 1 h with stirring and ice-cooling. The resulting mixture was concentrated (rotary evaporator, 40° C.). This process of addition of methanol (900 mL) and evaporation was repeated twice more. The material from this run and from another [beginning with ("S")-malic acid (150.0 g)] were combined and the mixture was diluted with toluene (500 mL), which was then evaporated (rotary evaporator, 40° C.). The addition of toluene (500 mL) and evaporation were repeated. The residual material was purified by flash chromatography over silica gel (20×100 cm) using first 2:98 methanol—dichloromethane (to remove faster-running components) and then 1:1 methanol—dichloromethane. Appropriate fractions (TLC, silica, 1:1 methanol—dichloromethane) were combined and evaporated (40° C.). The resulting thick oil was kept under oil-pump vacuum at room temperature for 3 days to afford triol compound 29 (246 g, 103%) suitable for the next stage. In a similar experiment using ("S")-malic acid (20 g) the yield was 81% and a sample was acetylated (acetic anhydride, pyridine, room temperature, 24 h; 81%). The triacetate had: $[\alpha]_D^{25} - 18.08$ (c 1.405, acetone) [lit.[1] $[\alpha]_D - 16.5$ (c 1.43, acetone)]; IR (film) 1740 cm$^{-1}$; $^1$H NMR (CDCl$_3$, 200 MHz) δ 1.85–2.0 (m, 2H), 2.05 and 2.10 (s, 9H); 4.05 (dd, 1H, J=12.0, 6.0 Hz), 4.12 (t, 2H, J=6.0 Hz), 4.30 (dd, 1H, J=12.0, 3.5 Hz), 5.15–5.25 (m, 1H); $^{13}$C NMR (CDCl$_3$, 50.32 MHz)

δ 20.55 (q), 20.69 (q), 20.78 (q), 29.76 (t), 60.07 (t), 64.67 (t), 68.45 (d), 170.19 (s), 170.48 (s), 170.72 (s); mass (chemical ionization, NH3), m/z 250 (M+18); exact mass, m/z 173.0815 (calcd for $C_8H_{13}O_4$ (M—$C_2H_3O_2$), m/z 173.0814).

[1]Hanessian, S.; Ugolini, A.; Dube, D; Glamyan, A. *Can. J. Chem.* 1984, "62", 2146.

Compound 30

($R_3$=H)[1]

A mixture of ("S")-1,2,4-butanetriol 29 (36 g, 0.34 mol), 3-pentanone (75 mL, 0.714 mol), 3,3-dimethoxypentane (67 mL, 0.51 mol), dry dichloromethane (700 mL), and "p"-toluenesulfonic acid monohydrate (1.42 g, 7.46 mmol) was stirred overnight at room temperature. Triethylamine (6 mL) was added with stirring. The solution was washed once with water ("ca" 400 mL), dried ($Na_2SO_4$), and evaporated. The residual oil was distilled to afford 30 ($R_3$=H) (42.13 g, 71%): bp 77°-80° C. (0.4 mm); IR (film) 3400 cm$^{-1}$ (broad); $^1$H NMR (CDCl3, 200 MHz) δ 0.89 (t, 3H, J=7.5 Hz), 0.91 (t, 4H, J=7.5 Hz), 1.65 (q, 2H, J=7.5 Hz), 1.71 (q, 2H, J=7.5 Hz), 1.80-1.90 (m, 2H), 1.41 (s, 1H, OH, exchanges in D2O), 3.50 (t, 1H, J=6.0 Hz), 3.80 (t, 2H, J=6.0 Hz), 4.12 (dd, 1H, J=6.0 Hz), 4.20-4.35 (m, 1H); $^{13}$C NMR (CDCl3, 50.32 MHz) δ 7.87 (q), 8.13 (q), 29.55 (t), 29.84 (t), 35.48 (t), 60.42 (t), 70.03 (t), 75.23 (d), 112.89 (s). Anal. Calcd. for $C_9H_{18}O_3$, C, 62.04; H, 10.41. Found: C, 62.09; H, 10.36.

[1]Masamune, S.; Ma, P.; Okumoto, H.; Ellingboe, J. W.; Yukishige, I. *J. Org. Chem.* 1984, "49", 2834.

Compound 31

($R_3$=SiPh2Bu-t)

Compound 30 ($R_3$=H) (117.39 g, 0.675 mol), DMAP (8.2 g, 0.067 mol), and dry triethylamine (112.8 mL, 0.809 mol) were dissolved in dry dichloromethane (1 L). The solution was stirred under an argon atmosphere and cooled in an ice-bath. Tert-Butyldiphenylsilyl chloride (200 g, 0.728 mol) in dichloromethane (100 mL) was added dropwise over 1 h. A white precipitate formed. Stirring was continued for 18 h, the ice-bath being allowed to attain room temperature. The mixture was diluted with dichloromethane (200 mL) and washed with water (2×400 mL), ice-cold 5% v/v aqueous hydrochloric acid (400 mL), water, and saturated aqueous bicarbonate solution, and dried ($Na_2SO_4$). The dichloromethane was evaporated. Distillation of the residue then afforded 31 ($R_3$=SiPh2Bu-t) (269.6 g, 96.9%): bp 170°-196° C. (0.5 mm); [α]$^{25.5}$D +0.9 (c 1.0, CHCl3); IR (film) 1590, 1110, 1080 cm$^{-1}$; $^1$H NMR (CDCl3, 200 MHz) δ 0.88 (t, 3H, J=7 5 Hz), 0.92 (t, 3H, J=7.5 Hz), 1.05 (s, 9H), 1.65 (q, 4H, J=7.5 Hz), 1.80-2.05 (m, 2H), 3.55 (t, 1H, J=8.0 Hz), 3.72 (t, 2H, J=6.1 Hz), 4.15 (dd, 1H, J=8.0, 6.0 Hz), 4.23-4.40 (m, 1H), 7.35-7.50 (m, 6H), 7.65-7.79 (m, 4H); $^{13}$C NMR (CDCl3, 50.32 MHz) δ 7.93 (q), 8.22 (q), 19.12 (s), 26.82 (q), 29.96 (t), 29.76 (t), 60.90 (t), 70.49 (t), 74.08 (d), 112.21 (s), 127.64 (d), 127.99 (d), 129.59 (d), 133.68 (d), 135.53 (d). Anal. Calcd for $C_{25}H_{36}O_3Si$: C, 72.77; H, 8.79; Si, 6.81. Found: C, 72.92; H, 8.79; Si, 6.54.

Compound 32

(R=H, $R_3$=SiPh2Bu-t)

The silyl ketal 31 ($R_3$=SiPh2Bu-t) (270.00 g, 0.65 mol) was added with stirring to 80% v/v aqueous acetic acid (700 mL) and the mixture was stirred at 50° C. (internal temperature) for 4 h. During this period the reaction was followed closely by TLC (silica, 1:1 ethyl acetate—hexane) in order to detect loss of the silyl group. Near the end of the reaction the mixture became homogeneous. It was cooled to room temperature, diluted with an equal volume of toluene and concentrated at room temperature. Dilution with toluene and concentration were carried out twice more and the residue was then evaporated further at room temperature, under oil-pump vacuum. The resulting oil was swirled with hexane ("ca" 500 mL) and the mixture was left overnight at room temperature to afford the crystalline diol 32 (R=H, $R_3$ =SiPh2Bu-t) (136.28 g): mp 69°-71° C. The mother liquors were evaporated and flash chromatography of the residue over silica gel with 1:1 ethyl acetate—hexane, followed by crystallization from hexane gave a further crop of diol with the same mp. The total yield of 32 (R=H, $R_3$=SiPh2Bu-t) amounted to 189.97 g (84%): [α]$_D$ +4.42 (c 3.03, CHCl3); IR (film) 3600-3300 cm$^{-1}$; $^1$H NMR (CDCl3, 200 MHz) δ 1.05 (s, 9H), 1.55-1.90 (m, 2H), 2.25 (t, 1H, J=6.8 Hz), 3.43 (d, 1H, J=3.2 Hz). 3.45-3.73 (m, 2H). 3.80-3.95 (m. 2H), 3.95-4.12 (m, 1H). 7.35-7.52 (m. 6H), 7.63-7.72 (m. 4H); $^{13}$C NMR (CDCl3, 100.62 MHz) δ 19.05 (s), 26.82 (q), 34.87 (t), 62.52 (t), 66.73 (t), 71.55 (d), 127.82 (d), 129.89 (d), 132.90 (d), 132.97 (d), 135.53 (d); exact mass, m/z 313.1620 (calcd for $C_{19}H_{25}O_2Si$, m/z 313.1624). Anal. Calcd for $C_{20}H_{28}O_3Si$: C, 69.73; H, 8.19. Found: C, 70.11; H, 8.26.

Compound 33

(R=MeSO2, $R_3$=SiPh2Bu-t)

Freshly distilled methanesulfonyl-chloride (37.83 g, 0.330 mol) was injected over 15 min into a magnetically stirred and cooled (−30° C.) solution of diol 32 (R=H, $R_3$=SiPh2Bu-t) (109.17 g, 0.317 mol) and dry pyridine (120 mL, 1.48 mol) in dry dichloromethane (1.2 L). After 3 h at −30° C., the cooling-bath was removed and the mixture was allowed to attain room temperature. After 24 h some starting diol was still present (TLC control) and, therefore, additional methanesulfonyl chloride (3.78 g, 0.033 mol) was added over about 5 min. After a total of 40 h no starting material remained (TLC control). The mixture was concentrated (below 40° C.) and the residual oil was taken up in ethyl acetate (2.0 L), washed with water ("ca" 700 mL), ice-cold 1N hydrochloric acid (2×700 mL), and brine ("ca" 700 mL), dried ($Na_2SO_4$) and evaporated at room temperature. The desired primary mesylate 33 (R=MeSO2, $R_3$=SiPh2Bu-t) (91.24 q, 68%) was isolated by HPLC using a Waters Prep LC System 500A instrument with two PrepPak-500/Silica cartridges and 3% v/v acetone in dichloromethane as eluent. A refractive index detector and a flow rate of 0.15 L min$^{-1}$ were used. The crude, liquid mesylation product was dissolved in an equal volume of the eluent and 25 mL-injections were made. Compound 33 (R=MeSO2, $R_3$=SiPh2Bu-t) had: IR (film) 3600-3340, 1600, 1360, 1190 cm$^{-1}$; $^1$H NMR (CDCl3, 400 MHz) δ 1.00 (s, 9H), 1.70-1.85 (m, 2H), 3.05 (s, 3H), 3.22-3.28 (bs, 1H, OH, exchanges in D2O), 3.85-3.95 (m, 2H), 4.15-4.30 (m, 3H), 7.35-7.50 (m, 6H), 7.68-7.70 (m, 4H); $^{13}$C (CDCl3, 75.48 MHz) δ 18.99 (s), 26.76 (q), 34.45 (t), 37.42 (q), 61.86 (t), 68.81 (d), 73.42 (t), 127.81 (d), 129.90 (d), 132.73 (s), 132.80 (s), 135.44 (d).

Compound 34

($R_3 = SiPh_2Bu-t$)

Benzyltrimethylammonium hydroxide (40% w/w solution in methanol, 69.0 mL, 151.8 mmol) was added from a dropping funnel to a magnetically stirred solution of the mesylate 33 ($R = MeSO_2$, $R_3 = SiPh_2Bu-t$) (57.83 g, 136.8 mmol) in anhydrous ether (500 mL). Stirring at room temperature was continued for 30 min (TLC control). The solution was then diluted with ether (700 mL), washed successively with ice-cold 1N hydrochloric acid (500 mL) and brine (500 mL), and dried ($MgSO_4$). Evaporation of the solvent (30° C.) and flash chromatography of the residue over silica gel (5×20 cm) with 1:9 ethyl acetate—hexane gave 34 ($R_3 = SiPh_2Bu-t$) (40.66 g, 91%): mp 43°–45° C.; $[\alpha]_D^{23}$ −5.46 (c 1.025, $CHCl_3$); IR (film) 1590, 1255, 1250 cm$^{-1}$; $^1H$ NMR ($CDCl_3$, 400 MHz) δ 1.05 (s, 9H), 1.75–1.84 (m, 2H), 2.52 (dd, 1H, J=5.0, 2.8 Hz), 2.80 (t, 1H, J=4.5 Hz), 3.09–3.13 (m, 1H), 3.78–3.95 (m, 2H), 7.35–7.50 (m, 6H), 7.65–7.75 (m, 4H); $^{13}C$ NMR ($CDCl_3$, 75.47 MHz) δ 19.20 (s), 26.84 (q), 35.72 (t), 47.22 (t), 50.09 (d), 60.93 (t), 127.69 (d), 129.67 (d), 133.67 (s), 133.72 (s), 135.55 (d); exact mass, m/z 269.1000 [calcd for $C_{16}H_{17}OSi$ (M—$C_4H_9$)+, m/z 269.0992]. Anal. Calcd for $C_{20}H_{26}O_2Si$: C, 73.57; H, 8.03. Found: C, 73.82; H, 8.32.

Compound 35

($R_3 = SiPh_2Bu-t$)

Vinyllithium (1.1M in THF, 38.5 mL, 42.8 mmol) was added dropwise over about 10 min to a stirred, cold (−60° C.) suspension of cuprous cyanide (1.9 g, 21.4 mmol) in dry THF. Stirring at −60° C. was continued for 30 min and then a room temperature solution of epoxide 34 ($R_3 = SiPh_2Bu-t$) (3.49 g, 10.7 mmol) in dry THF (20 mL) was added over about 15 min, a further portion of THF (10 mL) being used as a rinse. The cold-bath was replaced by an ice-methanol bath at −10° C. and, after 4 h, this, in turn, was replaced by an ice-bath. Stirring at 0° C. was continued for 20 min and then a 9:1 v/v mixture (10 mL) of saturated ammonium chloride—concentrated aqueous ammonium hydroxide was added. Insoluble material was filtered off and washed with ethyl acetate (3×50 mL). The combined filtrates were washed successively with water (100 mL) and brine (100 mL), and dried ($MgSO_4$). Evaporation of the solvent and flash chromatography of the residual oil over silica gel (3.5×17.0 cm) with 1:4 ether—petroleum ether gave 35 ($R_3 = SiPh_2Bu-t$) (3.640 g, 95%) as a homogeneous (TLC, silica, 1:4 ether—petroleum ether) oil: $[\alpha]^{28}D$ +4.26 (c 1.08, $CHCl_3$); IR (film) 3600–3300, 1630, 1590 cm$^{-1}$; $^1H$ NMR ($CDCl_3$, 200 MHz) δ 1.05 (s, 9H), 1.60–1.80 (m, 2H), 2.20–2.32 (m, 2H), 3.22 (d, 1H, J=2.5 Hz), 3.80–4.05 (m, 3H), 5.05–5.20 (m, 2H), 5.72–5.95 (m, 1H), 7.35–7.50 (m, 6H) 7.62–7.72 (m, 4H); $^{13}C$ NMR ($CDCl_3$, 75.47 MHz) δ 19.07 (s), 26.84 (q), 37.93 (t), 42.00 (t), 63.26 (t), 70.81 (d), 117.43 (t), 127.80 (d), 129.84 (d), 133.03 (s), 133.12 (s), 134.98 (d), 135.58 (d) exact mass, m/z 313.1623 [calcd for $C_{19}H_{25}O_2Si$ (M—$C_3H_5$)+, m/z 313.1625]. Anal. Calcd for $C_{22}H_{30}O_2Si$: C, 74.55; H, 8.53. Found: 74.48; H, s.68.

Compound 35

($R_3 = SiPh_2Bu-t$)

Use of Grignard Reagent

Vinylmagnesium chloride (Alpha Ventron, 2.3M THF, 50 mL, 115 mmol) was injected over 30 min into a cold (0° C.) solution of epoxide 34 ($R_3 = SiPh_2Bu-t$) (12.36 g, 37.85 mmol) in THF (50 mL) kept under a static atmosphere of argon. The ice-bath was left in place and stirring was continued for 12 h, during which time the mixture attained room temperature. The mixture was recooled to 0° C. and saturated aqueous ammonium chloride (100 mL) was added. The phases were separated and the organic layer was washed with water (2×200 mL) and brine (200 mL). The combined aqueous phases were extracted with ethyl acetate (200 mL) and the organic solution was washed with brine (100 mL). The combined organic extracts were dried ($Na_2SO_4$) and evaporated (30° C.). Flash chromatography of the residue over silica gel (6.5×17.0 cm) using 1:5 ether—petroleum ether gave 35 ($R_3 = SiPh_2Bu-t$) (11.620 g, 87%). The material was suitable for the next stage but contained (1H NMR) an impurity that was removable in the next step. The yield in this reaction is greatly reduced if 1.5M Grignard reagent is used.

Compound 36

($R_3 = SiPh_2Bu-t$)

n-Butyllithium (1.6M hexanes, 21.5 mL, 34.4 mmol) was added over about 15 min to a stirred and cooled (0° C., ice-salt bath) solution of the homoallylic alcohol 35 ($R_3 = SiPh_2Bu-t$) (11.110 g, 31.3 mmol) in THF (200 mL) containing 2,2'-dipyridyl (5 mg). The amount of butyllithium used was just sufficient to produce a permanent brick-red color. The mixture was stirred at 0° C. for 10 min and carbon dioxide, dried by passage through a column (1.8×15.0 cm) of Drierite was bubbled into the cold (0° C.) solution for 1 h. During this period the red color was discharged and the mixture became pale yellow. A solution of iodine (23.910 g, 94.2 mmol) in THF (100 mL) was then added by cannula over about 10 min, more THF (50 mL) being used as a rinse. Stirring at 0° C. was continued for 1.5 h. The cooling-bath was then removed and, after a further 2 h, no homoallylic alcohol remained (TLC, silica, 1:3 ethyl acetate—petroleum ether). The solution was transferred to a separatory funnel, diluted with ethyl acetate (300 mL) and washed with a mixture of 5% w/v aqueous sodium thiosulfate (300 mL) and 5% v/v saturated aqueous sodium bicarbonate (300 mL). The aqueous phase was separated and extracted with ethyl acetate (1×300 mL). The combined organic extracts were washed with water and brine, and dried ($MgSO_4$). Evaporation of the solvent and flash chromatography of the residue over silica gel (6.5×17.0 cm) with 1:3 ethyl acetate—petroleum ether gave 36 ($R_3 = SiPh_2Bu-t$) as a yellow-brown oil (12.310 g, 74%) suitable for the next stage. The material contains 11% of an isomer, but this impurity is removed in the next step. The isomer mixture had: IR (film) 1780–1720 cm$^{-1}$; $^1H$ NMR ($CDCl_3$, 200 MHz) δ 1.09 (s, 9H), 1.72 (q, 1H, J=14.5, 14.0 Hz), 1.85–2.10 (m, 2H), 2.40 (dt, 1H, J=14.0, 3.0 Hz), 3.22 (dd, 1H, J=10.5, 7.5 Hz), 3.40 (dd, 1H, J=10.5, 4.5 Hz), 3.72–4.00 (m, 2H), 4.35–4.50 (m, 1H), 4.63–4.80 (m, 1H), 7.36–7.52 (m, 6H), 6.60–6.72 (m, 4H); 13 NMR ($CDCl_3$, 75.47 MHz) (Major isomer only) δ 5.37 (t), 19.19 (s), 26.91 (q), 33.49 (t), 37.79 (t), 58.93 (t), 75.82 (d), 77.24 (d), 127.82 (d), 129.87 (d), 133.18 (s), 133.30 (s), 135.49 (d), 148.26 (s); mass (chemical ionization, NH$_3$) 524 (M+18). Anal. Calcd for C$_{23}$H$_{29}$IO$_4$Si: C, 52.67, H, 5.57; I, 24.20. Found: c, 52.64; H, 5.75; I, 24.18.

Compound 3

(R$_3$=SiPh$_2$Bu-t)

The iodocarbonate 36 (R$_3$=SiPh$_2$Bu-t) (14.25 g, 27.2 mmol) was dissolved in dry acetone (250 mL) containing p-toluenesulfonic acid monohydrate (3.200 g, 16.8 mmol). The solution was protected from atmospheric moisture by a drying tube packed with Drierite, and stirred for 91 h at room temperature (TLC control). Anhydrous triethylamine (3.5 mL, 25.1 mmol) was then added and stirring was continued for 10 min. The acetone was evaporated and the residual oil was dissolved in ethyl acetate (200 mL), washed successively with water (100 mL), saturated aqueous sodium bicarbonate (2×100 mL), brine (1×100 mL), and dried (MgSO$_4$). Evaporation of the solvent and flash chromatography of the residue over silica gel (6.5×17.0 cm) with 1:4 ether—petroleum ether gave compound 3 (R$_3$=SiPh$_2$Bu-t) (5.73 g, 39%). Further elution with 1:2 ethyl acetate—petroleum ether gave an unidentified product (1.22 g) and the corresponding desilylated compound (2.72 g), which was resilylated as follows:

"tert"-Butyldiphenylsilyl chloride (2.78 mL, 13.2 mmol) was injected over about 5 min to a cold (0° C.), stirred solution of the desilylated compound (2.67 g, 8.9 mmol), triethylamine (1.6 mL, 11.5 mmol), and DMAP (1.08 g, 8.8 mmol) in dichloromethane (10 mL). Stirring was continued for 2 h, during which time the mixture had attained room temperature. The mixture was diluted with dichloromethane (50 mL), washed with water (2×50 mL) and brine (100 mL), and dried (MgSO$_4$). Evaporation of the solvent and flash chromatography of the residue over silica gel (3.5×17.0 cm) using 1:4 ether—petroleum ether gave compound 3 (R$_3$=SiPh$_2$Bu-t) (4.09 g; 85%).

The combined yield from 36 (R$_3$=SiPh$_2$Bu-t) amounted to 9.82 g (67%). The iodoacetal 3 (R$_3$=SiPh$_2$Bu-t) had: [α]$_D^{28}$+0.468 (c 1.28, CHCl$_3$); $^1$H NMR (CDCl$_3$, 200 MHz) δ 1.05 (s, 9H), 0.95-1.18 (q, 1H, J=12.0 Hz), 1.40 (s, 3H), 1.43 (s, 3H), 1.65-1.80 (m, 3H), 3 07 (dq, 1H, J=10.0, 6.0 Hz), 3.15 (dq, 1H, J=10.0, 6.0 Hz), 3.65-3.75 (m, 1H), 3.80-3.95 (m, 2H), 4.05-4.20 (m, 1H), 7.35-7.50 (m, 6H), 7.65-7.72 (m, 4H); $^{13}$C NMR (CDCl$_3$, 75.47 MHz) δ 9.58 (t), 19.23 (s), 19.88 (q), 26.89 (q), 30.00 (q), 36.94 (t), 39.07 (t), 59.53 (t), 65.58 (d), 69.35 (d), 99.34 (s), 127.41 (d), 127.65 (d), 127.69 (d), 129.64 (d), 133 2 (s), 133.87 (s), 135.57 (d); exact mass, m/z 523.1166 [calcd for C$_{24}$H$_{32}$IO$_3$Si (M—CH$_3$)+, m/z 523.1164]. Anal. Calcd for C$_{25}$H$_{35}$IO$_3$Si: C, 55.76; H, 6.55; Si, 5.22. Found: C, 55.60; H, 6.76; Si, 5.22.

(S)-4-(Phenylmethyl)-2-oxazolidinone (19)

(a) (S)-Phenylalaninol

Dry THF (1.5 L) was distilled into a 3-L three-necked flask equipped with a mechanical stirrer, a reflux condenser closed by a septum carrying nitrogen inlet and exit needles, and a stopper. Lithium aluminum hydride (38 g, 1 mole) was added cautiously through the side neck over a period of 40 min. When hydrogen evolution had subsided, the mixture was refluxed with stirring for 30 min and then cooled to room temperature. Phenylalanine (100 g) was added in small portions to the stirred suspension. The mixture was refluxed overnight and cooled to room temperature. Celite (40 g) was poured into the reaction flask, the side neck stopper was replaced by a dropping funnel, and the mixture was cooled in an ice-bath. Water (40 mL) followed by 10% w/v aqueous sodium hydroxide (40 mL) were then added dropwise with stirring. Finally, water (120 mL) was added. The mixture was filtered on a sintered filter funnel and the solid was washed with ethyl acetate (2×200 mL). Insoluble material from the filtration was replaced in the original reaction vessel and stirred for 30 min with ethyl acetate (300 mL). The mixture was filtered, and the filtrate was combined with the first filtrate, concentrated to remove THF, and diluted with ethyl acetate to about 500 mL. The solution was washed with 10% w/v aqueous sodium hydroxide and the aqueous phase was extracted with ethyl acetate (1×200 mL). The combined organic extracts were dried (MgSO$_4$) and evaporated. The residual oil was dissolved in the minimum amount of refluxing ethyl acetate and the solution was allowed to cool to room temperature and then kept at 0° C. overnight. The first crop of product (57.2 g, after drying under oil-pump vacuum at room temperature) had mp 92°-94° C. [lit.$^1$ mp 92°-94° C.]. The mother liquor was evaporated and the residue was crystallized by the above procedure to furnish a second crop (5.2 g, after drying) with the same mp. The new mother liquor was processed in the same way to give a third crop (4.3 g) which was yellowish and was saved for chromatographic purification. The yield of pure (S)-phenylalaninol (crops 1 and 2) amounted to 62.4 g (68%).

$^1$Oeda, H. Bull Soc. Chem. Jpn. 1938, 13, 465.
$^2$Evans, D. A.; Weber, A. E. J. Am Chem. Soc. 1986, 108, 6757.

(b) The following experiment was done in a fume hood. Phosgene ("ca" 150 mL) in toluene (200 mL) was added dropwise over 1 h to a mechanically stirred mixture of (S)-phenylalaninol, prepared as described above, (79.1 g, 0.52 mol), toluene (900 mL), and aqueous sodium hydroxide (12.5% w/v, 1300 mL) that was cooled in an ice-bath. The reaction was monitored by TLC (silica, 1:19 methanol--chloroform) and found to be complete 30 min after the end of the addition. The cooling-bath was removed and the mixture was stirred overnight. The phases were separated and the aqueous layer was extracted with ethyl acetate (2×150 mL). The extracts and the toluene layer were combined, dried (MgSO$_4$), and evaporated to afford a solid residue. This material was dissolved in the minimum volume of boiling ethyl acetate, and hexane was added until the solution just became turbid. The solution was allowed to cool to room temperature and was then kept overnight in a refrigerator. Filtration afforded 19 as large, colorless crystals (80 g, 86%): mp 87°-89° C. (lit.$^2$ 87°-88.5° C.).

Compound 20

(Chart 2)

n-Butyllithium 1.65M in hexanes, ca 180 mL) was transferred by cannula to an addition funnel and added over 30 min to a cold (−78° C.), magnetically stirred solution of the oxazolidinone 19 (53.19 g, 0.3 mol) in THF (500 mL) containing 2.2'-dipyridyl (ca 20mg). When all the butyllithium had been added, the initially yellow solution turned brick-red. Stirring was continued for 30 min and freshly distilled crotonyl chloride (29 mL, 0.3 mol) in THF (200 mL) was added dropwise from a dropping funnel. Stirring at −78° C. was continued for 30 min. At this stage no starting oxazolidinone remained (TLC, silica, 1:1 ethyl acetate—hexane). The cooling-bath was removed and the mixture was left for 1 h, and then most of the THF was evaporated at room temperature. Ether (ca 1 L) was added, followed by saturated aqueous ammonium chloride solution (400 mL) and water (500 mL). The whole mixture was transferred to a separatory funnel and the layers were separated. The organic phase was washed with 5% w/v aqueous sodium hydroxide (400 mL). The combined aqueous phases were extracted with ethyl acetate (2×400 mL). All the organic extracts were combined, dried ($Na_2SO_4$), and evaporated. The solid residue was dissolved in the minimum volume of boiling ether. The solution was allowed to cool to room temperature and the first crop of crystals (52.83 g) was collected: mp 84°–86° C. The filtrate was evaporated and the residue was dissolved in the minimum volume of boiling ether. The solution was allowed to cool to room temperature and was then kept overnight in a refrigerator. A second crop (12.84 g) of product was collected. The experiment was repeated on the same scale. The first crop (48.10 g) had: mp 84°–86° C. A second crop (9.96 g) was also collected. A third experiment was carried out using the oxazolidinone 19 (47.14 g, 0.27 mol). The first crop (47.97 g) had: mp 84°–86° C. A second crop (9.65 g) was again obtained. The second crops from all three experiments were combined and recrystallized from the minimum volume of boiling ether, the solution being allowed to cool to room temperature. This procedure afforded the product 20 (20.84 q): mp 85°–86 C. The total yield amounted to 169.84 g (80%): $^1H$ NMR ($CDCl_3$, 200 MHz) $\delta$ 2.0 (d, 3H, J=5.2 Hz), 2.82 (dd, 1H, J=12.8, 9.6 Hz), 3.35 (dd, 1H, J=12.8, 3.6 Hz), 4.10–4.30 (m, 2H), 4.68–4.83 (m, 1H), 7.20–7.45 (m, 7H); $^{13}C$ NMR ($CDCl_3$, 75.47 MHz) $\delta$ 18.45 (q), 37.89 (t), 55.27 (d), 66.11 (t), 121.89 (d), 127.30 (d), 128.94 (d), 129.46 (d), 135.40 (s), 146.92 (d), 153.44 (s), 164.96 (s).

Compound 21

(Chart 2)

This experiment was done in a fume hood. A dry 3 L three-necked flask, which had been marked at the 1.6 L level, and containing a magnetic stirring bar, was capped with two septa, one of which carried inlet and exit needles for argon. The central neck was fitted with a special condenser that consisted of a glass tube wound in a spiral and contained in a cup packed with dry-ice acetone. Butadiene, dried by passage through Drierite (1.8×16.0 cm), was led into the spiral tube, where it condensed and eventually collected in the flask, which was also cooled to −78° C. When 1.6 L of liquid butadiene had been collected, a solution of the oxazolidinone 20 (84.0 g, 342 mmol) in dry dichloromethane (500 mL) was added by cannula to the stirred olefin, and then diethylaluminum chloride (1.8M in toluene, 600 mL, 1.08 mol) was transferred to the reaction vessel. The special condenser was replaced by a drying tube packed with Drierite and the inlet and exit needles for argon were removed. The reaction mixture was stirred for about 16 h at −7° C. to −10° C., this temperature being maintained by an alcohol-bath with an immersion cooler. A few drops of the reaction mixture were quenched with dilute hydrochloric acid and extracted with ethyl acetate. The organic solution was examined by TLC (silica, 1:4 ethyl acetate—petroleum ether). No starting material remained. Dilute hydrochloric acid (1N) was added slowly by dropper with magnetic stirring and cooling (bath temperature −40° C. to −70° C.) until the lower aqueous layer was acidic. The solution changes from yellow to colorless at this stage, but more hydrochloric acid was added until the aqueous phase was at pH 2. The reaction mixture was then poured into a 5 L beaker and stirred for 2 h. The resulting white emulsion was filtered by suction through a Whatman No. 2 paper. The organic layer was separated and the aqueous phase was extracted with ethyl acetate (3×300 mL). The combined organic solutions were washed with water (2×200 mL) and brine (1×250 mL), dried ($Na_2SO_4$), and evaporated. Flash chromatography of the resulting yellow oil over silica gel (10×20 cm) with 1:4 ethyl acetate—petroleum ether and crystallization from hot 95% ethanol gave 21 (57.80 g, 56%): mp 81°–83° C.; $[\alpha]_D^{20}$ +149.416 (c 1.57, $CDCl_3$); $^1H$ NMR ($CDCl_3$, 200 MHz) $\delta$ 0.98 (d, 3H, J=6Hz), 1.65–2.50 (m, 5H), 2.8 (dd, 1H, J=13.5, 9.5 Hz), 3.27 (dd, 1H, J=13.5, 3.0 Hz), 3.7 (dt, 1H, J=10.0, 5.5 Hz), 4.10–4.22 (m, 2H), 4.62–4.80 (m, 1H). 5.71 (m. 2H), 7.26–7.40 (m, 5H); $^{13}C$ NMR ($CDCl_3$, 75.47 MHz) $\delta$ 19.52 (q), 29.02 (t), 30.32 (d), 32.97 (t), 37.86 (t), 44.17 (d), 55.24 (d), 65.96 (t), 124.66 (d), 126.34 (d), 127.30 (d), 128.87 (d), 129.42 (d), 135.25 (s), 153.06 (s), 176.39 (s); exact mass, m/z 299.1521 (calcd for $C_{18}H_{21}NO_3$, m/z 299.1521). Anal. Calcd for $C_{18}H_{21}NO_3$, C, 72.22; H, 7.07; N, 4.68. Found: C, 72.16; H, 6.98; N, 4.52.

Compound 22

(R=$CH_2Ph$)

(Chart 2)

n-Butyllithium (1.6M in hexanes, ca 81 mL) was added dropwise at 0° C. to a stirred solution of freshly distilled benzyl alcohol (13.1 mL, 127 mmoL) and 2,2'-dipyridyl (10 mg) in THF (200 mL). At the end of the addition the mixture turned brick-red. The solution was stirred for 20 min and then oxazolidinone 21 (32.06 g, 107 mmol) in THF (200 mL) was added dropwise at 0° C. The resulting pale yellow solution was stirred at 0° C. for 5 h (TLC control) and saturated aqueous ammonium chloride (200 mL) was then added. The THF was evaporated at room temperature and the aqueous residue was extracted with ethyl acetate (3×200 mL). The combined organic extracts were washed with water (1×100 mL) and brine (1×100 mL), and dried ($Na_2SO_4$). Evaporation of the solvent at room temperature afforded a light-yellow oil, which was mixed with petroleum ether (bp 30°–60° C., 200 mL) and stirred for 15 min. The colorless, crystalline oxazolidinone 19 was filtered off and washed with petroleum ether (2×50 mL). After being dried, the material weighed 15.90 g (84%). The petroleum ether solutions were combined and evaporated. Flash chromatography of the resulting yellow oil over silica gel (10×23 cm) with 1:4 ethyl acetate—petroleum ether gave 22 (R=$CH_2Ph$) (21.50 g, 86%): bp 113°–115° C. (0.5 mm); $[\alpha]^{21}D$ +68.39 (c 2.8, $CDCl_3$), IR (film) 1734 $cm^{-1}$; $^1H$ NMR ($CDCl_3$, 200 MHz) $\delta$ 0.94 (d, 3H), J=6.4 Hz), 1.60–2.42 (m, 6H), 5.16 (s, 2H), 5.66 (m, 2H), 7.30–7.42 (m, 5H); $^{13}C$ NMR ($CDCl_3$, 75.47 MHz) $\delta$ 19.73 (q), 28.59 (t), 30.66 (d), 33.10 (t), 46.99 (d), 65.99 (t), 124.73 (d), 126 26 (d), 128.13 (d), 128.51 (d), 136.17 (s), 175.77 (s); exact mass, m/z 230.1303 (Calcd for $C_{15}H_{18}O_2$, m/z 230.1306). Anal. Calcd for $C_{15}H_{18}O_2$: C, 78.23; H, 7.88. Found: C, 78.44; H, 7.82.

In subsequent runs the material was distilled after flash chromatography and the data quoted are for distilled material, which was obtained in 81% yield.

Compound 23

(R=Me)

(Chart 2)

Dry methanol (160 mL) was placed in a 1 L three-necked flask containing a magnetic stirring bar and fitted with a pressure-equalizing funnel. The flask was closed with septa and fitted with inlet and exit needles for argon. It was then cooled in an acetone-dry ice bath and n-butyllithium (1.6M in hexanes, 270 mL, 433 mmol) was added dropwise from the funnel, with stirring. The resulting solution of lithium methoxide was stirred for 15 min and the cooling-bath was removed. When the solution had attained room temperature, the benzyl ester 22 (R=CH$_2$Ph) (50.0 g, 217 mmol) in dry dichloromethane (200 mL) was added via cannula over about 15 min. Stirring at room temperature was continued for 30 min, the mixture was refluxed gently for 46 h, and cooled to room temperature. Saturated aqueous ammonium chloride (200 mL) was then added with vigorous stirring, and stirring was continued for 10 min. The layers were separated and the aqueous phase was extracted with dichloromethane (2×100 mL). The combined organic extracts were washed with water (2×100 mL) and brine (1×100 mL), and dried (Na$_2$SO$_4$). The solvent was evaporated at 1 atm through a short Vigreaux column. Flash chromatography of the yellow oily residue over silica gel (10×20 cm) with 1:9 ether—petroleum ether and evaporation of appropriate (TLC) fractions at 1 atm followed by distillation (water pump) gave 23 (R=Me) (29.15 g, 87%): bp 76°-80° C. (30 mm). The $^1$H NMR spectrum (CDCl$_3$, 400 MHz) indicated (d at $\delta$ 0.92 and at $\delta$ 0.95) that some (less than 12%) epimerization had occurred at C(1).

Compounds 24 and 25

(Chart 2)

n-Butyllithium (1.6M in hexanes, 158.4 mL, 253 mmol) was added dropwise from a dropping funnel to a stirred, cold (0° C.) solution of diisopropylamine (34.86 mL, 25.17 g, 249 mmol) in THF (200 mL). The solution was stirred at 0° C. for 20 min and was then cooled to −78° C. Trans ester 23 (R=Me) (36.54 g, 236 mmol) in THF (100 mL) was then added dropwise by cannula over about 10 min, and stirring at −78° C. was continued for 45 min. The reaction was then quenched at −78° C. by dropwise addition of glacial acetic acid (20.1 mL, 351 mmol) in THF (100 mL) and stirring was continued for 15 min. The cooling-bath was removed and the mixture was allowed to attain room temperature (ca 0.5 h). The mixture was diluted with water (100 mL) and extracted with ethyl acetate (1×150 mL; 2×100 mL). The combined organic phases were washed successively with water (1×150 mL), 1N hydrochloric acid (2×120 mL), water (1×100 mL), and saturated aqueous sodium bicarbonate (1×100 mL), and dried (Na$_2$SO$_4$). The solvent was removed by distillation at 1 atm through a Vigreaux column and distillation of the residue under water-pump vacuum gave 25 and 23 (R=Me) (32.88 g, 90%) as a 65:35::cis:trans mixture (V.P.C., 20% Carbowax 20M, 6 ft., 110° C.). The mixture was separated by spinning band distillation [Perkin Elmer 251 Auto Annular Still] under water-pump vacuum: the trans isomer 23 (R=Me) has bp 60° C. (14 mm) and the cis compound 25 has bp 63° C. (14 mm). From 39.620 g of isomer mixture, 23.227 g of cis compound 25 was obtained.

Compound 26

(Chart 2)

This compound was made from D-glucal[1] and also by the following route: The cis ester 25 (10.00 g, 64.9 mmol) in dry THF (10 mL) was added via cannula to a magnetically stirred and cooled (ice-bath) suspension of lithium aluminum hydride (2.96 g, 77.9 mmol) in THF (60 mL). A further portion of solvent (10 mL) was used as a rinse. The addition took about 10 min. The mixture was refluxed for 15 h, cooled to room temperature and then in an ice-salt bath. Ethyl acetate (15 mL) was added dropwise, the mixture was stirred for 15 min and aqueous sodium hydroxide (3M, ca 20 mL) was added until all precipitated aluminum salts had dissolved. Water (10 mL) was added and the organic layer was separated. The aqueous phase was extracted with ethyl acetate (2×50 mL) and the combined organic layers were washed with water (20 mL) and brine (20 mL), and dried (MgSO$_4$). Evaporation of the solvent and distillation (water-pump) gave 26 (9.60, 96%) bp 120°-122° C.(37 mm); [α]$_D^{26}$ −25.58 (c 0.995, CHCl$_3$ (lit.[1] [α]hd D$^{25}$ = −23.84 (c 2.2, CHCl$_3$); $^1$H NMR (CDCl$_3$, 200 MHz) $\delta$ 0.90 (d, 3H, J=7.0 Hz), 1.55 (br s, 1H, disappears on treatment with D$_2$O, OH), 1.65-2.30 (m, 6H), 3.45-3.70 (m, 2H), 5.62 (m, 2H).

[1]Prasad, J. Siva; Clive, D. L. J.; da Silva, G. V. J., *J. Org. Chem.* 1986, 51, 2717.

Compound 27

(Chart 2)

(a) "p"-Toluenesulfonyl chloride, freshly crystallized from petroleum ether, (7.900 g, 42 mmol) was added in one portion to a stirred solution of the alcohol 26 (5.000 g, 39 mmol) in dry dichloromethane (125 mL) containing dry pyridine (10 mL). 4-(Dimethylamino)pyridine (125 mg, 1.00 mmol) was tipped into the solution and stirring at room temperature was continued for 24 h under argon. At this stage no starting alcohol remained (TLC control). The mixture was quenched by addition of ice-cold water (250 mL) and extracted with dichloromethane (2×100 mL). The combined organic extracts were washed with 20% v/v hydrochloric acid (3×70 mL) and then with water, until the aqueous phase was neutral (pH paper). The organic solution was dried (Na$_2$SO$_4$) and evaporated below 40° C. Flash chromatography of the residue over silica gel (6.5×17.0 cm) using 1:4 ethyl acetate—hexane gave the p.toluenesulfonate derivative (10.00 g, 91%) as a thick, colorless, homogeneous (TLC, silica, 1:9 ethyl acetate—hexane) liquid: [α]$_D^{25}$ −16.3 (c 9.9, CHCl$_3$), IR (film) 1650, 1600, 1360, 1190, 1175, 1100, 1019, 960, 840, 815, 665 cm$^{-1}$; $^1$H NMR (CDCl$_3$, 200 MHz) $\delta$ 0.78 (d, J=7 Hz, 3H), 1.60-2.24 (m, 6H), 2.46 (s, 3H), 3.94 (m, 2H), 5.56 (m, 2H), 7.38 (d, J=9Hz, 2H), 7.81 (d, J=9Hz, 2H); exact mass, m/z 108.0940 (calcd for C$_8$H$_{12}$ (M—C$_7$H$_8$SO$_3$), m/z 108.0940).

(b) The above tosylate (10.00 g, 35 mmol) in dry DMSO (10 mL) was added dropwise over about 10 min to a stirred and warmed (60° C.) suspension of sodium cyanide (2.16 g, 44 mmol) in DMSO (20 mL). After the addition, stirring was continued for 10 h at 75° C., at which stage no starting material remained (TLC control). The reaction mixture was cooled, diluted with water (400 mL) and extracted with ethyl acetate (5×100 mL). The combined organic extracts were washed with brine (2×100 mL), dried ($Na_2SO_4$), and evaporated. Kugelrohr distillation of the residue gave the corresponding nitrile (4.44 g, 92%) as a homogeneous (TLC, silica, 1:9 ethyl acetate—hexane), colorless oil: bp 65°-70° C. (0.4 mm); $(\alpha)_D^{25}$ −18.64 (c 3.5, $CHCl_3$); IR (film) 2222 cm$^{-1}$; $^1$H NMR ($CDCl_3$, 200 MHz) δ 0.91 (d, J=7 Hz, 3H), 1.64-2.36 (m, 8H), 5.62 (m, 2H); $^{13}$C NMR ($CDCl_3$, 50.32 MHz) δ 14.76 (q), 18.49 (t), 28.14 (t), 29.42 (d), 31.12 (t), 34.32 (d), 119.11 (s), 123.79 (d), 125.34 (d) exact mass, m/z 135.1032 (calcd for $C_9H_{13}N$, m/z 135.1147).

(c) A mixture of the above nitrile (8.00 g, 60 mmol) and aqueous sodium hydroxide [from sodium hydroxide (16 g) and water (100 mL)] was stirred and refluxed under argon for 24 h. The solution was cooled and extracted with ether (3×30 mL). The aqueous portion was cooled in an ice-bath, acidified by slow addition of concentrated hydrochloric acid, and extracted with ethyl acetate (3×50 mL). The combined organic extracts were washed with water (2×50 mL), dried ($Na_2SO_4$), and evaporated. Kugelrohr distillation of the residual colorless liquid gave 27 (8.40 g, 92%) as a homogeneous (TLC, silica, 3:7 ethyl acetate—hexane) oil: bp 105°-110° C. (0.4 mm); $[\alpha]^{25}D$ −8.5 (c 4.15, $CHCl_3$); IR (film) 3500-2300, 1700, 660 cm$^{-1}$; $^1$H NMR ($CDCl_3$, 200 MHz) δ 0.92 (d, J=7 Hz, 3H), 1.66-2.40 (m, 8H), 5.62 (m, 2H); $^{13}$C NMR ($CDCl_3$, 100.61 MHz) δ 15.16 (q), 28.76 (t), 30.12 (d), 31.85 (t), 33.69 (d), 35.75 (t), 124.82 (d), 125.50 (d), 180.37 (s); exact mass, m/z 154.1002 (calcd for $C_9H_{14}O_2$, m/z 154.0993).

Compound 2 of Chart 2

(corresponding to compound 2 with $R_2$ =Me, of Chart 1)

(a) Sodium iodide, dried at 100° C. for 12 h, (15 g, 100 mmol) and 18-crown-6 (540 mg, 2 mmol) were added to a vigorously mechanically-stirred solution of the acid 27 (3.00 g, 19 mmol) in dry dichloromethane. After 15 min the reaction mixture was cooled in an ice-salt bath and m-chloroperbenzoic acid (89%, 5.47 g, 28 mmol) in dichloromethane (100 mL) was added at a fast dropwise rate over about 15 min. The mixture became thick and dark brown in color. Vigorous stirring was maintained throughout the addition and for 1 h more. The mixture was then diluted with dichloromethane (100 mL), washed successively with 10% w/v aqueous sodium thiosulfate (3×60 mL), saturated aqueous sodium bicarbonate (3×50 mL), and water (2×50 mL), and dried ($Na_2SO_4$). Evaporation of the solvent and flash chromatography of the residue over silica gel (6.5×17.0 cm) using 3:7 ethyl acetate—hexane gave material that was dissolved in the minimum volume of hot ethyl acetate. The solution was diluted with hexane until just turbid and allowed to cool to room temperature. It was then kept overnight in a refrigerator to afford pure (TLC, silica, 1:3 ethyl acetate—hexane) intermediate iodolactone (5.00 g, 90%) as white needles: mp 70°-71° C., $[\alpha]^{25}D$ +27.65 (c 5.6, $CHCl_3$); FTIR (cast from dichloromethane) 1738 cm$^{-1}$; $^1$H NMR ($CDCl_3$, 200 MHz) δ 0.99 (d, J=6.8 HZ, 3H), 1.59 (ddd, J=16.0, 12.5, 4.5 Hz, 1H), 1.89 (br d, J=16 Hz, 1H), 1.95-2.10 (m, 2H), 2.11-2.35 (m, 2H), 2.57 (m, 2H), 2.68 (br d, J=15 Hz, 1H, ), 4.60 (br s, 1H), 4.79 (br s, 1H; $^{13}$C NMR ($CDCl_3$, 75.49 MHz) δ 18.70 (q), 26.75 (t), 27.62.(d), 30.03 (d), 30.61 (t), 31.57 (d), 33.88 (t), 77.75 (d), 170.32 (s); exact mass, m/z 279.9954 (calcd for $C_9H_{13}O_2I$, m/z 279.9960).

(b) The above iodolactone (3.5 g, 13 mmol) was dissolved in toluene (25 mL) and 1,5-diazabicyclo-[5.4.0]undec-5-ene (4.76 g, 30 mmol) was added. The mixture was refluxed for 2 h under argon. It was then cooled and diluted with ethyl acetate (250 mL). The solution was washed successively with water (25 mL), 10% v/v aqueous hydrochloric acid (3×50 mL), water (50 mL), 10% w/v aqueous sodium thiosulfate (2×50 mL), and water (3×50 mL), and dried ($Na_2SO_4$). Evaporation of the solvent below 45° C. (water-pump) gave material which was dissolved in the minimum volume of hot ethyl acetate. The solution was diluted with hexane till just turbid and then cooled, first to room temperature and then in a refrigerator. This procedure afforded compound 2 (Chart 2) as shining plates. Several reactions on about the same scale were carried out until 23.00 g of starting iodide had been processed to afford compound 2 (Chart 2) (9.90 g, 79%): mp 76°-77° C.; $[\alpha]^{24}D$ −246.35 (c 1.275, $CHCl_3$); FTIR (cast from dichloromethane) 1724 cm$^{-1}$; $^1$H NMR ($CDCl_3$, 200 MHz)) δ 1.08 (d, J=7.6 Hz, 3H), 1.86-2.05 (m, 1H), 2.15-2.30 (m, 2H), 2.42-2.60 (m, 3H), 4.70 (m, 1H), 5.70 (dt, J=1.6, 10 Hz, 1H), 5.96 (m, 1H); $^{13}$C NMR ($CDCl_3$, 75.49 MHz) δ 17.77 (q), 29.80 (t), 29.99 (d), 30.18 (t), 35.34 (d), 69.87 (d), 125.32 (d), 136.13 (d), 171.94 (s); exact mass, m/z 152.0842 (calcd for $C_9H_{12}O_2$, m/z 152.0837).

Compound 4

(Chart 1, $R_2$=Me, $R_3$=Siph$_2$Bu-t)

Lithium diisopropylamide was prepared by dropwise addition of n-butyllithium (1.55M in hexanes, 12.80 mL, 19.84 mmol) over 10 min to a stirred and cooled (ice-bath) solution of diisopropylamine (2.87 mL, 20.47 mmol) in THF (25.5 mL). The solution was cooled to −78° C. and the lactone 2 ($R_2$=Me) (1.520 g, 9.99 mmol) in THF (8.50 mL plus 8.50 mL as a rinse) was added dropwise over about 10 min. The mixture was stirred at −78° C. for 1.25 h and then the iodide 3 ($R_3$=SiPh$_2$Bu-t) (5.380 q, 9.99 mmol) in a mixture of THF (16 mL) and HMPA (13.5 mL) was added by cannula over about 15 min, more THF (8 mL) being used as a rinse. Stirring was continued overnight, the cooling-bath being left in place but being allowed to attain room temperature. The mixture was then cooled to −78° C. and saturated aqueous ammonium chloride (11 mL) was added. The mixture was diluted with ethyl acetate (80 mL), washed with water (40 mL) and brine (40 mL), and dried ($Na_2SO_4$). Evaporation of the solvent below 30° C. and flash chromatography of the residue over silica gel (3.5×17.0 cm) with 1:4 ethyl acetate—petroleum ether gave 4 ($R_2$=Me, $R_3$=SiPh$_2$Bu-t) (1.980 g, 35%) as Well as lactone 2 ($R_2$=Me) (0.83 g). The coupled product 4 ($R_2$=Me, $R_3$=SiPh$_2$Bu-t) (77% yield after correction for recovered 2 ($R_2$=Me) had: $[\alpha]_D^{28}$ −47.9 (c 1.00, $CHCl_3$); IR (film) 1722, 1585 cm$^{-1}$; $^1$H NMR ($CDCl_3$, 400 MHz) δ 1.06 (s, 9H), 1.12 (d, 3H, J=7.5 Hz), 1.08-1.15 (m, 1H), 1.31 (s, 3H), 1.12 (s, 3H). 1.45 (dt, 1H, J=13.0, 2.5, 2.5 Hz), 1.56 (ddd, 1H, J=14.5, 10.0, 4.8 Hz), 1.60-1.75 (m, 2H), 1.85 (dt, 1H, J=13.5, 2.0, 2.0 Hz), 1.95 (ddd, 1H, J=14.5, 7.6, 2.8 Hz), 2.10 (bs, 1H), 2.19-2.25 (m, 1H), 2.48-2.58 (m, 1H), 2.70 (bt, 1H, J=5.8 Hz), 3.65-3.72 (m, 1H), 3.80-3.90 (m, 1H), 4.10-4.22 (m, 2H), 4.69-4.73 (m, 1H), 5.72 (dt, 1H, J=9.5, 1.5, 1.5 Hz), 5.94-6.00 (m, 1H), 7.35–7.45 (m, 6H,), 7.65–7.70 (m, 4H); $^{13}C$ NMR (CDCl$_3$, 100.62 MHz) δ 17.34 (q), 19.15 (s), 19.90 (q), 26.82 (q), 29.59 (t) 30.14 (q), 36.53 (d) 36.70 (d), 37.27 (d), 37.55 (t), 39.30 (t), 42.06 (t), 59.56 (t), 65.50 (d), 68.27 (d), 70.20 (d), 98.50 (s), 125.21 (d), 127.56 (d), 129.51 (d), 133.89 (s), 135.51 (d), 136.87 (d), 175.74 (s); exact mass, m/Z 547.2870 [calcd for C$_{33}$H$_{43}$O$_5$Si (M—CH$_3$)+, m/z 547.2879]. Anal. Calcd for C$_{34}$H$_{45}$O$_5$Si: C, 72.56; H, 8.24; Si, 4.99. Found: C, 72.36; H, 8.48; Si, 4.84.

Compound 5

Chart 1, R$_2$=Me, R$_3$=SiPh$_2$Bu-t)

(a) Diisobutylaluminum hydride (1M in dichloromethane, 2.0 mL, 2 0 mmol) was injected over about 5 min into a stirred, cold (−78° C.) solution of lactone 4 (R$_2$=Me, R$_3$=SiPh$_2$Bu-t) (797.5 mg, 1.41 mmol) in dichloromethane (8 mL). Stirring at −78° C. was continued for 1.5 h, saturated aqueous ammonium chloride (3 mL) was added, the cold-bath was removed, and the reaction mixture was left for 1 h to warm to room temperature. The mixture was diluted with dichloromethane (100 mL) and filtered through a pad of Celite (4.0×4.0 cm). The filtrate was washed with brine and dried (MgSO$_4$). Evaporation of the solvent below 30° C. and flash chromatography of the residue over silica gel (3.0×12.0 cm) with 1:3 ethyl acetate—petroleum ether gave the corresponding lactol (720 mg, 90%): IR (film) 3500–3250, 1720, 1590 cm$^{-1}$; $^1H$ NMR (CDCl$_3$, 400 MHz) δ 1.05 (s, 9H), 1.08 (d, 3 H, J=7.5 Hz,), 1.05–1.20 (m, 1H), 1.35 (s, 3H), 1.30–1.47 (m, 2H), 1.41 (s, 3H) , 1.65–1.85 (m, 5H), 1.96–2.05 (m, 1H), 2.09–2.29 (m, 2H). 2.45–2.60 (m, 1H), 3.65–3.75 (m, 1H), 3.80–3.90 (m, 2H), 4.05–4.61 (m, 1H), 5.72–5.85 (m, 2H), 7.35–7.50 (m, 6H), 7.65–7.75 (m, 4H); exact mass, m/z 531.2915 [calcd for C$_{33}$H$_{43}$O$_4$Si (M—H$_2$O—CH$_3$)$^+$], m/z 531.2931.

(b) Manganese dioxide (Aldrich, manganese(IV)oxide, activated, #21,764-6, 2.874 g, 33.06 mmol) and anhydrous sodium acetate (203.3 mg, 2.48 mmol) were added to a stirred solution of the above lactol (934.0 mg, 1.65 mmol) in dry chloroform (16 mL). Stirring at room temperature, and under argon, was continued for 74.5 h, further reagents and solvent being added as follows: Manganese dioxide (2.882 g), sodium acetate (208 mg), and chloroform (2 mL) after 25 h; manganese dioxide (2.878 g) and sodium acetate (215 mg) after 50 h; manganese dioxide (2.882 g), sodium acetate (209 mg), and chloroform (2 mL) after 69 h. At the end of the specified period the mixture was filtered through a pad of Celite and the solids were washed well with dichloromethane. The combined solvents were evaporated (30° C.) and flash chromatography of the residue over silica gel (3.5×17.0 cm) with 1:49 methanol—dichloromethane gave 5 (R$_2$=Me, R$_3$=SiPh$_2$Bu-t) (730.7 mg, 78%) as a thick oil: IR (film) 1720, 1680, 1590 cm$^{-1}$; $^1H$ NMR (CDCl$_3$, 400 MHz) δ 1.05 (s, 9H), 1.09 (d, 3H, J =7.0 Hz), 1.19 (q, 1H, J =11.6 Hz), 1.38 (s, 3H), 1.38–1.41 (m, 1H), 1.40 (s, 3H), 1.65–1.80 (m, 4H), 2.32 (dd, 1H, J=12.0, 4.0 Hz), 2.40 (t, 1H, J=11.8 Hz), 2.45–2.54 (m, 1H), 2.60–2.72 (m, 2H), 3.65–3.90 (m, 3H), 4.05–4.15 (m, 1H), 6.0 (d, 1H, J=10.0 Hz), 7.02 (dd, 1H, J=10.0, 6.0 Hz), 7.35–7.49 (m, 6H), 7.65–7.72 (m, 4H), 9.60 (d, 1H, J=3.8 Hz); $^{13}C$ NMR (CDCl$_3$, 75.47 MHz) δ 11.72 (q), 19.21 (s), 19.70 (q), 26.86 (q), 30.05 (q), 30.90 (d), 33.46(t), 36.64 (d), 37.32 (t), 37.63 (d), 39.23 (t), 49.52 (d), 59.53 (t), 65.43 (d), 65.86 (d), 98.76 (s), 127.62 (d), 127.65 (d), 128.09 (d), 129.61 (d), 133.84 (s), 133.91 (s), 135.56 (d), 155.19 (d), 198.09 (s), 203.66 (d); exact mass, m/z 547.2880 [calcd for C$_{34}$H$_{43}$O$_5$Si (M—CH$_3$)$^+$91 , m/z 547.2880]. Anal. Calcd for C$_{34}$H$_{46}$O$_5$Si: C, 72.58;H, 8.24. Found: C, 72.55; H, 8.20.

Compound 6

(R$_2$=Me, R$_3$=SiPh$_2$Bu-t).

The enone-aldehyde 5 (R$_2$=Me, R$_3$=SiPh$_2$Bu-t) (871 mg, 1.548 mmol) was dissolved in a mixture of dry toluene (16 mL) and dry benzonitrile (2 mL). Freshly prepared Wilkinson's catalyst (1.43 g, 1.546 mmol) was added and the mixture was refluxed under argon, the progress of the reaction being closely followed by TLC (1:4 ethyl acetate—petroleum ether). When the starting material had disappeared (2.5 h), the mixture was cooled to room temperature and then to −10° C. (ice-methanol bath). The precipitated rhodium complex was filtered off through a pad of Florisil (4×4 cm) and washed with ethyl acetate. The combined filtrates were concentrated. Flash chromatography of the residue over silica gel (3.0×17.0 cm) using first 1:4 ether—petroleum ether to remove triphenylphosphine and benzonitrile, and then 1:4 ethyl acetate—petroleum ether gave a crude product (731.1 mg). Two other portions of enone-aldehyde 5 (R$_2$=Me, R$_3$=SiPh$_2$Bu-t) (300 mg and 505 mg) were processed in the same way to afford a crude product (708.9 mg). The combined crude products (1.440 g) from all three experiments were purified using a Waters Prep LC System 500A instrument with two PrepPak-500/Silica cartridges and 2.5% v/v acetone—dichloromethane as eluent. A refractive index detector and flow rate of 100 mL min$^{-1}$ were used. The crude product mixture (1.440 g) was dissolved in 50 mL of dichloromethane and 20 mL-injections were made. This procedure gave the desired enone 6 (R$_2$=Me, R$_3$=SiPh$_2$Bu-t) (800 mg, 50%): [α]$_D^{27}$+51.96 (c 1.40, CHCl$_3$); IR (film) 1680, 1620, 1590 cm$^{-1}$; $^1H$ NMR (CDCl$_3$, 400 MHz) δ 1.0 (d, 3H, J =7.0 Hz), 1.05 (s, 9H), 1.10 (q, 1H, J =12.0 Hz), 1.22–1.31 (m, 1H), 1.35 (s, 3H) , 1.42 (s, 3H), 1.32–1.55 (m, 4H), 1.65–1.72 (m, 2H) , 2.05–2.15 (m, 1H), 2.25 (t, 1H, J=16.5 Hz), 2.32 (dd, 1H, J=16.5, 5.5 Hz), 2.50–2.59 (m, 1H), 3.65–3.85 (m, 3H). 4.07–4.15 (m, 1H), 5.94 (d, 1H, J=10 Hz), 5.95 (dd, 1H, J=10.0, 5.0 Hz), 7.35–7.42 (m. 6H), 7.65–7.70 (m, 4H); $^{13}C$ NMR (CDCl$_3$, 75.47 MHz) δ 12.11 (q), 19.20 (s), 19.83 (q), 26.85 (q), 27.44 (t), 30.26 (q), 33.05 (d), 33.57 (t), 37.21 (t), 37.37 (d), 39.31 (t), 39.86 (t), 59.65 (t), 65.63 (d), 68.99 (d), 98.44 (s), 127.59 (d), 127.61 (d), 128.10 (d), 129.57 (d), 133.86 (s), 133.91 (s), 135.53 (d), 155.92 (d), 199.82 (s); exact mass, m/z 519.2944 [calcd for C$_{32}$H$_{43}$O$_4$Si (M—CH$_3$)$^+$, m/z 519.2930]. Anal. Calcd for C$_{33}$H$_{46}$O$_4$Si: C, 74.13; H, 8.67. Found: C, 74.18; H, 8.72.

Compound 7

(R$_1$=H, R$_2$=Me, R$_3$=Siph$_2$Bu-t, R$_4$=H).

n-Butyllithium (1.6M in hexanes, 0.541 mL, 0.865 mmol) was added dropwise to a stirred and cooled (ice-bath) solution of diisopropylamine (0.121 mL, 0.865 mmol) in dry ether (3.5 mL). Stirring at 0° C. was continued for 20 min and the solution was then cooled to −78° C. The enone 6 (R$_2$=Me, R$_3$=SiPh$_2$Bu-t) (355.6 mg, 0.665 mmol) in ether (1.5 mL plus 1.5 mL as a rinse) was added by cannula over about 10 min. Stirring at −78° C. was continued for 1 h and then 4-penten-1-al[1] (0.336 mL, 3.99 mmol) in ether (1.5 mL plus 1.5 mL as a rinse) was added also by cannula over about 5 min. After a further 10 min, glacial acetic acid (0.227 mL, 3.99 mmol) was injected, the cold-bath was removed and, after 1 h, ether (20 mL) and water (15 mL) were added with stirring. The aqueous layer was separated and the organic extract was washed with saturated sodium bicarbonate (2×10 mL) and brine (1×10 mL). All the aqueous phases, including the original ne from the quenched reaction mixture, were extracted with ether (10 mL). The combined ether extracts were dried (MgSO$_4$) and evaporated. Flash chromatography of the residue over silica gel (3.0×17.0 cm) with 1:4 ethyl acetate—petroleum ether gave the aldols 7 ($R_1$=H, $R_2$=Me, $R_3$=SiPh$_2$Bu-t, $R_4$=H) (311.3 mg, 75%): IR (film) 3350-3600, 1675, 1590 cm$^{-1}$; $^1$H NMR (CDCl$_3$, 400 MHz) δ 1.05 (s, 9H), 1.08-1.13 (m, 1H), 1.13 (d, 3H, J=7.5 Hz), 1.30-1.45 (m, 4H), 1.36 (s, 3H), 1.40 (s, 3H), 1.55-1.80 (m, 5H), 2.15 (d, 1H, J=6.5 Hz, OH, disappears on deuteration), 2.10-2.35 (m, 3H), 2.37 (t, 1H, J=6.0 Hz), 2.72-2.80 (m, 1H), 3.67-3.78 (m,2H), 3.80-3.95 (m, 2H), 4.05-4.12 (m, 1H), 4.95-5.09 (m, 2H), 5.80-5.90 (m, 1H), 5.95 (dd, 1H, J=10.0, 2.2 Hz, C(2)-H), 6.72 (dd, 1H, J=10.0, 3.5 Hz), 7.35-7.42 (m, 6H,), 7.65-7.70 (m, 4H); $^{13}$C NMR (CDCl$_3$, 75.47 MHz) (Values for minor isomer in brackets[2]) δ 15.53 (q), 19.14 (s), 19.77 (q), 23.14 (t), 26.79 (q), 29.70 (t), 30.21 (q) , 31.50 (d), [31.73 (d)], 33.89 (t), 35.30 (t), 37.24 (t), [37.46 (t)], 39.23 (t), 40.51 (d), 54.77 (d), [57.0 (d)], 59.54 (t), [65.0 (d)], 65.48 (d), 69.21 (d), 69.50 (d), [70.0 (d)], [70.52 (d)], 98.39 (s), 114.97 (t), 127.53 (d), 127.56 (d), 128.07 (d), 129.50 (d), 129.52 (d), 133.85 (s), 135.48 (d), 138.18 (d), 154.21 (d), 201.51 (s); exact mass, m/z 519.2933 [calcd for C$_{32}$H$_{43}$O$_4$Si (M—CH$_3$—C$_5$H$_8$O)$^+$, m/z 519.2930].

[1]Price, C. C.; Balsley, R. B. J Org. Chem. 1966, 31, 3406.
[2]This spectrum was run on material that had been partially resolved (HPLC) and consisted largely of the major isomer.

Compound 7

($R_1$=Me, $R_2$=Me, $R_3$=SiPh$_2$Bu-t, $R_4$=H, configuration at C-1 being "S", and at C-3 being "R")

n-Butyllithium (1.6M in hexanes, 0.19 mL, 0.304 mmol) was added dropwise to a stirred and cooled (ice-bath) solution of diisopropylamine (0.042 mL, 0.300 mmol) in dry ether (3.0 mL). Stirring at 0° C. was continued for 10 min and the solution was then cooled to −78° C. The enone 6 ($R_2$=Me, $R_3$=SiPh$_2$Bu-t) (124.0 mg, 0.2319 mmol) in ether (2.0 mL plus 1.0 mL as a rinse) was added by syringe over about 15 min. Stirring at −78° C. was continued for 45 min and then aldehyde 6A ($R_1$=Me, configuration being R) (113.8 mg, 1.159 mmol) in ether (2 mL plus 0.25 mL as a rinse) was added also by syringe over about 5 min. After a further 10 min, glacial acetic acid (0.066 mL, 1.159 mmol) was injected, the cold-bath was removed and, after 10 min, ether (20 mL) and water (15 mL) were added with stirring. The phases were separated and the aqueous layer was extracted with ether (3×20 mL). The combined organic extracts were washed with saturated sodium bicarbonate (1×20 mL) and brine (1×20 mL), dried (Na$_2$SO$_4$), and evaporated. Flash chromatography of the residue over silica gel (1×20 cm) with ether—petroleum ether in the successive ratios of 1:4, 3:7, and 2:3 gave the aldol 7 ($R_1$=Me, $R_2$=Me, $R_3$=SiPh$_2$Bu-t, $R_4$=H, configuration at C-1 being S and at C-3 being R) (115.7 mg, 78%) as a homogeneous (TLC, silica gel, 2:3 ether—petroleum ether) oil: IR (CH$_2$Cl$_2$) 3420, 1712, 1674, 1112 cm$^{-1}$; $^1$H NMR (CDCl$_3$, 300.133 MHz) δ 1.03 (d, J=7.0 Hz, 3H), 1.04 (s, 9H), 1.11 (d, J=7.6 Hz, 3H), 1.36 (s, 3H), 1.41 (s, 3H), 1.2-1.8 (series of multiplets, 10H), 2.09 (d, J=6.0 Hz, 1H), 2.11-2.21 (m, 1H), 2.33 (t, J=6.0 Hz, 1H), 2.39-2.6 (m, 1H) , 2.6-2.81 (m, 1H) , 3.62-3.78 (m, 2H) , 3.78-3.97 (m, 2H), 4.04-4.19 (m, 1H), 4.98 (dd, J=10.5, 2.0 Hz, I H), 5.05 (ddd, J=17.5, 2.0, 1.0 Hz, 1H), 5.64 (ddd, J=17.5, 10.0, 8.5 Hz, 1H), 5.92 (dd, J=10.0, 2.4 Hz, 1H), 6.69 (ddd, J=10.0, 3.5 Hz, 1H), 7.32-7.46 (m, 6H), 7.6-7.71 (m, 4H); $^{13}$C NMR (CDCl$_3$, 75.46 MHz) δ 15.70, 19.21, 19.83, 21.43, 23.18, 26.85, 30.28, 31.53, 33.97, 34.73, 37.30, 39.3, 40.73, 43.57, 55.6, 59.62, 65.57, 68.22, 69.32, 98.44, 114.03, 127.63, 128.14, 129.58, 133.94, 135.55, 143.6, 154.14, 201.53; exact mass, m/z 519.2962 [calcd for C$_{32}$H$_{43}$O$_4$Si,(M—CH$_3$—C$_6$H$_{10}$O)$^+$ 519.2931].

Compound 7

($R_1$=Et, $R_2$=Me =Siph$_2$Bu-t, $R_4$=H, configuration at C-1 being "S" and at C-3 being "R").

Compound 7 ($R_1$=Et, $R_2$=Me, $R_3$=SiPh$_2$Bu-t, $R_4$=H, configuration at C-1 being "S" and at C-3 being "R") was prepared in 86% in an analogous manner but using aldehyde 6A ($R_1$=Et, configuration being R).

Compound 8

($R_1$=H, $R_2$=Me, $R_3$=SiPh$_2$Bu-t, $R_4$=SiEt$_3$)

Dry diisopropylamine (0.211 mL, 1.50 mmol), DMAP (62 mg, 0.51 mmol), and chlorotriethylsilane (0.254 mL, 1.50 mmol) were added to a stirred and cooled (ice-bath) solution of the alcohols 7 ($R_1$=H, $R_2$=Me, $R_3$=SiPh$_2$Bu-t, $R_4$=H) (311.3 mg, 0.50 mmol) in dry ether (7 mL). After 1 h the ice-bath was removed and stirring was continued for 36 h at room temperature (TLC control, silica, 1:4 ether—petroleum ether) Water (5 mL) and ether (50 mL) were then added The aqueous layer was separated and the ether layer was washed with water (15 mL). The combined aqueous phases were extracted with ether (20 mL) and the combined ether extracts were washed with saturated aqueous sodium bicarbonate (10 mL) and dried (MgSO$_4$). Evaporation of the solvent and flash chromatography of the residue over silica gel (3.0×17.0 cm) with 1:4 ethyl acetate—petroleum ether gave 8 ($R_1$=H, $R_2$=Me, $R_3$=SiPh$_2$Bu-t, $R_4$=SiEt3) (356.7 mg, 96%) as a thick oil: IR (film) 3080, 3060, 1670, 1640 cm$^{-1}$; $^1$H NMR (CDCl$_3$, 400 MHz) 6 0.55 (q, 6 H, J=8.3 Hz), 0.92 and 0.97 (t, 9H, J=8.3 Hz), 1.05 (s, 9H), 1.07 and 1.15 (d, J=7.5 Hz), 1.05-1.13 (m, 1H), 1.35 (s, 3H), 1.40 (s, 3H), 1.30-1.45 (m, 3H), 1.50-1.75 (m, 6H) 2.05-2.25 (m, 3H), 2.41 (dd, J=6.0, 2.5 Hz) and 2.47 (dd, J=7.3 and 5.0 Hz) (1H), 2.70-2.80 and 3.12-3.20 (m, 1H), 3.65-3.78 (m, 2H), 3.80-3.89 (m, 1H), 4.05-4.12 (m, 1H), 4.15-4.21 and 4.39-4.42 (m, 1H), 4.92-5.05 (m, 2H), 5.75-5.85 (m, 1H), 5.90 (dd, J=10.4, 2.0 Hz) and 5.92 (dd, =10.0, 2.6 Hz) (1H), 6.60 (dt, J=10.0, 1.8, 1.8 Hz) and 6.72 (dd, J=10.5, 4.0 Hz) (1H), 7.35-7.42 (m, 6H), 7.65-7.70 (m, 4H); $^{13}$C NMR (CDCl$_3$, 75.46 MHz) δ 5.10 (t) , 6.96 (q), 14.64 (q), [17.20 (q)]2, 19.21 (s), 19.62 (q), [22.73 (t)], 23.84 (t), 26.86 (q), [28.93 (t)], 9.42 (t), 30.28 (q), 31.31 (d), [31.80 (d)], 33.81 (t), 3.89 (t), [34.49 (t)], [35.34 (t)], [37.26 (t)], 37.42 (t), [39.24 (t)], 39.38 (t), 39.70 (d), 53.93 (d), 54.75 (d)], 57.59.64 (t), 65.54 (d), [65.60 (d)], 69.18 (d), [69.46 (d), 71.51 (d), [71.81 (d)], 98.43 (s), 114.57 (t), [114.70 (t)], 127.60 (d), [127.63 (d)], 128.39 (d), [128.67 (d)], 129.56 (d), 133.95 (s), 135.56 (d), [138.19 (d)], 138.55 (d), 153.52 (d), [154.22 (d)], 199.87 (s), [201.21 (s)]; exact mass, m/z 732.4592 (calcd for C$_{44}$H$_{68}$O$_5$Si2, m/z 732.4605). Anal. Calcd for $C_{44}H_{68}O_5Si_2$: C, 72.08; H, 9.35. Found: C, 72.07; H, 9.23.

[2] Values in parentheses refer to the minor isomer.

Compound 8

($R_1$=Me, $R_2$=Me, $R_3$=SiPh$_2$Bu-t, $R_4$=SiEt$_3$, configuration at C-1 being "S", and at C-3 being "R")

Dry diisopropylamine (0.071 mL, 0.506 mmol), DMAP (20 mg, 0.1637 mmol), and chlorotriethylsilane (0.085 mL, 0.506 mmol) were added to a stirred and cooled (ice-bath) solution of alcohol 7 ($R_1$=Me, $R_2$=Me, $R_3$=SiPh$_2$Bu-t, $R_4$=H, configuration at C-1 being S and at C-3 being R) (107.4 mg, 0.1697 mmol) in dry ether (3 mL). After 30 min the ice-bath was removed and stirring was continued for 24 h at room temperature [TLC control (1:4 ether—petroleum ether)]. Water (5 mL) and ether (25 mL) were then added. The aqueous layer was separated and the ether layer was washed with water (1×15 mL). The combined aqueous phases were extracted with ether (3×20 mL) and the combined ether extracts were washed with saturated aqueous sodium bicarbonate (1×15 mL) and dried (Na$_2$SO$_4$). Evaporation of the solvent and flash chromatography of the residue over silica gel (1×20 cm) with ether—petroleum ether in the successive ratios of 1:4, 1:1 gave 8 ($R_1$=Me, $R_2$=Me, $R_3$=SiPh$_2$Bu-t, $R_4$=SiEt$_3$, configuration at C-1 being S and at C-3 being R) [87 mg, 85% corrected for recovered starting material (21 mg)] as a homogeneous (TLC, silica gel, 1:4 ether—petroleum ether), thick oil: IR (CH$_2$Cl$_2$) 1670, 1640, cm$^{-1}$; $^1$H NMR (CDCl$_3$, 300.133 MHz) δ 0.59 (q, J=8.0 Hz, 6H), 0.96 (t, J=8.0 Hz, 9H), 1.0 (d, J=7.0 Hz, 3H), 1.04 (s, 9H), 1.06 (d, J=7.6 Hz, 3H), 0.95-1.15 (m, 1H), 1.36 (s, 3H), 1.41 (s, 3H), 1.24-1.59 (m, 6H), 1.59-1.85 (m, 3H), 2.06-2.19 (m, 1H), 2.2-2.38 (m, 1H), 2.43 (dd, J=9.0, 4.0 Hz, 1H), 2.62-2.78 (m, 1H), 3.61-3.90 (m, 3H), 4.03-4.18 (m, 1H), 4.48 (dt, J=8.0, 4.0 Hz, 1H), 4.94-5.07 (m, 2H), 5.72 (ddd, J=17.5, 10.5, 7.5 Hz, 1H), 5.88 (dd, J=10.0, 1.5 Hz, 1H), 6.79 (dd, J=10.0, 4.5 Hz, 1H), 7.31-7.47 (m, 6H), 7.6-7.72 (m, 4H); $^{13}$C NMR (CDCl$_3$, 75.46 MHz) δ 5.36, 7.06, 14.13, 19.25, 19.84, 21.60, 24.42, 26.89, 30.31, 31.28, 33.81, 34.34, 37.43, 39.24, 39.44, 41.73, 54.22, 59.67, 65.56, 69.19, 70.76, 98.46, 113.22, 127.62, 127.65, 128.55, 129.59, 134.01, 135.59, 144.19, 154.15, 199.68; exact mass, m/z 746.4737 (calcd for $C_{45}H_{70}O_5Si_2$, 746.4761). Anal. Calcd for $C_{45}H_{70}O_5Si_2$: C, 72.33; H, 9.44. Found: C, 72.45; H, 9.51.

Compound 8

($R_1$=Et, $R_2$=Me, $R_3$=SiPh$_2$Bu-t, $R_4$=SiEt$_3$, configuration at C-1 being "S", and at C-3 being "R")

Compound 8 ($R_1$=Et. $R_2$=Me, $R_3$=SiPh$_2$Bu-t, $R_4$=SiEt$_3$, configuration at C-1 being S and at C-3 being R) was prepared in 90% in an analogous manner.

Compound 9

($R_1$=H, $R_2$=Me, $R_3$=SiPh$_2$Bu-t, $R_4$=SiEt$_3$)

Ozonized oxygen, cooled by passage through a glass coil immersed in an acetone-dry ice bath, was bubbled for 45 sec into a stirred and cooled (−78° C.) solution of the enone-olefins 8 ($R_1$=H, $R_2$=Me, $R_3$=SiPh$_2$Bu-t, $R_4$ =SiEt$_3$) (119.3 mg, 0.163 mmol) in dry dichloromethane (5 mL). [Previous experiments had shown that a period of 45 sec was suitable and left a small amount of starting material unchanged. It is important not to take the reaction to completion.] The ozone stream was stopped, the reaction mixture was stirred at −78° C. for 5 min, and then purged with dry argon for 10 min. Triphenylphosphine (84 mg, 0.320 mmol) was added and the mixture was stirred under argon for 8 h, the cold-bath being removed after 20 min. Evaporation of the solvent and flash chromatography of the residue over silica gel (3.0×17.0 cm) with 1:4 ethyl acetate—petroleum ether gave the enone-aldehydes 9 ($R_1$=H, $R_2$=Me, $R_3$=SiPh$_2$Bu-t, $R_4$=SiEt$_3$) (82.6 mg, 69%) and starting enone-olefins 8 ($R_1$=H, $R_1$=Me, $R_3$=SiPh$_2$Bu-t, $R_4$=SiEt$_3$) (15 m9). The enone aldehydes 9 ($R_1$=H, $R_2$=Me, $R_3$=SiPh$_2$Bu-t, $R_4$=SiEt$_3$) (78%, corrected for recovered starting material) had: IR (film) 2730, 1720, 1670, 1590 cm$^{-1}$; $^1$H NMR (CDCl$_3$, 400 MHz) δ 0.57 (q, 6H, J=8.0 Hz), 0.92 and 0.97 (t, 9H, J=8.0 Hz), 1.05 (s, 9H), 1.09 and 1.15 (d, 3H, J=7.0 Hz), 1.05-1.19 (m, 1H), 1.32 (s, 3H), 1.41 (s, 3H), 1.35-1.48 (m, 3H), 1.50-1.75 (m, 4H), 1.80-1.95 (m, 2H), 2.05-2.12 and 2.22-2.29 (m, 1H), 2.45 (dd, 1H, J=8.0, 5.0 Hz), 2.55 (t, 2H, J=8.0 Hz), 2.70-2.75 and 3.0-3.09 (m, 1H), 3.65-3.78 (m, 2H), 3.80-3.90 (m, 1H), 4.05-4.25 (m, 1H), 4.45-4.50 (m, 1H), 5.90 (dd, 1H, J=10.0, 2.0 Hz), 6.62 (dt, J=10.0, 2.0, 2.0 Hz) and 6.78 (dd, J=10.0, 4.0 Hz) (1H), 7.35-7.42 (m, 6H), 7.65-7.70 (m, 4H), 9.78-9 80 (bs, 1H); $^{13}$C NMR (CDCl$_3$, 75.47 MHz) δ 5.02 (t), 6.94 (q), 14.41 (d), 19.21 (s), 19.79 (q), [22.43 (t)], 23.94 (t), 26.41 (t), 26.86 (q), 30.27 (q), 31.29 (t), [31.43 (t)], 33.67 (t), [34.37 (t)], 37.42 (t), 39.38 (t), 39.49 (d), 40.05 (t), 53.67 (d), 59.63 (t), 65.52 (d), 69.12 (d), [69.39 (d)], 70.75 (d), 98.43 (s), 127.62 (d), 128.18 (d), 129.56 (d), 133.93 (s), 133.97 (s), 135.56 (d), 153.91 (d), 199.57 (s), 202.07 (d); exact mass. m/z 719.4157 [calcd for $C_{42}H_{63}O_6Si_2$ (M—CH$_3$)$^+$, m/z 719.4163].

Compound 9

($R_1$=Me, $R_2$=Me, $R_3$=SiPh$_2$Bu-t, $R_4$=SiEt$_3$, configuration at C-1 being at C-3 being "R").

This experiment was done using the apparatus described by Rueben,[1] but with a pear-shaped reagent bulb. Ozonized oxygen, cooled by passage through a glass coil immersed in a dry-ice acetone-bath, was bubbled for 4 min into dry dichloromethane (5 mL) at −78° C. The resulting solution was transferred into the other bulb of the apparatus, which contained a cold (−78° C.) solution of 8 ($R_1$=Me, $R_2$=Me, $R_3$=SiPh$_2$Bu-t, $R_4$=SiEt$_3$, configuration at C-1 being S and at C-3 being R) (59.5 mg, 0.0796 mmol) in dichloromethane (3 mL). The resulting mixture was stirred for 5 min, and triphenylphosphine (65.0 mg, 0.248 mmol) was then tipped in. The cooling-bath was removed and stirring was continued for 3 h. Evaporation of the solvent and flash chromatography of the residue over silica gel (1×b 18 cm) with ether—petroleum ether in the successive ratios of 1:9, 2:8, and 3:7 gave 9 ($R_1$=Me, $R_2$=Me, $R_3$=SiPh$_2$Bu-t, $R_4$=SiEt$_3$, configuration at C-1 being S and at C-3 being R) [35.2 mg, 85% after correction for recovered 8 ($R_1$=Me, $R_2$=Me, $R_3$=SiPh$_2$Bu-t, $R_4$=SiEt$_3$, configuration at C-1 being S and at C-3 being R) (18.1 mg)] as an apparently homogeneous (TLC, silica gel, 4:6 ether—petroleum ether) oil: IR (CH$_2$Cl$_2$) 1726, 1669 cm$^{-1}$; $^1$H NMR (CDCl$_3$, 300.133 MHz) δ 0.57 (q, J=8.0 Hz, 6H), 0.94 (t, J=8.0 Hz, 9H), 1.04 (s, 9H), 1.08 (d, J=7.0 Hz, 3H), 1.13 (d, J=7.0 Hz, 3H), 1.05-1.16 (m, 1H) , 1.36 (s, 3H) , 1.41 (s, 3H), 1.31-1.48 (m, 3H), 1.48-1.8 (m, 5H), 1.92 (dddd, J=14.0, 12.0, 8.0, 4.0 Hz, 1H), 2.08-2.2 (m, 1H), 2.43-2.56 (m, 1H), 2.47 (dd, J=8.0, 5.0 Hz, 1H), 2.67–2.81 (m, 1H), 3.62–3.90 (m, 3H), 4.06–4.17 (m, 1H), 4.54 (dt, J=8.0, 4.0 Hz, 1H), 5.89 (dd, J=10.0, 1.8 Hz, 1H), 6.81 (dd, J=10.0, 5.0 Hz, 1H), 7.31–7 5 (m, 6H), 7.6–7.74 (m, 4H), 9.66 (d, J= 2.0 Hz, 1H); $^{13}$C NMR (CDCl$_3$, 75.46 MHz) δ 5.15, 6.96, 14.1, 14.31, 19.23, 19.62, 24.14, 26.87, 30.29, 31.25, 33.67, 35.73, 37.41, 39.41, 43.08, 53.71, 59.66, 65.54, 69.05, 70.09, 98.45, 127.60, 128.32, 129.57, 134.00, @35.57, 154.15, 199.45, 204.46; exact mass, m/z 748.4548 (calcd for C$_{44}$H$_{68}$O$_6$Si$_2$, 748.45542).
[1]Rubin, M. B. *J. Chem. Educ.* 1964, 41, 388.

Compound 9

($R_1$=Et, $R_2$=Me, $R_3$=SiPh$_2$Bu-t, $R_4$=SiEt$_3$, configuration at C-1 being "S" and at C-3 being "R")

Compound 9 ($R_1$=Et, $R_2$=Me, $R_3$=SiPh$_2$Bu-t, $R_4$=SiEt$_3$, configuration at C-1 being S and at C-3 being R) was prepared in 67% in an analogous manner.

Compound 10

($R_1$=H, $R_2$=Me, $R_3$=SiPh$_2$Bu-t, $R_4$=SiEt$_3$)

(a) Graphite powder (3.1022 g) was heated with magnetic stirring at 130° to 140° C. for 1 h in a Schlenk tube[1] purged by a slow stream of argon. Freshly cut pieces of potassium metal (1.1114 g) were added and the hot mixture was stirred vigorously under an argon stream for 30 min, by which time a bronze-colored powder had formed. The potassium graphite (C$_8$K) was cooled to room temperature and used as described below.
[1]This consisted of a tube with a 24/40 neck (carrying a bent adapter with top) and a side one (fitted with a tap) near the mouth of the tube.

Potassium graphite (C$_8$K) (98.7 mg, 0.7301 mmol) and titanium trichloride (53.9 mg, 0.3494 mmol) were weighed under argon in a glove bag and transferred successively to a 25-mL 3-necked flask containing dry DME (5 mL). The mixture was stirred and refluxed for 2 h under argon and then cooled to room temperature. The enone aldehydes 9 ($R_1$=H, $R_2$=Me, $R_3$=SiPh$_2$Bu-t, $R_4$=SiEt$_3$) (15 mg, 0.0204 mmol) in dry DME (5 mL)[2] were added by syringe pump over 9 h to the stirred slurry of titanium reagent. Stirring was continued for an additional 5 h. The mixture was then refluxed for 3 h cooled to room temperature, and filtered under a blanket of argon through a pad of Florisil (3.5×6 cm) contained in a sintered funnel equipped with an argon inlet near the top. The column was washed with ether (3×50 mL). Evaporation of the combined filtrates and flash chromatography of the residue over silica gel (1×15 cm) with 1:9 ether—petroleum ether gave compound 10 ($R_1$=H, $R_2$=Me, $R_3$=SiPh$_2$Bu-t, $R_4$=SiEt$_3$) (12.2 mg, 85%) as an apparently homogeneous (TLC, silica, 1:4 ether—petroleum ether) oil: IR (film) 1590 cm$^{-1}$; $^1$H NMR (CDCl$_3$, 400 MHz) δ 0.62 and 0.67 (q, 6H, J=8.0 Hz), 0.85 and 0.95 (d, 3H, J=7.0 Hz), 0.98 and 1.00 (t, 9H, J=8.0 Hz), 1.05 (s, 9H), 1.10–1.30 (m, 3H), 1.40 (s, 3H), 1.45 (s, 3H), 1.48–1.52 (m, 1H), 1.62–1.80 (m, 5H), 1.87–1.92 (m, 1H), 2.0–2.17 (m, 2H), 2.30–2.40 (m, 2H), 3.65–3.72 (m, 1H), 3.78–3.90 (m, 2H), 4.12–4.20 (m, 1H), 4.28–4.32 (bs, 1H), 5.45–5.49 (bs) and 5.50–5.55 (bs) (1H), 5.67 (dd, J=10.0, 6.0 Hz) and 5.71 (dd, J=10.0, 6.0 Hz, 1H), 5.95 (d, 1H, J=10.0 Hz, 7.35–7.45 (m, 6H), 7.65–7.70 (m, 4H); $^{13}$C NMR (CDCl$_3$, 75.47 MHz) δ 5.56 (t), 5.89 (t), 7.25 (q), [13.63 (q)], 14.15 (q), 19.27 (s), 19.82 (q), 21.14 (t), 23.83 (t), 28.90 (q), 30.36 (q), 30.71 (d), [32.06 (d)], [32.69 (t)], 33.58 (t), [34.37 (t)], 36.57 (d), 37.42 (t), 39.51 (t), 39.83 (d), [42.99 (t)], [43.20 (t)], 59.74 (t), 65.47 (d), 65.63 (d), [69.09 (d)], 69.84 (d), 71.68 (d), 98.43 (s), [122.94 (d)], 123.55(d), 127.64 (d), [128.22 (d)], 128.74 (d), 129.60 (d), 132.69 (d), 134.00 (s), 134.05 (s), 135.60 (d); [137.48 (d)]; mass, m/z 702 (calcd for C$_{42}$H$_{66}$O$_4$Si$_2$, m/z 702); m/z 687.4257 [calcd for C$_{42}$H$_{63}$O$_4$Si$_2$ (M—CH$_3$)$^+$], m/z 687.4265).
[2]The starting material was dissolved in 4 mL of DME which was drawn up into the syringe, and a further 1 mL of DME was injected into the flask and also drawn up into the syringe. followed by some argon (to expel all of the solution by the end of the addition, which was done using a syringe pump).

(b) Similar results were obtained by performing the reaction in THF but using the alternative titanium reagent prepared from sodium naphthalene (0.3003 mmol), titanium tetrachloride (0.1074 mmol), and enone-aldehyde 9 ($R_1$=H, $R_2$=Me, $R_3$=SiPh$_2$Bu-t, $R_4$=SiEt$_3$) (0.0068 mmol) with a similar reaction period.

Compound 10

($R_1$=Me, $R_2$=Me, $R_3$=SiPh$_2$Bu-t, $R_4$=SiEt$_3$, configuration at C-1 being "S" and at C-3 being "R")

Freshly prepared potassium graphite (C$_8$K) (364 mg, 2.69 mmol) and titanium trichloride (192.6 mg, 1.2485 mmol) were weighed under argon in a glove bag and transferred successively to a 50-mL 3-necked flask containing dry DME (15 mL). The mixture was stirred and refluxed for 2 h under argon and then cooled to room temperature. The enone aldehyde 9 ($R_1$=Me, $R_2$=Me, R3 =SiPh$_2$Bu-t, $R_4$=SiEt$_3$, configuration at C-1 being S and at C-3 being R) (55.2 mg, 0.0736 mmol) in dry DME (5 mL)[1] was added by syringe pump over 9 h to the stirred slurry of titanium reagent. Stirring was continued for an additional 5 h. The mixture was then refluxed for 4 h, cooled to room temperature, and filtered under a blanket of argon through a pad of Florisil (3.5×6 cm) contained in a sintered funnel equipped with an argon inlet near the top. The column was washed with ether (3×50 mL). Evaporation of the combined filtrates and flash chromatography of the residue over silica gel (1×15 cm) with 1:9 ether—petroleum ether gave 10 ($R_1$=Me, $R_2$=Me, $R_3$=SiPh$_2$Bu-t, $R_4$=SiEt$_3$, configuration at C-1 being S and at C-3 being R) (45.6 mg, 86%) as an apparently homogeneous (TLC, silica, 1:9 ether—petroleum ether) oil: IR (CH$_2$Cl$_2$) 1428, 1378, 1112, 1077 cm$^{-1}$; $^1$H NMR (CDCl$_3$, 300.133 MHz) δ 0.62 (dq, J=8.0, 3.0 Hz, 6H), 0.86 (d, J=7.0 Hz, 3H), 0.95 (t, J=8.0 Hz, 9H), 1.07 (s, 9H), 1.15 (d, J=7.5 Hz, 3H), 1.09–1.28 (m, 3H), 1.38 (s, 3H), 1.45 (s, 3H), 1.46–1 92 (m, 8H), 2.04 (dq, J=12.5, 2.5 Hz, 1H), 2 29–2.46 (m, 2H), 3.69 (dt, J=10.0, 5.0 Hz, 1H), 3.76–3.92 (m, 2H), 4.08–4.2 (m, 1H), 4.24–4.31 (m, 1H), 5.4–5.48 (m, 1H), 5.75 (dd, J=9.5, 6.2 Hz, 1H), 5.97 (d, J=9 5, Hz, 1H), 7.3–7.57 (m, 6H), 7.6–77 (m, 4H); $^{13}$C NMR (CDCl$_3$, 75.46 MHz) δ 5.50, 7.23, 14.22, 19.23, 19.78, 23.66, 24.15, 26.85, 28.01, 30.31, 30.43, 33.47, 35.90, 36.75, 37.35, 39.44, 39.75, 59.68, 65.58, 65.84, 69.76, 98.40, 127.61, 128.89, 129.57, 131.69, 132.83, 133.91, 133.98, 135.56; exact mass, m/z 716.4672 (calcd for C$_{44}$H$_{68}$O$_4$Si$_2$, 716.4656).
[1]The starting material was dissolved in 4 mL of DME which was drawn up into the syringe, and a further 1 mL of DME was injected into the flask and also drawn up into the syringe, followed by some argon (to expel all of the solution by the end of the addition, which was done using a syringe pump).

Compound 10

($R_1$=Et, $R_2$=Me, $R_3$=SiPh$_2$Bu-t, $R_4$=SiEt$_3$, configuration at C-1 being "S" and at C-3 being "R")

Compound 10 ($R_1$=Et, $R_2$=Me, $R_3$=Siph$_2$Bu-t, $R_4$=SiEt$_3$, configuration at C-1 being "S" and at C-3 being "R") was prepared in 89% in an analogous manner.

Compound 11

($R_1$=H, $R_2$=Me, $R_3$=SiPh$_2$Bu-t, $R_4$=H)

The Silyl ether 10 ($R_1$=H, $R_2$=Me, $R_3$=SiPh$_2$Bu-t, $R_4$=SiEt$_3$) (53.7 mg, 0.076 mmol) was dissolved in a mixture of acetonitrile (0.80 mL) and sufficient dichloromethane (0.20 mL) to produce a homogeneous solution. Aqueous hydrofluoric acid (48% w/v, 2 mL) was diluted with acetonitrile to a total volume of 100 mL. A portion (0.166 mL, 0.07965 mmol HF) of this solution was added to the solution of 10 ($R_1$=H, $R_2$=Me, $R_3$=SiPh$_2$Bu-t, $R_4$=SiEt$_3$) and the mixture was stirred at room temperature for 1.75 h (TLC control). Solid sodium bicarbonate was added. The mixture was stirred for 10 min and the solvent was evaporated. The residue was partitioned between ethyl acetate (20 mL) and water (5 mL). The alkaline aqueous layer was extracted with ethyl acetate (10 mL) and the combined organic extracts were washed with brine (10 mL) and dried (MgSO$_4$). Evaporation of the solvent and flash chromatography of the residue over silica gel (1.0×10.0 cm) with 1:4 ethyl acetate—petroleum ether gave 11 ($R_1$=H, $R_2$=Me, $R_3$=SiPh$_2$Bu-t, $R_4$=H) (9.6 mg) and, on further elution with ethyl acetate, a triol (formed by hydrolysis of the ketal function) (27.8 mg) was obtained. The triol (27.8 mg, 0.05i mmol) was dissolved in dry dichloromethane (0.7 mL) and cooled to 0° C. 2-Methoxypropene (0.01 mL, 0.104 mmol) and pyridinium p-toluenesulfonate (2.7 mg, 0.011 mmol) were added. The mixture was stirred at 0° C. for 40 min, by which time ketalization was complete (TLC control, silica, 1:4 ethyl acetate—petroleum ether). The solution was diluted with dichloromethane (10 mL) and washed once with saturated aqueous sodium bicarbonate (5 mL). The aqueous phase was extracted with dichloromethane (3 mL) and the combined organic layers were dried (Na$_2$SO$_4$) and evaporated. Flash chromatography of the residue over silica gel (1.0×10.0 cm) with 1:6 ethyl acetate—petroleum ether gave 11 ($R_1$=H, $R_2$=Me, $R_3$=SiPh$_2$Bu-t, $R_4$=H) (28.9 mg, 97%). The overall yield of 11 ($R_1$=H, $R_2$=Me, $R_3$=SiPh$_2$Bu-t, $R_4$=H) amounted to 38.5 mg (85%): IR (film) 3580–3300 cm$^{-1}$; $^1$H NMR (CDCl$_3$, 400 MHz) δ 0.87 and 0.92 (d, 3H, J=7.0 Hz), 1.04 (s, 9H), 1.15 (q, 1H, J=12.4 Hz), 1.22–1.50 (m, 3H), 1.34 (s, 3H), 1.42 (s, 3H), 1.51–1.83 (m, 8H), 1.90–2.05 (m, 1H), 2.07–2.20 (m, 2H), 2.29–2.45 (m, 2H), 3.65–3.72 (m, 1H), 3.80–3.90 (m, 2H), 4.08–4.15 (m, 1H), 4.20–4.25 (m, 1H), 5.45–5.48 and 5.52–5.58 (bs, 1H), 5.69 (dd, J=10.0, 5.0 Hz) and 5.75 (dd, J=10.0, 5.5 Hz) (1H), 5.92 (d, J=10.0 Hz) and 5.95 (d, J=10.0 Hz) (1H), 7.35–7.42 (m, 6H), 7.62–7.70 (m, 4H); $^{13}$C NMR (CDCl$_3$, 75.47 MHz) δ [13.77 (q)], 14.02 (q), 19.23 (s), 19.90 (q), 20.45 (t), 23.22 (t), [24.26 (t)], [25.85 (t)], 26.89 (q), 29.04 (t), 30.32 (q), 30.90 (d), [32.79 (d)], [32.98 (t)], 33.10 (t), [34.42 (t)], 36.05 (d), [37.13 (t)], 37.56 (t), 38.92 (d), 39.37 (t), [43.01 (d)], [43.25 (d)], 59.69 (t), 64.32 (d), 65.65 (d), 68.69 (d), [69.13 (d)], [71.01 (d)], [98.46 (s)], 98.53 (s), [123.30 (d)], 123.66 (d), 127.62 (d), [127.95 (d)], 128.43 (d), 129.58 (d), 133.28 (d), 133.53 (s), [133.93 (s)], 134.00 (s), 135.58 (d), [136.83 (s)]; mass, m/z 588 (Calcd for C$_{37}$H$_{52}$O$_4$Si, m/z 588).

In this reaction it is more convenient to bypass the chromatographic separation of the triol and the desired product. The crude product is dried (oil-pump, 2 h) and then reketalized. The desilylation can also be done using more than (2.2 equiv) of hydrofluoric acid.

Compound 12

($R_1$=H, $R_2$=Me, $R_3$=SiPh$_2$Bu-t).

A solution of the alcohols 11 ($R_1$=H, $R_2$=Me, $R_3$=SiPh$_2$Bu-t, $R_4$=H) (50 mg, 0.085 mmol) in dry dichloromethane (1 mL) was added by cannula to a stirred and cooled (−78° C.) mixture of oxalyl chloride (0.009 mL, 0.102 mmol) and dry DMSO (0.0133 mL, 0.187 mmol) in dry dichloromethane (5 mL). More dichloromethane (0.5 mL) was used as a rinse. The reaction mixture was stirred for 15 min and then dry triethylamine (0.060 mL, 0.425 mmol) was injected. Stirring at −78° C. was continued for 5 min, the cold-bath was removed and stirring was continued for a further 20 min. Dichloromethane (10 mL) was added to the mixture followed by brine (100 mL). The organic layer was separated and the aqueous phase was extracted with dichloromethane (5 mL). The combined organic extracts were dried (Na$_2$SO$_4$) and evaporated. Flash Chromatography of the residue over silica gel (1.0×10.0 cm) with 1:5 ethyl acetate—petroleum ether gave ketone 12 ($R_1$=H, $R_2$=Me, $R_3$=SiPh$_2$Bu-t) [38.2 mg, 76% (93%, corrected for recovered starting material)]: IR (film) 1720 cm$^{-1}$; $^1$H NMR (CDCl$_3$, 400 MHz) δ 0.9 (d, 3H, J=7.0 Hz), 1.04 (s, 9H), 1.11 (q, 1 H, J=12.0 Hz), 1.23–1.75 (m, 8H), 1.35 (s, 3H), 1.42 (s, 3H), 1.92–2.0 (m, 1H), 2.35–2.46 (m, 2H), 2.52–2.62 (m, 3H), 2.95 (bd, 1H, J=12.0 Hz), 3.65–3.90 (m, 3H), 4.08–4.15 (m, 1H), 5.65 (m, 1H), 5.78 (dd, 1H, J=9.5, 6.0 Hz), 6.03 (d, 1H, J=10.0 Hz), 7.35–7.42 (m, 6H), 7.62–7.70 (m, 4H).

Further elution with 1:6 ethyl acetate—petroleum ether gave the starting alcohol (9.1 mg).

Compound 13

($R_1$=H, $R_2$=Me, $R_3$=SiPh$_2$Bu-t, $R_4$=H, configuration at C-1 being "S")

L-Selectride (1M in THF, 0.130 mL, 0.130 mmol) was added under argon to a stirred and cooled (−78° C.) of ketone 12 ($R_1$=H, $R_2$=Me, $R_3$=SiPh$_2$Bu-t) (38.2 mg, 0.60 mmol) in dry THF (2 mL). Stirring was continued for 1 h at −78° C. and at −43° C. (acetonitrile--dry-ice cold bath) for 12 h.[1] The cold-bath was removed and stirring was continued for 20 min. A mixture of 10% w/v aqueous sodium hydroxide (0.055 mL) and 30% w/v aqueous hydrogen peroxide (0.055 mL) was then added to the stirred solution, followed, after a further 2 h, by ethyl acetate (20 mL). The organic layer was separated and the aqueous layer was extracted with ethyl acetate (1×10 mL). The combined organic extracts were washed with brine (10 mL), dried (MgSO$_4$) and evaporated. Flash chromatography of the residue over silica gel (1.0×10.0 cm) with 1:4 ethyl acetate—petroleum ether gave the alcohol—petroleum ether gave the alcohol 13 ($R_1$=H, $R_2$=Me, $R_3$=Siph-$_2$Bu-t, $R_4$=H, configuration at C-1 being S) (30.7 mg, 80%): IR (film) 3420–3600 cm$^{-1}$; $^1$H NMR (CDCl$_3$, 400 MHz) δ 0.89 (d, 3H, J=7.0 Hz), 1.05 (s, 9H), 1.15 (q, 1H, J=12.0 Hz), 1.25–1.35 (m, 2H), 1.39 (s, 3H), 1.42 (s, 3H), 1.48 (dt, 1H, J=12.6, 2.5, 2.5 Hz), 1.55–1.90 (m, 7H), 2.0–2.05 (m, 1H), 2.12–2.22 (m, 2H), 2.30–2.45 (m, 2H), 3.67–3.72 (m, 1H), 3.80–3.90 (m, 2H), 4.10–4.17 (m, 1H), 4.22–4.29 (bs, 1H, W$_½$ 12.5 Hz), 5.54–5.60 (bs, 1H), 5.75 (dd, 1H, J=9.5, 6.0 Hz), 5.95 (d, 1H, J=9.5 Hz), 7.35–7.45 (m, 6H), 7.65–7.70 (m, 4H): $^{13}$C NMR (CDCl$_3$, 75.47 MHz) δ 14.03 (q), 19.25 (s), 19.92 (q), 20.46 (t), 23.25 (t), 26.90 (q), 29.06 (t), 30.33 (d), 30.93 (d), 33.13 (t), 36.08 (d), 37.58 (t), 38.95 (d), 39.40 (t), 59.73 (t), 64.55 (d), 65.68 (d), 68.72 (d), 98.55 (s), 123.68 (d), 127.64 (d), 127.66 (d), 128.45 (d), 129.59 (d), 133.32 (d), 133.55 (s), 133.97 (s), 134.0 (s), 135.61 (d); mass, m/z 588 (calcd for C$_{37}$H$_{52}$O$_4$Si m/z 588).

[1] In subsequent runs the whole experiment was conducted at 0° C. with a reaction time of 1.5 h.

Compound 11

($R_1$=Me, $R_2$=Me, $R_3$=Siph$_2$Bu-t, $R_4$=H, configuration at C-1 being "S" and at C-3 being "R")

Tetrabutylammonium fluoride (1.1M in THF, 0.6 mL, 0.66 mmol) was added to a solution of 10 ($R_1$=Me, $R_2$=Me, $R_3$=SiPh$_2$Bu-t, $R_4$=SiEt$_3$, configuration at C-1 being S and at C-3 being R) (25.0 mg, 0.03486 mmol) in THF (1.5 mL) and the mixture was stirred for 22 h at room temperature (TLC control, silica, 3:2 ether—petroleum ether). Evaporation of the solvent and flash chromatography of the reside over silica gel (1×10 cm) first with 1:1 ether—petroleum ether and then with ether gave the C-1, C-15 diol (12.7 mg, 99%) as a homogeneous (TLC, silica, ether) oil, which was used directly in the next step.

"tert"-Butyldiphenylsilyl chloride (0.01 mL, 0.047 mmol), triethylamine (0.006 mL, 0.o5 mmol), and DMAP (5 mg) were added successively to a stirred and cooled (ice-bath) solution of the above diol (12.7 mg, 0.0348 mmol) in dry dichloromethane (2 mL). The cooling-bath was removed and the mixture was stirred for 24 h and was then evaporated. Flash chromatography of the residue over silica gel (1×16 cm) with 1.4 ether—petroleum ether gave 11 ($R_1$=Me, $R_2$=Me, $R_3$=SiPh$_2$Bu-t, $R_4$=H, configuration at C-1 being "S" and at C-3 being "R") (20.0 mg, 95%) as a homogeneous (TLC, silica gel, 1:4 ether—petroleum ether), colorless oil: IR (CH$_2$Cl$_2$) 3320 cm$^{-1}$; $^1$H NMR (CDCl$_3$, 300.133 MHz) δ 0.89 (d, J=7.0 Hz, 3H), 1.04 (s, 9H), 1.19 (d, J=7.3 Hz, 3H), 1.1–1.85 (series of multiplets, 10H), 1.37 (s, 3H), 1.43 (s, 3H), 1.88 (dd, J=4.5, 3.5 Hz, 2H), 2.14 (dq, J=12.5, 2 5 Hz, 1H), 2.32-2.51 (m, 2H), 3.69 (dt, J=10.4, 5.2 Hz, 1H), 3.77–3.90 (m, 2H), 4.06–4.18 (m, 1H), 4.18–4.3 (m, 1H), 5.54 (t, J=3.3 Hz, 1H), 5.80 (dd, J=9.5, 6.0 Hz, 1H), 5.98 (d, J=9.5, Hz, 1H), 7.3–7.48 (m, 6H), 7.6–7.76 (m, 4H); $^{13}$C NMR (CDCl$_3$, 75.46 MHz) δ 14.03, 19.23, 19.86, 23.38, 23.67, 26.86(3C), 27.57, 30.28, 30.81, 33.13, 35.6, 35.93, 37.53, 38.76, 39.36, 59.68, 65.34, 65.64, 68.67, 98.52, 127.6, 128.51, 129.56, 130.01, 131.55, 133.60, 134.0, 135.57; exact mass, m/z 602.3790 (calcd for C$_{38}$H$_{54}$O$_4$Si, 602.3791).

Compound 11

($R_1$=Et, $R_2$=Me, $R_3$=Siph$_2$Bu-t, $R_4$=H, configuration at C-1 being "S" and at C-3 being "R":

Compound 11 ($R_1$=Et, $R_2$=Me, $R_3$=SiPh$_2$Bu-t, $R_4$=prepared in 93% in an analogous manner.

Compound 14

($R_1$=H, $R_2$=Me, $R_3$=SiPh$_2$Bu-t, $R_4$=α-methylbutyroyl, configuration at C-1 being "S", and at the α-position of the methylbutyroyl group being "S")

4-(Dimethylamino)pyridine (14 mg, 0.1123 mmol), dry triethylamine (0.041 mL, 0.299 mmol) and ("S")-2-methylbutyric anhydride (0.049 mL, 0.262 mmol) were added in that order to a stirred solution of 13 ($R_1$=H, $R_2$=Me, $R_3$=SiPh$_2$Bu-t, $R_4$=H, configuration at C-1 being S) (22.0 mg, 0.0374 mmol) in dry dichloromethane (5 mL). After 24 h further portions of DMAP (14 mg, 0.1123 mmol), triethylamine (0.041 mL, 0.299 mmol), and ("S")-2-methylbutyric anhydride (0.049 mL, 0.262 mmol) were added and stirring was continued for another 44 h (TLC control). The mixture was concentrated (water-pump, room temperature) and flash chromatography of the residue over silica gel (1.0×10.0 cm) with 1:4 ether—petroleum ether gave the ester 14 ($R_1$=H, $R_2$=Me, $R_3$=SiPh$_2$Bu-t, $R_4$=α-methylbutyroyl, configuration at C-1 being "S", and at the α-position of the methylbutyroyl group being "S") (24.9 mg, 99%): $[α]_D^{27}$30 122.42 (c 1.49, CHCl$_3$); IR (film) 1720 cm$^{-1}$; $^1$H NMR (CDCl$_3$, 400 MHz) δ 0.89 (d, 3H), J=7.0 Hz), 0.91 (t, 3H, J=7.0 Hz), 1.05 (s, 9H), 1.02–1.15 (m, 2H), 1.13 (d, 3H, J=7.0 Hz), 1.20–1.30 (m, 1H), 1.35 (s, 3H), 1.42 (s, 3H), 1.38–1.40 (m, 3H), 1.60–1.72 (m, 6H), 2.10–2.24 (m, 3H), 2.29–2.42 (m, 3H), 3.65–3.75 (m, 2H), 3.80–3.89 (m, 1H), 4.08–4.15 (m, 1H), 5.30–5.35 (bs, 1H), 5.54–5.59 (bs, 1H), 5.75 (dd, 1H, J=10.0, 6.0 Hz), 5.95 (d, 1H, J=10.0 Hz), 7.35–7.43 (m, 6H), 7.65–7.70 (m, 4H); $^{13}$C NMR (CDCl$_3$, 75.47 MHz) δ 11.85 (q), 13.85 (q), 17.04 (q), 19.25 (s), 19.94 (q), 20.99 (t), 23.75 (t), 26.23 (t), 26.78 (t), 26.89 (q), 30.30 (q), 30.90 (d), 33.93 (t), 37.10 (d), 37.45 (t), 37.63 (d), 39.42 (t), 41.71 (d), 59.67 (t), 65.43 (d), 67.66 (d), 69.57 (d), 98.43 (s), 123.47 (d), 127.62 (d), 127.63 (d), 128.09 (d), 129.57 (d), 133.20 (d), 133.99 (s), 135.60 (d), 176.57 (s); exact mass, m/z 672 4207 (calcd for C$_{42}$H$_{60}$O$_5$Si, m/z 672.4209).

Compound 14

($R_1$=Me, $R_2$=Me, $R_3$=SiPh$_2$Bu-t, $R_4$=α-methylbutyroyl, configuration at C-1 being "S", at C-3 being "R" and at the α-position of the methylbutyroyl group being "S")

4-(Dimethylamino)pyridine (28 mg, 0.2246 mmol), dry triethylamine (0.082 mL, 0.598 mmol) and ("S")-2-methylbutyric anhydride (0.098 mL, 0.524 mmol) were added in that order to a stirred solution of 11 ($R_1$=Me, $R_2$=Me, $R_3$=SiPh$_2$Bu-t, $R_4$=H, configuration at C-1 being "S", at C-3 being "R") (18.0 mg, 0.02985 mmol) in dry dichloromethane (4 mL). The mixture was stirred for 72 h and was then evaporated. Flash chromatography of the residue over silica gel (1×18 cm) with 8:92 ether—petroleum ether gave the ester 14 ($R_1$=Me, $R_2$=Me, $R_3$=SiPh$_2$Bu-t, $R_4$=α-methylbutyroyl, configuration at C-1 being "S", at C-3 being "R", and at the α-position of the methylbutyroyl group being "S") [16.5 mg, 80% or 91% after correction for recovered 11 ($R_1$=Me, $R_2$=Me, $R_3$=Siph$_2$Bu-t, $R_4$=H, configuration at C-1 being "S", at C-3 being "R") (2.2 mg)]as a homogeneous (TLC, silica, 1:9 ether—petroleum ether) oil: $[α]_D^{27}$+147.10 (c 0.1414, CHCl$_3$); IR (CH$_2$Cl$_2$) 1727 cm$^{-1}$; $^1$H NMR (CDCl$_3$, 300.133 MHz) δ 0.87 (d, J=7.0 Hz, 3H), 0.88 (t, J=7.5 Hz, 3H), 1.04 (s, 9H), 1.07 (d, J=7.5 Hz, 3H), 1.11 (d, J=7.0 Hz, 3H), 1.15–1.75 (series of multiplets, 11H), 1.34 (s, 3H), 1.42 (s, 3H), 1.90 (ddd, J=15.0, 7.6, 2.0 Hz, 1H), 2.06 (dd, J=15.0, 4.0 Hz, 1H), 2.26 (dq, J=12.0, 2.8 Hz, 1H), 2.34 (q, J=7.0 Hz, 1H), 2.36–2.5 (m, 2H), 3.62–3.78 (m, 2H), 3.84 (dt, J=10.0, 6.7 Hz, 1H). 4.05–4.17 (m, 1H), 5.36 (q, J=2.5 Hz, 1H), 5.52 (bs, 1H), 5.79 (dd, J=9.5, 6.0 Hz, 1H), 5.99 (d, J=9.5, Hz, 1H), 7.3–7.48 (m, 6H), 7.6–7.72 (m, 4H); $^{13}$C NMR (CDCl$_3$, 75.46 MHz) δ 11.76, 13 86, 16.24, 19.24, 19.93, 22.84, 23.97, 26.88 (3C), 30.30, 30.74, 32.60, 33.9, 36.8, 37.38, 37.46, 39.41, 41.46, 59.66, 65.44, 67.94, 69.61, 98.42, 127.61, 129.42, 129.56, 132.00, 133.61, 133.99, 134.03, 135.59, 176.62; exact mass, m/z 686.4374 (Calcd for $C_{43}H_{62}O_5Si$, 686.4366).

Compound 14

($R_1$=Et, $R_2$=Me, $R_3$=SiPh$_2$Bu-t, $R_4$=α-methylbutyroyl, configuration at C-1 being "S", at C-3 being "R" and at the α-position of the methylbutyroyl group being "S")

Compound 14 ($R_1$=Et, $R_2$=Me, $R_3$=SiPh$_2$Bu-t, $R_4$=α-methylbutyroyl, configuration at C-1 being "S", at C-3 being "R", and at the α-position of the methylbutyroyl group being "S") was prepared in 90% in an analogous manner.

Compound 15

($R_1$=H, $R_2$=Me, $R_5$C(O)=β-methylbutyroyl, configuration at C-1 being "S", and at the α-position of the methylbutyroyl group being "S").

Tetrabutylammonium fluoride (1M in THF, 0.042 mL, 0.042 mmol) was added to a solution of 14 ($R_1$=H, $R_2$=Me, $R_3$=SiPh$_2$Bu-t, $R_4$=α-methylbutyroyl, configuration at C-1 being "S", and at the α-position of the methylbutyroyl group being "S") (24.9 mg, 0.0367 mmol) in dry THF (1.5 mL) and the mixture was stirred at room temperature for 1.75 h (TLC control). Water (0.5 mL) was added and the THF was evaporated (water-pump, room temperature). The residue was mixed with ethyl acetate (10 mL) and washed with water (4 mL). The aqueous layer was extracted with ethyl acetate (5 mL) and the combined organic extracts were washed with brine (10 mL), and dried (MgSO$_4$). Evaporation of the solvent and flash chromatography of the residue over silica gel (1.0×10.0 cm) with 1:2 ethyl acetate—petroleum ether gave 15 ($R_1$=H, $R_2$=Me, $R_5$C(O)=α-methylbutyroyl, configuration at C-1 being "S", and at the α-position of the methylbutyroyl group being "S") (14.8 mg, 92%): IR (film) 3600-3250, 1720 cm$^{-1}$; $^1$H NMR (CDCl$_3$, 400 MHz) δ 0.85 (d, 3H, J=7.0 Hz), 0.90 (t, 3H, J=7.0 Hz), 1.05–1.30 (m, 3H), 1.10 (d, 3H, J=7.0 Hz), 1.35 (s, 3H) 1.37–1.50 (m 3H) 1.45 (s 3H) 1.57–165 (m, 6H), 2.05–2.20 (m, 3H), 2.25–2.41 (m, 3H), 2.55 (bt, 1H, J=5.5, OH), 3.70–3.80 (m, 3H), 4.05–4.12 (m, 1H), 5.28–5.32 (bs, 1H), 5.52–5.57 (bs, 1H), 5.75 (dd, 1H, J=10.0, 6.0 Hz), 5.95 (d, 1 H, J=10.0 Hz); exact mass, m/z 434.3028 (calcd for $C_{26}H_{42}O_5$, m/z 434.3032).

Compound 15

($R_1$=Me, $R_2$=M ®, $R_5$C(O) methylbutyroyl, configuration at C-1 being "S", configuration at C-3 being "R", and at the α-position of the methylbutyroyl group being "S").

Tetrabutylammonium fluoride (1.1M in THF, 0.060 mL, 0.066 mmol) was added to a solution of 14 ($R_1$=Me, $R_2$=Me, $R_3$=SiPh$_2$Bu-t, $R_4$=α-methylbutyroyl, configuration at C-1 being "S", at C-3 being "R", and at the α-position of the methylbutyroyl group being "S") (16 mg, 0.02329 mmol) in dry THF (1 mL) and the mixture was stirred at room temperature for 3 h (TLC control). Evaporation of the solvent and flash chromatography of the residue over silica gel (1×16 cm) with ether—petroleum ether in the successive ratios of 2:3 and 3:2 gave 15 ($R_1$=Me, $R_2$=Me, R5C(0)=α-methylbutyroyl, configuration at C-1 being "S", configuration at C-3 being "R", and at the α-position of the methylbutyroyl group being "S") (10 mg, 95%) as a homogeneous (TLC, silica, 7:3 ether—petroleum ether) oil: IR (CH$_2$Cl$_2$) 3460, 1726 cm$^{-1}$; $^1$H NMR (CDCl$_3$, 400 MHz) δ 0.86 (d, J=7.5 Hz, 3H), 0.88 (t, J=7.5 Hz, 3H), 1.07 (d, J=7.0 Hz, 3H), 1.1 (d, J=7.0 Hz, 3H), 1.2–1.28 (m, 2H), 1.37 (s, 3H), 1.44 (s, 3H), 1.35–1.51 (m, 3H), 1.57–1.75 (m, 6H), 1.89 (ddd, J=15.0, 7.0, 2.5 Hz, 1H), 1.99 (dd, J=15.0, 3.5 Hz, 1H), 2.24 (dq, J=12.0, 2.0 Hz, 1H), 2.28–2.49 (m, 3H), 2.49–2.67 (bs, 1H), 3.69–3.84 (m, 3H), 4.04–4.13 (m, 1H), 5.36 (q, J=2.5 Hz, 1H), 5.52 (bs, 1H), 5.79 (dd, J=10.0, 6.0 Hz, 1H), 5.98 (d, J=10.0, Hz, 1H); $^{13}$C NMR (CDCl$_3$, 100.6 MHz) δ 11.73, 13.78, 16.19, 19.89, 22.78, 23.82, 26.83, 27.47, 30.20, 30.64, 32.56, 33.76, 36.78(2C), 37.26, 38.03, 41.41, 61.01, 67.84, 69.44, 69.50, 98.55, 128.17, 129.40, 131.84, 133.46, 176.62; exact mass, m/z 448.3189 (calcd for $C_{27}H_{44}O_5$, 448.3188).

Compound 15

($R_1$=Et, $R_2$=Me, $R_5$C(O)=α-methylbutyroyl, configuration at C-1 being "S", at C-3 being "R", and at the α-position of the methylbutyzroyl group being "S")

Compound 15 ($R_1$=Et, $R_2$=Me, $R_5$C(O)=α-methylbutyroyl, configuration at C-1 being "S", at C-3 being "R", and at the α-position of the methylbutyroyl group being "S") was prepared in 89% in an analogous manner.

Compound 16

($R_1$=H, $R_2$=Me, $R_5$C(O)=α-methylbutyroyl, configuration at C-1 being "S", and at the α-position of the methylbutyroyl group being "S")

Dry dimethyl sulfoxide (0.012 mL, 0.1658 mmol) was added to a stirred solution of oxalyl chloride (0.0086 mL, 0.0829 mmol) in dry dichloromethane (1 mL) at −78° C. (argon atmosphere). After 10 min the alcohol 15 ($R_1$=H, $R_1$=Me, $R_5$C(O)=α-methylbutyroyl, configuration at C-1 being "S", and at the α-position of the methylbutyroyl group being "S") (16.4 mg, 0.0377 mmol) in dry dichloromethane (1 mL plus 0.5 mL rinse) was added by cannula. After 20 min, dry triethylamine (0.0532 mL, 0.1885 mmol) was added and, after a further 10 min, the cold-bath was removed and the solution was stirred for 30 min. A few drops of water were then added and the mixture was concentrated (water-pump, below 35° C.). Flash chromatography of the residue over silica gel (1.0×15.0 cm) with 1:4 ethyl acetate—petroleum ether gave the aldehyde 16 ($R_1$=H, $R_2$=Me, $R_5$C(O)=α-methylbutyroyl, configuration at C-1 being "S", and at the α-position of the methylbutyroyl group being "S") as a homogeneous (TLC, silica, 1:4 ethyl acetate—petroleum ether) oil (15 mg, 92%): IR (film) 1720–1745 cm$^{-1}$; $^1$H NMR (CDCl$_3$, 200 MHz) δ 0.90 (d, 3H, J=7 Hz), 0.92 (t, 3H, J=7 Hz), 1.12 (d, 3H), J=7.0 Hz), 1.05–130 (m, 3H), 1.33 (s, 3H), 1.35–1.50 (m, 2H), 1.45 (s, 3H), 1.53–1.78 (m, 5H), 2.08–2.45 (m, 6H), 2.45 (dddd, 1H, J=16.0, 8.0, 2.5 Hz), 2.58 (dddd, 1H, J=16.0, 8.0, 2.5 Hz), 3.70–3.86 (m, 1H), 4.30–4.48 (m, 1H), 5.28–5.35 (m, 1H), 5.52–5.60 (m, 1H) , 5.75 (dd, 1H, J 9.8, 6.0 Hz), 5.98 (d, 1H, J=9.8 Hz), 9.79 (t, 1H, J=2.5 Hz) ; $^{13}$C NMR (CDCl$_3$, 50.32 MHz) δ 11.79, 13.81, 16.97, 19.79, 20.97, 23.67, 26.26, 26.73, 30.07, 30.91, 33.79, 36.82, 37.11, 37.64. 41.71, 49.87, 64.72, 67.62, 69.29, 98.79, 123.50, 128.13. 133.02, 133.90, 176.52, 200.90; exact mass, m/z 432.2865 (calcd. for $C_{26}H_{40}O_5$, m/z 432.2875)

Compound 16

($R_1$=Me, $R_2$=M Ⓡ, $R_5$C(O)=α-methylbutyroyl, configuration at C-1 being "S", at C-3 being "R", and at the α-position of the methylbutyroyl group being "S")

Dry dimethyl sulfoxide (0.010 mL, 0.1381 mmol) was added to a stirred solution of oxalyl chloride (0.0080 mL, 0.0771 mmol) in dry dichloromethane (1 mL) at −78° C. (argon atmosphere). After 10 min the alcohol 15 ($R_1$=Me, $R_2$=Me, $R_5$C(O)=α-methylbutyroyl, configuration at C-1 being "S", configuration at C-3 being "R", and at the α-position of the methylbutyroyl group being "S") (9.4 mg, 0.021 mmol) in dry dichloromethane (1 mL plus 0.5 mL rinse) was added by syringe. After 20 min, dry triethylamine (0.050 mL, 0.1771 mmol) was added and, after a further 10 min, the cold-bath was removed and the solution was stirred for 20 min more. A few drops of water were then added and the mixture was concentrated at room temperature. Flash chromatography of the residue over silica gel (1×16 cm) with 2:3 ether—petroleum ether gave aldehyde 16 ($R_1$=Me, $R_2$=Me, $R_5$C(O)=α-methylbutyroyl, configuration at C-1 being S, at C-3 being R, and at the α-position of the methylbutyroyl group being S) (9.1 mg, 97%) as a homogeneous (TLC, silica, 2:3 ether—petroleum ether) oil: $^1$H NMR (CDCl$_3$, 300.133 MHz) δ 0.87 (d, J=7.0 Hz, 3H), 0.88 (t, J=7.5 Hz, 3H), 1.07 (d, J=7.5 Hz, 3H), 1.11 (d, J=7.0 Hz, 3H), 1.13-1.76 (m, 8H), 1.36 (s, 3H), 1.45 (s, 3H), 1.89 (ddd, J=15.2, 7.6, 2.5 Hz, 1H), 2.01 (dd, J=15.2, 3.5 Hz, 1H), 2.24 (dq, J=12.0, 2.5 Hz, 1H), 2.29-2.65 (series of multiplets, 6H), 3.71-3.83 (m, 1H), 4.32-4.45 (m, 2H), 5.36 (q, J=3.0 Hz, 1H), 5.52 (bs, 1H), 5.78 (dd, J=9.5, 6.0 Hz, 1H), 5.99 (d, J=9.5, Hz, 1H), 9.78 (t, J=1 Hz, 1H); $^{13}$C NMR (CDCl$_3$, 75.469 MHz) δ 11.76, 13.86, 16.27, 19.83, 22.86, 23.90, 26.89, 27.55, 29.75, 30.09, 30.73, 32.65, 33.77, 36.83(2C), 37.37, 41.48, 49.88, 64.71, 67.91, 69.36, 98.81, 128.28, 129.51, 131.91, 133.49, 176.66, 201.05; exact mass, m/z 446.3041 (calcd for $C_{27}H_{42}O_5$, 4205, 446.30322).

Compound 16

($R_1$=Et, $R_2$=Me, $R_5$C(O)=α-methylbutyroyl, configuration at C-1 being "S", at C-3 being "R", and at the α-position of the methylbutyroyl group being "S")

Compound 16 ($R_1$=Et, $R_2$=Me, $R_5$C(O)=α-methylbutyroyl, configuration at C-1 being "S", at C-3 being "R", and at the α-position of the methylbutyroyl group being "S") was prepared in 91% in an analogous manner.

Compound 17

($R_1$=H, $R_2$=M Ⓡ, $R_5$C(O)=α-methylbutyroyl, configuration at C-1 being "S", and at the α-position of the methylbutyroyl group being "S")

Aqueous hydrochloric acid (10% v/v, 0.286 mL) was added to a solution of the aldehyde 16 ($R_1$=H, $R_2$=Me, $R_5$C(O)=α-methylbutyroyl, configuration at C-1 being "S", and at the α-position of the methylbutyroyl group being "S") (14.9 mg, 0.0344 mmol) in THF (0.714 mL) and the mixture was swirled and left at room temperature for 2 h under argon. By this stage all of the starting material had been hydrolyzed (TLC, silica, 7:13 THF—hexane). Solid sodium bicarbonate (300 mg) was added cautiously (swirling) followed by water (1 mL) and ethyl acetate (5 mL). The organic phase was separated and washed with water (5 mL), and the combined aqueous phases were extracted with ethyl acetate (5 mL). The combined organic extracts were dried (MgSO$_4$) and evaporated to afford, after drying for 12 h under oil-pump vacuum, a mixture of anomeric lactols 17 ($R_1$=H, $R_2$=Me, $R_5$C(O)=α-methylbutyroyl, configuration at C-1 being "S", and at the α-position of the methylbutyroyl group being "S") (12.0 mg, 88%). These were oxidized immediately without characterization.

Compound 17

($R_1$=Me, $R_2$=Me, $R_5$C(O)=α-methylbutyroyl, configuration at C-1 being "S", at C-3 being "R", and at the α-position of the methylbutyroyl group being "S")

Aqueous hydrochloric acid (10% v/v, 0.350 mL) was Me, $R_5$C(O)=α-methylbutyroyl, configuration at C-1 being "S", at C-3 being "R", and at the α-position of the methylbutyroyl group being "S") (8.8 mg, 0.0197 mmol) in THF (1 mL) and the mixture was swirled and left at room temperature for 4 h under argon. By this stage all of the starting material had been hydrolyzed (TLC, silica, ether). Solid sodium bicarbonate (200 mg) was added cautiously with stirring, followed by dichloromethane (10 mL) and water (2 mL). The organic phase was separated and washed with water (1×2 mL), and the combined aqueous phases were extracted with dichloromethane (4×5 mL). The combined organic extracts were dried (Na$_2$SO$_4$) and evaporated to afford, after drying for 12 h under oil-pump vacuum, a mixture of anomeric lactols 17 ($R_1$=Me, $R_2$=Me, $R_5$C(O)=α-methylbutyroyl, configuration at C-1 being "S", at C-3 being "R", and at the α-position of the methylbutyroyl group being "S") (7.8 mg, 97%). These were oxidized immediately.

Compound 17

($R_1$=Et, $R_2$=Me, $R_5$C(O)=α-methylbutyroyl, configuration at C-1 being "S", at C-3 being "R", and at the α-position of the methylbutyroyl group being "S")

Compound 17 ($R_1$=Et, $R_2$=Me, $R_5$C(O)=α-methylbutyroyl, configuration at C-1 being "S", at C-3 being "R", and at the α-position of the methylbutyroyl group being "S") was prepared in 80% in an analogous manner.

Compound 18

($R_1$=H, $R_2$=Me, $R_5$C(O)=α-methylbutyroyl, configuration at C-I being "S", and at the α-position of the methylbutyroyl group being "S")

[(+)-Compactin]

Silver carbonate on Celitel[1] (253 mg) was added to a stirred solution of the dry lactols 17 ($R_1$=H, $R_2$=Me, $R_5$C(O)=α-methylbutyroyl, configuration at C-1 being "S", and at the α-position of the methylbutyroyl group being "S") (12.0 mg, 0.0306 mmol) in dry toluene (2 mL) and the mixture was stirred at 95° C. for 2 h under argon. At this stage, TLC (silica, 7:13 THF—hexane) showed that all the starting material had reacted. The mixture was cooled to room temperature and filtered through a column of Celite (1.0 v 2.5 cm), the solids being washed with ethyl acetate (3×6 mL). Evaporation of the combined filtrates and flash chromatography of the residue over silica gel (1.0 v 12.0 cm) using first about 1 bed volume of 1:19 acetone—dichloromethane and then 1:9 acetone—dichloromethane gave synthetic compactin (7.3 mg, 61.2%): mp 148°-151° C. (lit[2] 152°

C.); $[\alpha]_D^{30}+218.50$ (c 0.8749, CH$_2$Cl$_2$). An authentic sample had $[\alpha]_D^{29}+221.15$ (c 3.2873, CH$_2$Cl$_2$).

[1]Balogh, v.; Fetizon, M.; Golfier, M. *J. Org. Chem.* 1971, 36, 1339.
[2]Brown, A. G.; Smale, T. C.; King, T. J.; Hasenkamp, R.; Thompson, R. H. *J. Chem. Soc. Perkin. Trans* 1 1976, 1165.

Compound 18

($R_1$=Me, $R_2$=Me, $R_5$C(O)=α-methylbutyroyl, configuration at C-1 being "S", at C-3 being "R", and at the α-position of the methylbutyroyl group being "S")

[(+)-Mevinolin]

Silver carbonate on Celite (262 mg) was added to a stirred solution of the dry lactols 17 ($R_1$=Me, $R_2$=Me, $R_5$C(O)=α-methylbutyroyl, configuration at C-1 being "S", at C-3 being "R", and at the α-position of the methylbutyroyl group being "S") (7.8 mg, 0.01918 mmol) in dry toluene (2 mL) and the mixture was stirred at 85°-95° C. (oil-bath temperature) for 1 h under argon. At this stage, TLC (silica, 9:1 ether—ethyl acetate) showed that all the starting material had reacted. The mixture was cooled to room temperature and filtered through a column of Celite (1×4 cm), the solids being washed with ethyl acetate (5×10 mL). Evaporation of the combined filtrates and flash chromatography of the residue over silica gel (1.×16 cm) using first ether and then 9:1 ether—ethyl acetate gave synthetic mevinolin 18 ($R_1$=Me, $R_2$=Me, $R_5$C(O)=α-methylbutyroyl, configuration at C-1 being "S", at C-3 being "R", and at the α-position of the methylbutyroyl group being "S") (6.0 mg, 77%) as a homogeneous [TLC, silica, 9:1 ether—ethyl acetate; $^1$H NMR (300 MHz)], colorless, crystalline solid. The material was recrystallized from dichloromethane—petroleum ether without change in its $^1$H NMR (300 MHz) spectrum, to afford long colorless needles: mp 155.5°-158.5° C. (lit.[1] 157°-159° C.); $[\alpha]_D^{27.5}+334.67$ (c 0.254275, CH$_3$CN). An authentic sample had $[\alpha]_D^{27.5}+331.60$ (c 0.10675, CH$_3$CN).

[1]Alberts, A.W.; Chen, J.; Kuron, G.; Hunt, V.; Huff, J.; Hoffman, C.; Rothrock, J.; Lopez, M.; Joshua, H.; Harris, E.; Patchett, A.; Monaghan, R.; Currie, S.; Stapley, E.; Albers-Schönberg. G.; Hensens, O.; Hirshfield, J.; Hoogsteen, K.; Liesch, J.; Springer, J. *Proc. Nat;. Acad. Sci. U.S.A.* 1980, 77, 3957.

Compound 18

($R_1$=Et, $R_2$=M3, $R_5$C(O)=α-methylbutyroyl, configuration at C-1 being "S", at C-3 being "R", and at the α-position of the methylbutyroyl group being "S")

(+)-3-Ethylcompactin]

Compound 18 ($R_1$=Et, $R_2$=Me, $R_5$C(O)=α-methylbutyroyl, configuration at C-1 being "S", at C-3 being "R", and at the α-position of the methylbutyroyl group being "S") was prepared in 72% in an analogous manner.

Compound 37

($R_1$=Me)

n-Butyllithium (1.6M in hexanes, 92 mL) was added dropwise from an addition funnel to a magnetically stirred and cooled (−78° C.) solution of the oxazolidinone 19 (26.05 g, 147 mmol) and 2,2,-dipyridyl (5 mg) in THF (250 mL). When all the butyllithium had been added the initially yellow solution turned brick red. Stirring was continued for 10 min and freshly distilled propionyl chloride (12.8 mL, 147.3 mmol) was injected over 10 min With stirring. Stirring was continued at −78° C. for 45 min and the cooling-bath was removed. After a further 45 min saturated ammonium chloride solution (25 mL) was added, the mixture was stirred for 10 min and then most of the THF was evaporated at 30° C. The residue was extracted with ethyl acetate (3×100 mL) and the combined organic extracts were washed with water (1×50 mL), dried (Na$_2$SO$_4$), and evaporated. Flash chromatography of the residual light yellow oil over silica gel (4×30 cm) with 3:7 ether—petroleum ether gave 37 ($R_1$=Me) (31.8 g, 92%) as a homogeneous (TLC, silica gel, 3:7 ether—petroleum ether) oil: IR(neat) 1782, 1703 cm$^{-1}$; $^1$H NMR (CDCl$_3$, 300 MHz) δ 1.21 (t, J=7.4 Hz, 3H), 2.78 (dd, J=9.7, 13.5 Hz, 1H), 2.835-3.08 (m, 2H), 3.30 (dd, J=13.5, 3.5 Hz, 1H), 4.12-4.25 (m, 2H), 4.67 (ddd, J=9.7, 7.0, 3.5 Hz, H), 7.13-7.4 (m, 5H); $^{13}$C NMR (CDCl$_3$, 75.469 MHz) δ 8.30, 29.19, 37.93, 55.16, 66.23, 127.34, 128.95, 129.42, 135.35, 153.52, 174.08; exact mass, m/z 233.1052 C$_{13}$H$_{15}$NO$_3$: C, 66.937; H, 6.48; N, 6.004. Found: C, 66.94; H, 6.43; N, 5.98.

Compound 37

($R_1$=Et)

Compound 37 ($R_1$=Et) was prepared in 86% in an analogous manner.

Compound 38

($R_1$=Me)

n-Butyllithium (1.6M in hexanes, 60.0 mL, 96.0 mmol) was added dropwise from an addition funnel to a magnetically stirred and cooled (ice-bath) solution of diisopropylamine (13.45 mL, 96.0 mmol) in THF (150 mL). The mixture was stirred for 10 min after the end of the addition, cooled to −78° C. and, after an additional 10 min, a solution of 37 ($R_1$=Me) (22.1 g, 94.74 mmol) in THF (75 mL) was injected over 25 min. Stirring was continued for a further 45 min at −78° C. and then freshly distilled allyl bromide (24.6 mL, 284.2 mmol) was injected over 5 min. The cooling-bath was removed and stirring was continued for 2.5 h and then saturated ammonium chloride solution (30 mL) was added. The mixture was stirred for 10 min and diluted with water (50 mL). Most of the THF was evaporated at 30° C. and the aqueous residue was extracted with ether (3×100 mL). The combined organic extracts were washed with brine (1×50 mL), dried (Na$_2$SO$_4$), and evaporated. Flash chromatography of the residual light yellow oil over silica gel (4×30 cm) with 1:3 ether—petroleum ether gave 38 ($R_1$=Me) (19.2 g, 74%) as a homogeneous (TLC, silica gel, 3:7 ether—petroleum ether) oil: IR (CHCl$_3$) 1780, 1699, 1386, 1210 cm$^{-1}$; $^1$H NMR (CDCl$_3$, 400 MHz) δ 1.19 (d, J=7.0 Hz, 3H), 2.24 (tquintet, J=7.0, 1.0 Hz, 1H), 2.53 (t quintet, J=7.0, 1.0 Hz, 1H), 2.70 (dd, J=13.5, 10.0 Hz, 1H), 3.28 (dd, J=13.5, 3.5 Hz, 1 H], 3.87 (sextet, J=7.0, 1H), 4.12-4.22 (m, 2H), 4.68 (ddd, J=10.5, 7.0, 3.5 Hz, 1H), 5.03-5.15 (m, 2H), 5.83 (tdd, J=17.0, 10.0, 7.0 Hz, 1H), 7.13-7.4 (m, 5H) ; $^{13}$C NMR (CDCl$_3$, 100.614 MHz) δ 16.46, 37.2, 38.02, 38.14, 55.42, 66.05, 117.23, 127.35, 128.97, 129.45, 135.33, 135.44, 153.15, 176.53; exact mass, m/z 273.1368 (Calcd for C$_{16}$H$_{19}$NO$_3$, 273 1365). Anal. Calcd for C$_{16}$H$_{19}$NO$_3$: C, 70.31; H, 7.006; N, 5.12. Found: C, 70.01; H, 6.93; N, 5.20.

Compound 38

($R_1$=Et)

Compound 38 ($R_1$=Et) was prepared in 74% in an analogous manner.

Compound 39

(R$_1$=Me)

Ozonized oxygen, cooled by passage through a glass coil immersed in a cooling-bath at −78° C., was bubbled into a cold (−78° C.) solution of 38 (R$_1$=Me) (15.0 g, 54.87 mmol) in dry dichloromethane (150 mL) for 1.5 h, by which stage the solution had acquired a violet color. Triphenylphosphine (43.07 g, 164.20 mmol) was added with stirring. After 30 min the cooling-bath was removed, stirring was continued for 2 h, and the solution was evaporated. The residue was taken up in the minimum amount of dichloromethane and flash chromatographed over silica gel (4×28 cm) first with 1:4 ether—petroleum ether (to remove unreacted triphenylphosphine), and then with 3:2 ether—petroleum ether gave 39 (R$_1$=Me) (14.6 g, 96%) as a homogeneous (TLC, silica gel, 7:3 ether—petroleum ether) oil: IR (CDCl$_3$) 1777, 1720, 1694, cm$^{-1}$; $^1$H NMR (CDCl$_3$, 300.133 MHz) δ 1.23 (d, J=7.2 Hz, 3H), 2.61 (ddd, J=18.8, 4.5, 1.0 Hz, 1H), 2.81 (dd, J=13.5, 9.8 Hz, 1H), 3.12 (dd, J=18.8, 9.8 Hz, 1H), 3.27 (dd, J=13.5, 3.5 Hz, 1H), 4.10-4.30 (m, 3H), 4.6-4.73 (m, 1H), 7.13-7.40 (m, 5H), 9.77 (m, 1H); $^{13}$C NMR (CDCl$_3$, 75.469 MHz) δ 17.04, 32.46, 37.56, 47.63, 55.34, 66.07, 127.25, 28.91, 129.47, 135.41, 153.00, 175.79, 199.92; exact mass, m/z 275.1154 (calcd for C$_{15}$H$_{17}$NO$_4$, 275.1157). Anal. Calcd for C$_{15}$H$_{17}$NO$_4$: C, 65.44;H, 6.22; N, 5.08. Found: C, 65.13; H, 6.29; N, 5.13.

Compound 39

(R$_1$=Et)

Compound 39 (R$_1$=Et) was prepared in 92% in an analogous manner.

Compound 40

(R$_1$=Me)

A mixture of 39 (R$_1$=Me) (1.08 q, 39.23 mmol), ethylene glycol (2.8 mL, 50.16 mmol), p-toluenesulfonic acid monohydrate (0.8 g, 4.2 mmol), and benzene (200 mL) to pass through a small column (2×4 cm) of type 4Å molecular sieves contained in a side-arm addition funnel fitted between the flask and the condenser. The solution was cooled, washed with saturated sodium bicarbonate solution (1×40 mL) and with brine (1×40 mL), and dried (Na$_2$SO$_4$). Evaporation of the solvent and flash chromatography of the residual light yellow oil over silica gel (4×22 cm) with 3:2 ether—petroleum ether gave 40 (R$_1$=Me) (10.9 g, 87%) as a homogeneous (TLC, silica gel, 3:2 ether—petroleum ether), colorless, crystalline solid: mp 63°-65° C.; [α]$_{28.5}$$^D$+15.225 (c 3.56, CHCl$_3$); IR (CHCl$_3$) 1779, 1699, 1389, cm$^{-1}$; $^1$H NMR (CDCl$_3$, 300 MHz) δ 1.22 (d, J=7.0 Hz, 3H), 1.81 (dt, J=14.2, 4.2 Hz, 1H), 2.33 (ddd, J=14.2, 9.5, 5.3 Hz, 1H), 2.68 (dd, J=13.0, 9.5 Hz, 1H), 3.35 (dd, J=13.5, 3.5 Hz, 1H), 3.75-3.98 (m, 4H), 3.98-4.2 (m, 3H), 4.6-4.7 (m, 1H), 4.98 (dd, J= 5.0, 4.0 Hz, 1H), 7.14-7.40 (m, 5H); $^{13}$C NMR (CDCl$_3$, 75.469 MHz) δ 18.2, 32.78, 37.48, 55.52, 64.56, 65.01, 65.81, 102.78, 127.15, 128.85, 129.37, 135.65, 153.02, 175.76; exact mass, m/z 319.1410 (calcd for C$_{17}$H$_{21}$NO$_5$, 319.14196). Anal. Calcd for C$_{17}$H$_{21}$NO$_5$: C, 63.93; H, 6.627; N, 4.386. Found: C, 63.86; H, 6.48; N, 4.37.

Compound 40

(R$_1$=Et)

Compound 40 (R$_1$=Et) was prepared in 85% in an analogous manner.

Compound 41

(R$_1$=Me)

A solution of 40 (R$_1$=Me) (10.7 g, 33.5 mmol) in THF (50 mL plus 25 mL as a rinse) was transferred by cannula to a magnetically stirred and cooled (ice-bath) solution of lithium aluminum hydride (3.893 g, 102.6 mmol) in THF (150 mL). Stirring was continued for 15 min, the cooling-bath was removed and, after a further 30 min, Celite (10 g) was added. The mixture was recooled in ice followed by successive dropwise addition of water (4 mL), 10% w/v aqueous sodium hydroxide (4 mL), and water (12 mL). The ice-bath was removed and stirring was continued for 15 min. The mixture was filtered and the solids were washed with ethyl acetate (2×50 mL). The combined filtrates were evaporated and flash chromatography of the residual oil over silica gel (4×28 cm) first with 2:3 ether—petroleum ether and then with 13:7 ether—petroleum ether gave 41 (R$_1$=Me) (4.71 g, 95%) as a homogeneous (TLC, silica gel, 13:7 ether—petroleum ether) oil. Continued elution with ether gave the oxazolidinone 19 (3.0 g, 50%). The hydroxy ketal 41 (R$_1$=Me) had: [α]$_D$$^{28}$+8.873 (c 5.59, CHCl$_3$); IR (CHCl$_3$) 3430, 2879, 1135, 1036 cm$^{-1}$; $^1$H NMR (CDCl$_3$, 300.133 MHz) δ 0.98 (d, J=7.0 Hz, 3H), 1.62-1.80 (m, 2H), 1.82-2.0 (m, 1H), 2.65 (bs, 1H), 3.4-3.58 (m, 2H),3.81-4.06 (m, 4H), 4.95 (dd, J=5.5, 4.5 Hz, 1H); $^{13}$C NMR (CDCl$_3$, 75.469 MHz) δ 17.77, 32.38, 38.14, 64.94 (2C), 68.01, 103.79; exact mass, m/z 145.0858 [Calcd for C$_7$H$_{13}$O$_3$ (M-1)$^+$, 145.0864]. Anal. Calcd for C$_7$H$_{14}$O$_3$: C, 57.51; H, 9.65. Found: C,57.72; H, 9.47.

Compound 41

(R$_1$=Et)

Compound 41 (R$_1$=Et) was prepared in 85% in an analogous manner.

Compound 42

(R$_1$=Me).

Dry DMSO (4.26 mL, 60.03 mmol) was injected dropwise into a stirred and cooled (−78° C.) solution of freshly distilled oxalyl chloride (2.75 mL, 31.7 mmol) in dry dichloromethane (75 mL). After 10 min a solution of 41 (R$_1$=Me) (4.6055 g, 31.5 mmol) in dichloromethane (30 mL) was injected over 30 min. The resulting mixture was stirred for a further 20 min and then dry triethylamine (15.0 mL, 107.62 mmol) was injected dropwise. Stirring was continued at −78° C. for 20 min, the cooling-bath was removed and, after 30 min, water (30 mL) was added. The mixture was stirred for 10 min and the aqueous layer was extracted with dichloromethane (2×40 mL). The combined organic layers were washed with 10% v/v aqueous hydrochloric acid (2×30 mL), saturated sodium bicarbonate solution (2×30 mL), and with brine (1×30 mL), and were dried (Na$_2$SO$_4$). The solvent was evaporated at 1 atm using a Vigreaux column and flash chromatography of the residue over silica gel (4×25 cm) with 3:7 ether—pentane gave (after evaporation of appropriate fractions in the same way) 42 (R$_1$=Me) (4.11 g, 90%) as a homogeneous (TLC, silica gel, 3:7 ether—petroleum ether) oil: $[\alpha]^{28}D -14.66$ (c 1.33, CHCl$_3$); IR (CDCl$_3$) 1728, cm$^{-1}$; $^1$H NMR (CDCl$_3$, 400.134 MHz) δ 1.15 (d, J=7.0 Hz, 3H), 1.76 (ddd, J=14.5, 5.5, 4.3 Hz, 1H), 2.15 (ddd, J=14.5, 8.0, 4.3 Hz, 1H), 2.55–2.66 (m, 2H), 3.80–4.01 (m, b 4H), 4.98 (t, J=4.2 Hz, 1H), 9.6 (d, J=2.5 Hz); exact mass, m/z 143.0706 [calcd for C$_7$H$_{12}$O$_3$ (M-1)$^+$, 143.0708]. Anal. Calcd for C$_7$H$_{12}$O$_3$: C, 58.318; H, 8.389. Found: C, 57.79; H, 8.45.

Compound 42

(R$_1$=Et)

Compound 42 (R$_1$=Et) was prepared in 82% in an analogous manner.

Compound 43

(R$_1$=Me)

n-Butyllithium (1.6M in hexanes, 18.1 mL, 29 mmol) was added from a syringe to a magnetically stirred and cooled (−15° C., ice-methanol bath) suspension of methyltriphenylphosphonium bromide (10.35 g, 29 mmol) in THF (120 mL). The rate of addition was controlled so that the internal temperature did not rise above −6° C. The resulting clear orange-red solution was stirred at −6° C. to 0° C. for 1 h, and then a solution of 42 (R$_1$=Me) (4.11 g, 28.5 mmol) in THF (20 mL plus 5 mL as a rinse) was injected dropwise over 15 min at 0° C. The mixture was stirred for a further 20 min at this temperature and was then partitioned between water (50 mL) and ether (3×40 mL). The combined organic extracts were washed with brine (1×50 mL) and dried (Na$_2$SO$_4$). The solvent was evaporated at 1 atm using a Vigreaux column and flash chromatography of the residue over silica gel (4×20 cm) with 2:8 ether—pentane gave (after evaporation of appropriate fractions in the same way) 43 (R$_1$=Me) (2.92 g, 72%) as a homogeneous (TLC, silica gel, 2:8 ether—petroleum ether) oil: $[\alpha]^{27}D$ −24.57 (c 8.69, CHCl$_3$); $^1$H NMR (CDCl$_3$, 300.133 MHz) δ 1.05 (d. J=7.0 Hz, 3H), 1.54–1.66 (dt, J=14.0, 6.3 Hz, 1H), 2.32–2.48 (m, 1H), 3.75–4.02 (m, 4H), 4.87 (dd, J=6.5, 4.7 Hz, 1H), 4.94 (ddd, J=10.5, 1.5, 1.0 Hz, 1H), 5.01 (dt, J=17.5, 1.5 Hz, 1H), 5.74 (ddd, J=17.5, 10.5, 6.5 Hz, 1H); $^{13}$C NMR (CDCl$_3$, 75.469 MHz) δ 20.51, 34.03, 40.48, 64.72 (2C), 103.47, 112.67, 143.76; exact mass, m/z 141.0916 [calcd for C$_8$H$_{13}$O$_2$ (M-1)$^+$, 141.0915].

Compound 43

(R$_1$=Et)

Compound 43 (R$_1$=Et) was prepared in 84% in an analogous manner.

Compound 6A (R$_1$=Me)

A solution of 43 (R$_1$=Me) (360 mg, 2.532 mmol) in ether (50 mL) was stirred vigorously for 23 h with 10% v/v aqueous hydrochloric acid (30 mL). The organic layer was separated and the aqueous layer was extracted with ether (3×50 mL). The combined organic layers were washed with saturated sodium bicarbonate solution (1×30 mL), water (1×30 mL), and brine (1×30 mL), and were then dried (Na$_2$SO$_4$). The solvent was evaporated at 1 atm using a Vigreaux column and Kugelrohr distillation of the residue at 1 atm gave 6A (R$_1$=Me) (173.4 mg, 69%). Compound 6A (R$_1$=Me) had: IR (CDCl$_3$) 1711 cm$^{-1}$; $^1$H NMR (CDCl$_3$, 400.134 MHz) δ 1.09 (d, J=7.0 Hz, 3H), 2.38 (ddd, J=17.0, 7.5, 2.5 Hz, 1H), 2.47 (ddd, J=17.0, 7.5, 2.5 Hz, 1H), 2.78 (tsept, J=7.0, 1.4 Hz, 1H), 5.00 (dt, J=10.5, 1.5 Hz, 1H), 5.04 (dt, J=17.6, 1.5 Hz, 1H), 5.79 (ddd, J=17.5, 10.5, 7.0 Hz, 1H), 9.74 (t, J=2.5 Hz); $^{13}$C NMR (CDCl$_3$, 100.614 MHz) δ 19.84, 32.2, 49.85, 113.57, 142.22, 202.04; exact mass, m/z 98.0718 (calcd for C$_6$H$_{10}$O, 98.0731).

Compound 6A (R$_1$=Et)

Compound 6A (R$_1$=Et) was prepared in 65% in an analogous manner.

The compounds of formula 18 in demonstrating powerful hypocholesterolemic properties can now be fully investigated by way of the synthetic routes of this invention. The drawbacks of the prior biological production of these compounds of formula 18, where R$_1$ was either hydrogen or methyl, is no longer a constraint. Radical substitutions in various regions of formula 18 (such as by R$_1$ and R$_5$) are now readily accomplished by this invention to produce compounds of formula 18 having even greater levels of hypocholesterolemic activity.

Biological Activity of Ethylcompactin

The following biological tests demonstrate the biological activity of ethylcompactin, one of the novel compounds of this invention in accordance with formula 18, wherein R$_1$ is ethyl, R$_2$ is H and R$_5$ is CH$_3$. By way of the synthesis route of this invention, the now available other compounds would have predictable biological activity for lowering cholesterol blood levels due to ethylcompactin activity demonstrated below.

Ethylcompactin and mevinolin were dissolved in DMSO. Aliquots (10 μl) of each were incubated with 50 μl of 50 mM Pot. phosphate pH 7.4, 70 mM KCl, 30 mM EDTA, 10 mM DTT for 30 min at 37° C. to delactonize the compounds. Control incubations were done with 10 μL DMSO.

Assay of HMGCoA reductase was carried out as described by George and Ramasarma, [George R., Ramasarma, T., *Biochem. J.* (1977) 162:493–499]. At the end of 30 min, incubation for delocalization, rat liver microsome (75 μg protein) were added to each tube along with glucose-6-phosphate (577 μM) glucose-6-phosphate dehydrogenase (0.05 unit/assay) and MADPH (53 μ) and incubated for an additional 10 min at 37° C.

HMGCoA reductase reaction was initiated by the additon of 3-$^{14}$C-HMGCoA (240 mM, final) and carried out for 20 min at 37° C. in a total volume of 100 μl. The reaction was terminated by the addition of 5N HCl (25 μl) containing known amounts of $^3$-H-Mevalonolactone as internal standard and non-radioactive mevalonolactone (0.6 mg/assay) as carrier. Mevalonic acid formed in the assay was allowed to lactonize by incubating the mixture for 30 min at 37° C. The precipitated protein was removed by centrifugation in a microfuge. An aliquot of the supernatant (40 μl) was applied on silica gel G (0.25 mm thickness) plates and the chromatogram developed with Acetone:Benzene (3:2). The spot corresponding to the mevalonolactone (R$_f$0.5) was scraped off and the radioactivity estimated by liquid scintillation counting. Mevalonic acid formed was calcualted from the recovery of internal standard. Microsomal protein was estimated by the method of Lowry [*J. Biol. Chem.* (1951) 193:265–275] after precipitation according to Bensadoun and Weinstein [*Anal. Biochem.* (1976) 70:241-250]. The specific activity of HMGCoA reductase is expressed as p moles of mevalonic acid formed per minute per mg of microsomal protein.

Effect of Ethylcompactin and Mevinolin on
Rat Liver 3-hydroxy-3-methylglutarylcoenzyme A
Reductase Activity in Vitro

| Compound | Concentration: in Assay | HMGCoA Reductase Activity pmol Mevalonate formed/min/ mg microsomal protein |
| --- | --- | --- |
| Ethyl Compactin | 1 nM | 730 |
|  | 100 nM | 361 |
| (in 10 μl DMSO) | 1 μM | 182 |
|  | 10 μM | 20 |
| Mevinolin | 1 nM | 609 |
| (in 10 μl DMSO) | 100 NM | 303 |
|  | 1 μM | 113 |
|  | 10 μM | 52 |
| DMSO | 10 μl | 652 |
| None | — | 1254 |

Although preferred embodiments of the invention are described herein in detail, it will be understood by those skilled in the art that variations may be made thereto without departing from the spirit of the invention or the scope of the appended claims.

I claim:

1. A process for preparing compounds of the formula:

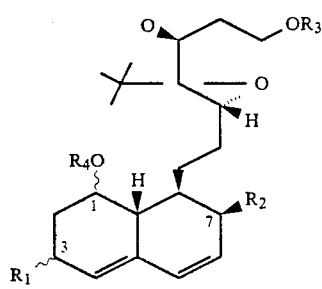

(10)

wherein:

$R_1$ is H, lower alkyl (1 to 6 C), lower dialkyl (1 to 6 C), lower cycloalkyl (3 to 7 C), or lower dicycloalkyl (3 to 7 C);

$R_2$ is H, lower alkyl (1 to 6 C), or lower cycloalkyl (3 to 7 C);

$OR_3$ and $OR_4$ are differentially protected hydroxyl groups;

said process comprising the step of cyclizing a compound of the formula:

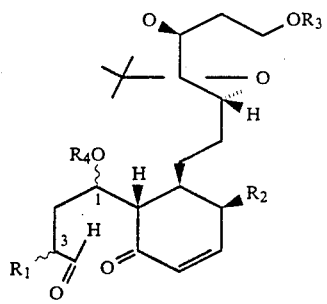

(9)

wherein $R_1$, $R_2$, and $R_3$ are as above, $R_4$ equals H, said cyclizing step comprises treating said compound with a low valent titanium composition prepared by reducing a titanium salt with an amount of a reducing agent less than the stoichiometric amount of said reducing agent required to reduce said titanium salt to a zero valence.

2. A process of claim 1 wherein $R_3$ is $SiPh_2Bu$-t and $R_4$ is H, $SiEt_3$ or $SiMe_3$.

3. A process of claim 1 wherein the stereochemistry at C-3 is in the R configuration.

4. A process of claim 1 wherein the stereochemistry at C-3 is in the S configuration.

5. A process of claim 1 wherein said amount of said reducing agent is approximately two-thirds of the said stoichiometric amount needed to reduce a titanium $+3$ salt to the zero valent state.

6. A process of claim 1 wherein said reducing agent is a potassium composition used in a molar ratio of two moles of potassium to 1 mole of titanium 3+ salt.

7. A process of claim 6 wherein $C_8K$ is reacted with titanium trichloride in the molar amount of 2 moles to one mole.

8. A process of claim 7 wherein the overall molar amounts with respect to one mole of the compound of formula 9 is 34 moles of $C_8K$ and 17 moles of $TiCl_3$.

9. A process of claim 8 wherein a suitable solvent in which said reaction is conducted is DME.

10. A process of claim 1 wherein said reducing agent is sodium naphthalene used in a molar ratio of 2.8 moles of sodium naphthalene to one mole of a titanium (IV) salt.

11. A process of claim 10 wherein sodium naphthalene is reacted with titanium tetrachloride in the molar ratio of 2.8 moles to one mole.

12. A process of claim 11 wherein the overall molar amounts with respect to one mole of the compound of formula 9 is 44.8 moles of sodium naphthalene and 16 moles of titanium tetrachloride.

13. A process of claim 12 wherein a suitable solvent in which said reaction is conducted is THF.

14. A process of claim 6 wherein said titanium 3+ salt is titanium trichloride.

* * * * *

UNITED STATES PATENT AND TRADEMARK OFFICE
CERTIFICATE OF CORRECTION

PATENT NO. : 5,072,002

DATED : Dec. 10, 1991

INVENTOR(S) : Clive et al.

It is certified that error appears in the above-identified patent and that said Letters Patent is hereby corrected as shown below:

On the title page,

Under "References Cited PUBLICATIONS", in the first cited publication delete "Meuinic Acido" and substitute --Mevinic Acids-- therefor.

Under "References Cited PUBLICATIONS", in the second cited publication please delete "Meuinolin" and substitute --Mevinolin-- therefor.

Under "References Cited PUBLICATIONS", in the third cited publication delete "McMarrg" and substitute --McMurry--.

Under "References Cited PUBLICATIONS", in the fourth cited publication delete "McMurray" and substitute --McMurry-- therefor.

At column 14, line 23, delete ""(IV) salt titanium" and substitute --titanium (IV) salt-- therefor.

At column 16, line 15, delete "cis" and substitute --$\underline{cis}$-- therefor.

At column 17, line 26, delete "S-maleic" and substitute --$\underline{S}$-maleic-- therefor.

At column 20, line 33, delete "$[\alpha]_D^{20}$-28.6" and substitute --$[\alpha]^{20}_D$ -28.6-- therefor.

At column 20, line 63, delete "$[\alpha]_D^{25}$-18.08" and substitute --$[\alpha]^{25}_D$ -18.08-- therefor.

UNITED STATES PATENT AND TRADEMARK OFFICE
CERTIFICATE OF CORRECTION

PATENT NO. : 5,072,002
DATED : Dec. 10, 1991
INVENTOR(S) : Clive et al.

It is certified that error appears in the above-identified patent and that said Letters Patent is hereby corrected as shown below:

At column 21, line 9, delete "$(R_3+H)^1$" and substitute --$(R_3+H).^1$-- therefor.

At column 22, line 18, delete "$[\alpha]_D+4.42$" and substitute --$[\alpha]^{28}_D +4.42$-- therefor.

At column 22, line 20, delete "Hz)." and substitute --Hz),-- therefor.

At column 22, line 20, delete "2H)." and substitute --2H),-- therefor.

At column 22, line 20, delete "(m." and substitute --(m,-- therefor.

At column 22, line 21, delete "1H)." and substitute --1H),-- therefor.

At column 22, line 21, delete first occurrence of "(m." and substitute --(m,-- therefor, and delete second occurrence of "(m." and substitute --(m,-- therefor.

At column 23, line 18, delete "$[\alpha]_D^{23}-5.46$" and substitute --$[\alpha]^{23}_D -5.46$-- therefor.

At column 23, line 25 and 26, delete "133 67" and substitute -- 133.67-- therefor.

At column 23, line 67, delete "s.68" and substitute --8.68-- therefor.

UNITED STATES PATENT AND TRADEMARK OFFICE
CERTIFICATE OF CORRECTION

PATENT NO. : 5,072,002
DATED : Dec. 10, 1991
INVENTOR(S) : Clive et al.

It is certified that error appears in the above-identified patent and that said Letters Patent is hereby corrected as shown below:

At column 24, line 7, after "2.3M", insert --in--.

At column 25, line 43, delete "$[\alpha]_D^{28}+0.468$" and substitute --$[\alpha]^{28}_D +0.468$--.

At column 26, lines 32 and 33, delete "[1]Oeda, H. Bull *Soc. Chem. Jpn.* 1938, 13, 465. [2]Evans, D.A.; Weber. A.E. *J. Am Chem. Soc.* 1986, 108, 6757."

At column 26, line 55, insert --[1]Oeda, H. Bull *Soc. Chem. Jpn.* 1938, 13, 465. [2]Evans, D.A.; Weber. A.E. *J. Am Chem. Soc.* 1986, 108, 6757.--

At column 28, line 16, delete "$[\alpha]_D^{20}$" and substitute --$[\alpha]^{20}_D$-- therefor.

At column 30, line 25, delete "$[\alpha]_D^{26} - 25.58$" and substitute --$[\alpha]^{26}_D -25.58$-- therefor.

At column 30, line 26, delete "$[\alpha]hd D^{25}$" and substitute --$[\alpha]^{25}_D$-- therefor.

At column 30, line 55, delete "$[\alpha]_D^{25} - 16.3$" and substitute --$[\alpha]^{25}_D -16.3$-- therefor.

At column 31, line 7, delete "$[\alpha]_D^{25} - 18.64$" and substitute --$[\alpha]^{25}_D -18.64$-- therefor.

At column 32, line 56, delete "Well" and substitute --well-- therefor.

UNITED STATES PATENT AND TRADEMARK OFFICE
CERTIFICATE OF CORRECTION

PATENT NO. : 5,072,002
DATED : Dec. 10, 1991
INVENTOR(S) : Clive et al.

It is certified that error appears in the above-indentified patent and that said Letters Patent is hereby corrected as shown below:

At column 32, line 59, delete "$[\alpha]_D^{28} -47.9$" and substitute --$[\alpha]^{28}_D -47.9$-- therefor.

At column 43, line 2, delete "$C_{34}H_{43}O_5Si$" and substitute --$C_{33}H_{43}O_5Si$-- therefor.

At column 34, line 2, delete "$(M-CH_3)^+91$" and substitute --$(M-CH_3)^+$-- therefor.

At column 34, line 37, delete "$[\alpha]_D^{27}$" and substitute --$[\alpha]^{27}_D$-- therefor.

At column 35, line 24, delete "(Val-" and substitute --(val- -- therefor.

At column 36, line 5, delete "I H" and substitute --1H-- therefor.

At column 36, line 5, insert a --,-- after "3.5".

At column 36, line 6, insert --0.5-- before "Hz".

At column 36, line 14, delete "$M--CH_3--C_6H_{10}O)$" and substitute --$M--CH_3--C_6H_{10}O$) therefor.

At column 36, line 34, insert --.-- before "Water".

At column 36, line 46, delete "6 0.55" and substitute --δ 0.55-- therefor.

UNITED STATES PATENT AND TRADEMARK OFFICE
CERTIFICATE OF CORRECTION

PATENT NO. : 5,072,002
DATED : Dec. 10, 1991
INVENTOR(S) : Clive et al.

It is certified that error appears in the above-identified patent and that said Letters Patent is hereby corrected as shown below:

At column 36, line 58, delete "[17.20 (q)]2," --[17.20 (q)]$^2$-- therefor.

At column 36, line 59, delete "9.42 (t)," and substitute --29.42 (t),-- therefor.

At column 36, line 60, delete "3.89 (t)," and substitute --33.89 (t),-- therefor.

At column 36, line 62, delete "54.75 (d)]," and substitute --[54.75 (d)],-- therefor.

At column 36, line 68, delete "$C_{44}H_{68}O_5Si2$," and substitute --$C_{44}H_{68}O_5Si_2$,-- therefor.

At column 37, line 1, delete "$C_{44}H_{68}O_5Si2$," and substitute --$C_{44}H_{68}O_5Si_2$,-- therefor.

At column 38, line 10, delete "(15 m9)." and substitute --(15 mg).-- therefor.

At column 38, line 29, delete "69.!2" and substitute --69.12-- therefor.

At column 38, line 54, delete "(1 x b 18 cm)" and substitute --(1 x 18 cm)-- therefor.

At column 39, line 40, delete "mL)2" and substitute --mL)$^2$-- therefor.

At column 39, line 43, after "h" insert --,--.

UNITED STATES PATENT AND TRADEMARK OFFICE
CERTIFICATE OF CORRECTION

PATENT NO. : 5,072,002

DATED : Dec. 10, 1991

INVENTOR(S) : Clive et al.

It is certified that error appears in the above-identified patent and that said Letters Patent is hereby corrected as shown below:

At column 40, line 3, delete "$C_{42}H_{66}O_4Si2$" and substitute --$C_{43}H_{66}O_4Si_2$-- therefor.

At column 40, line 48, delete "1.46--1 92" and substitute --1.461.92-- therefor.

At column 40, line 67, delete "$R_3$ = Siph$_2$Bu-t," and substitute --$R_3$ = SiPh$_2$Bu-t,-- therefor.

At Column 41, line 29, delete "0.05i" and substitute --0.051-- therefor.

At column 41, line 47, delete "3580--3300 cm$^{31}$" and substitute --3580--3300 cm$^{-1}$-- therefor.

At column 41, line 65, delete "(Calcd" and substitute --(calcd-- therefor.

At column 42, line 19, delete "(100 mL)" and substitute --(10 mL)-- therefor.

At column 42, line 58, delete "$R_3$ = Siph-" and substitute --$R_3$ = SiPh-- therefor.

At column 43, line , delete "Whole" and substitute --whole-- therefor.

UNITED STATES PATENT AND TRADEMARK OFFICE
CERTIFICATE OF CORRECTION

PATENT NO. : 5,072,002
DATED : Dec. 10, 1991
INVENTOR(S) : Clive et al.

It is certified that error appears in the above-indentified patent and that said Letters Patent is hereby corrected as shown below:

At column 43, line 27, delete "0.o5" and substitute --0.05-- therefor.

At column 43, line 33:, delete "1.4" and substitute --1:4-- therefor.

At column 43, line 53, delete "Siph$_2$Bu-t" and substitute --SiPh$_2$Bu-t-- therefor.

At column 43, line 57, after "=" insert --H, configuration at C-1 being "S" and at C-3 being "R") was--.

At column 44, line 13, delete "$[\alpha]_D^{27}$" and substitute --$[\alpha]^{27}_D$-- therefor.

At column 44, line 29, delete "672 4207" and substitute --672.4207-- therefor.

At column 44, line 52, delete "Siph$_2$Bu-t" and substitute --SiPh$_2$Bu-t-- therefor.

At column 44, line 55, delete "$[\alpha]_D^{27}$" and substitute --$[\alpha]^{27}_D$-- therefor.

At column 45, line 17, delete "$\beta$-methylbutyroyl," and substitute --$\alpha$-methylbutyroyl-- therefor.

UNITED STATES PATENT AND TRADEMARK OFFICE
CERTIFICATE OF CORRECTION

PATENT NO. : 5,072,002
DATED : Dec. 10, 1991
INVENTOR(S) : Clive et al.

It is certified that error appears in the above-identified patent and that said Letters Patent is hereby corrected as shown below:

At column 45, line 42, delete "1.57--165" and substitute --1.57--1.65-- therefor.

At column 46, line 5, delete "1.2--1.28" and substitute --1.12--28-- therefor.

At column 46, line 36, delete "(I mL)" and substitute --(1 mL)-- therefor.

At column 46, line 57, delete "(d, 3 H)," and substitute --(d, 3 H,-- therefor, and delete "1.05--130" and substitute --1.05--1.30-- therefor.

At column 47, line 3, delete "$R_2 = M^{\circledR}$," and substitute --$R_2$ = Me,-- therefor.

At column 47, line 39", delete --4205,--.

At column 47, line 53, delete "$R_2 = M^{\circledR}$," and substitute --$R_2$ = Me,-- therefor.

At column 48, line 17, insert --added to a solution of the aldehyde 16 ($R_1$ = Me, $R_2$ =-- before "Me,".

At column 48, line 53, delete "Celite1'" and substitute --Celite[1]-- therefor.

UNITED STATES PATENT AND TRADEMARK OFFICE
CERTIFICATE OF CORRECTION

PATENT NO. : 5,072,002

DATED : Dec. 10, 1991

INVENTOR(S) : Clive et al.

It is certified that error appears in the above-identified patent and that said Letters Patent is hereby corrected as shown below:

At column 49, line 1, delete "$[\alpha]_D^{30}$" and substitute --$[\alpha]^{30}_D$-- and delete "(c 0.8749," and substitute --(c 0.38749,-- therefor.

At column 49, line 36, delete "$[\alpha]_D^{27.5}$" and substitute --$[\alpha]^{27.5}_D$-- therefor.

At column 49, line 37, delete "$[\alpha]_D^{27.5}$" and substitute --$[\alpha]^{27.5}_D$-- therefor.

At column 50, line 54, delete "H]," and substitute --H),-- therefor.

At column 50, line 60, delete "(Calcd" and substitute --(calcd-- therefor.

At column 51, line 27, delete "28.91" and substitute --128.91-- therefor.

At column 51, line 42, delete "(1.08 q," and substitute --(1.08 g,"-- therefor.

At column 51, line 45, after "mL)" insert --was refluxed for 4.5 h with provision for the condensate--.

At column 52, line 29, delete "$[\alpha]_D^{28}$" and substitute --$[\alpha]^{28}_D$-- therefor.

At column 53, line 2, delete "$[\alpha]^{28}D$" and substitute --$[\alpha]^{28}_D$-- therefor.

UNITED STATES PATENT AND TRADEMARK OFFICE
CERTIFICATE OF CORRECTION

PATENT NO. : 5,072,002
DATED : Dec. 10, 1991
INVENTOR(S) : Clive et al.

It is certified that error appears in the above-indentified patent and that said Letters Patent is hereby corrected as shown below:

At column 53, line 6, after "(m," delete --b--.

At column 53, line 8, delete "C7H12O3" and substitute --$C_7H_{12}O_3$-- therefor.

Signed and Sealed this

Twenty-third Day of November, 1993

Attest:

BRUCE LEHMAN

*Attesting Officer*    *Commissioner of Patents and Trademarks*